(12) United States Patent
Tsapis et al.

(10) Patent No.: US 12,150,996 B2
(45) Date of Patent: Nov. 26, 2024

(54) POLYMERIC PRODRUGS AND SUBCUTANEOUS AND/OR INTRAMUSCULAR ADMINISTRATION THEREOF

(71) Applicants: CENTRE NATIONAL DE LA RECHERCHE SCIENTIFIQUE, Paris (FR); UNIVERSITE PARIS-SACLAY, Saint-Aubin (FR)

(72) Inventors: Nicolas Tsapis, Paris (FR); Julien Nicolas, Igny (FR); Tanguy Boissenot, Paris (FR); Alexandre Bordat, Paris (FR)

(73) Assignees: Centre National De La Recherche Scientifique, Paris (FR); Universite Paris-Saclay, Gif-Sur-Yvette (FR)

(*) Notice: Subject to any disclaimer, the term of this patent is extended or adjusted under 35 U.S.C. 154(b) by 0 days.

(21) Appl. No.: 16/764,492

(22) PCT Filed: Nov. 16, 2018

(86) PCT No.: PCT/EP2018/081636
§ 371 (c)(1),
(2) Date: May 15, 2020

(87) PCT Pub. No.: WO2019/097025
PCT Pub. Date: May 23, 2019

(65) Prior Publication Data
US 2020/0353090 A1    Nov. 12, 2020

(30) Foreign Application Priority Data

Nov. 17, 2017 (FR) ................................ 17 60868
Nov. 17, 2017 (FR) ................................ 17 60869

(51) Int. Cl.
*A61K 9/00* (2006.01)
*A61K 47/58* (2017.01)
(Continued)

(52) U.S. Cl.
CPC ............ *A61K 47/58* (2017.08); *A61K 9/0019* (2013.01); *A61K 49/0041* (2013.01);
(Continued)

(58) Field of Classification Search
CPC ...................................................... A61K 47/58
See application file for complete search history.

(56) References Cited

U.S. PATENT DOCUMENTS

2010/0166695 A1    7/2010    Bundle et al.

FOREIGN PATENT DOCUMENTS

| JP | 2012505228 A | 3/2012 |
|---|---|---|
| JP | 2014518264 A | 7/2014 |

(Continued)

OTHER PUBLICATIONS

Mei, Pharmaceutical nanotechnology for oral delivery of anticancer drugs, Advanced Drug Delivery Reviews, 2013, 65, 880-890 (2013).*
(Continued)

*Primary Examiner* — Paul W Dickinson
(74) *Attorney, Agent, or Firm* — Pearne & Gordon LLP

(57) ABSTRACT

The invention relates to new prodrugs of active molecules. These prodrugs allow, in particular, the subcutaneous or intramuscular administration of active molecules of which the subcutaneous or intramuscular administration is problematic or impossible, in particular because of the toxicity at the injection site. The prodrugs according to the invention comprise an active ingredient, covalently linked with a polymer chain, preferably a hydrophilic and/or thermosensitive polymer chain.

(Continued)

The invention relates, in particular, to polymeric prodrugs comprising a polymer chain formed at least in part by acrylamide monomer or one of its derivatives, said polymer comprising a proximal part and a terminal part; a first pharmaceutically active molecule covalently coupled to the proximal part of the polymer; possibly a second pharmaceutically active molecule covalently coupled to the terminal part of the polymer.

17 Claims, 14 Drawing Sheets

(51) Int. Cl.
*A61K 49/00* (2006.01)
*C08F 220/56* (2006.01)
*C08F 293/00* (2006.01)

(52) U.S. Cl.
CPC ........ *A61K 49/0054* (2013.01); *C08F 220/56* (2013.01); *C08F 293/005* (2013.01); *C08F 2438/03* (2013.01)

(56) References Cited

FOREIGN PATENT DOCUMENTS

| JP | 2017203028 A | 11/2017 |
|---|---|---|
| WO | 2010/042638 A2 | 4/2010 |
| WO | 2013/002636 A1 | 1/2013 |

OTHER PUBLICATIONS

Louage, Well-Defined Polymer-Paclitaxel Prodrugs by a Grafting-from-Drug Aproach, Angew. Chem. Int. Ed. 2016, 55, 11791-11796 (2016).*

Sun, A prodrug micellar carrier assembled from polymers with pendant farnesyl thiosalicylic acid moieties for improved delivery of paclitaxel, Acta Biomaterialia, 2016, 43, 282-291 (Year: 2016).*

Shi, Reversible Addition—Fragmentation Chain Transfer Synthesis of a Micelle-Forming, Structure Reversible Thermosensitive Diblock Copolymer Based on the N-(2-Hydroxy propyl) Methacrylamide Backbone, ACS Macro Letters, Feb. 2013, 403-408 (Year: 2013).*

International Search Report for PCT/EP2018/081636 dated Feb. 12, 2019.

Search Report for French Application No. 17 60868 dated Aug. 24, 2018.

Search Report for French Application No. 17 60869 dated Oct. 2, 2018.

Louage et al., "Well-Defined Polymer-Paclitaxel Prodrugs by a Grafting-from-Drug Approach", Angewandte Chemie International Edition, vol. 55, No. 39, Aug. 25, 2016, pp. 11791-11796, XP055547602.

Williams et al., "RAFT-Derived Polymer-Drug Conjugates: Poly(hydroxypropyl methacrylamide) (HPMA)-7-Ethyl-10-hydroxycamptothecin (SN-38) Conjugates", CHEMMEDCHEM, vol. 7, No. 2, Dec. 5, 2011, pp. 281-291, XP055547570.

Bao, et al., "Structure-cytotoxicity relationship of drug-initiated polymer prodrug nanoparticles", Polymer Chemistry, vol. 8, No. 34, Jan. 1, 2017, pp. 5174-5184, XP55501540.

Bao, et al., "Self-stabilized, hydrophobic or PEGylated paclitaxel polymer prodrug nanoparticles for cancer therapy", Polymer Chemstry, vol. 9, No. 6, Jan. 1, 2018, pp. 687-698, XP55501677.

Huang, et al., "Self-assembled UCST-Type Michelles as Potential Drug Carriers for Cancer Therapeutics", Macromolecular Chemistry and Physics, vol. 216, No. 9, May 1, 2015, pp. 1014-1023, XP055501836; and "Suppporting Information—Self-assembled UCST-Type Michelles as Potential Drug Carriers for Cancer Therapeutics", 2015, pp. 1-7, XP055502000.

Tong, et al., "Gadolinium/DOTA functionalized poly(ethylene glycol)-block-poly(acrylamide-co-acrylonitrile) micelles with synergistically enhanced cellular uptake for cancer theranosticst", RSC Advances, vol. 6, No. 56, Jan. 1, 2016, pp. 50534-50542, XP055511497.

Rui et al., "Synthesis and evaluation of a backbone biodegradable multiblock HPMA copolymer nanocarrier for the systemic delivery of paclitaxel", Journal of Controlled Release, Elsevier, Amsterdam, NL., vol. 166, No. 1, Dec. 20, 2012, pp. 66-74, XP028968971.

Yang etal., "NIR-controlled morphology transformation and pulsatile drug delivery based on multifunctional phototheranostic nanoparticles for photoacoustic imaging-guided photothermal-chemotherapy", Biomaterials, vol. 176, Sep. 1, 2018, pp. 1-12, XP055548321 and Supporting Information "NIR-controlled morphology transformation and pulsatile drug delivery based on multifunctional phototheranostic nanoparticles for photoacoustic imaging-guided photothermal-chemotherapy" Biomaterials, Sep. 1, 2018, pp. 1-12, XP055548315.

Wei-Shuo et al., "Mild microwave activated, chemo-thermal combinational tumor therapy based on a targeted, thermal-sensitive and magnetic micelle", Biomaterials, Elsevier Science Publishers BV., Barking, GB, vol. 131, Mar. 30, 2017, pp. 36-46. XP09991672.

Weishuo et al., "Antitumor Drug Delivery Modulated by A Polymeric Micelle with an Upper Critical Solution Temperature", Angewandte Chemie International Edition, vol. 54, No. 10, Jan. 28, 2015, pp. 3126-3131, XP055501687.

Pineda-Contreras et al., "pH dependent thermoresponsive behavior ofacrylamide-acrylonitrile UCST-type copolymers in aqueous media", Polymer Chemistry, vol. 7, No. 10, Jan. 1, 2016, pp. 1979-1986, XP055502089 and Pineda-Contreras et al., "Supporting Information—pH dependent thermoresponsive behavior ofacrylamide-acrylonitrile UCST-type copolymers in aqueous media", 2016, pp. 1-6.

Maksimenko et al., "Significant Tumor Growth Inhibition from Naturally Occurring Lipid-Containing Polymer Prodrug Nanoparticles Obtained by the Drug-Initiated Method", Chemistry of Materials, vol. 26, No. 12, Jun. 11, 2014, pp. 3606-3609, XP055501679.

Delplace et al., "Recent trends in the design of anticancer polymer prodrug nanocarriers", Polymer Chemistry, vol. 5, No. 5, Jan. 1, 2014, pp. 1529-1544, XP055501541.

Bordat et al., "A Polymer Prodrug Strategy to Switch from Intravenous to Subcutaneous Cancer Therapy for Irritant/Vesicant Drugs"; Journal of the American Chemical Society (JACS), vol. 144, pp. 18844-18860; (2022).

Burckbuchler, V., et al., "Rheological and syringeability properties of highly concentrated human polyclonal immunoglobulin solutions", European Journal of Pharmaceutics and Biopharmaceutics, 76 (2010) 351-356.

Ceruti, M., et al., "Preparation, characterization, cytotoxicity and pharmacokinetics of liposomes containing water-soluble prodrugs of paclitaxel", Journal of Controlled Release, 63 (2000) 142-153.

Nguyen, T., et al., "Practical Synthetic Route to Functionalized Rhodamine Dyes", Organic Letters, 2003, vol. 5, No. 18, 3245-3248.

* cited by examiner

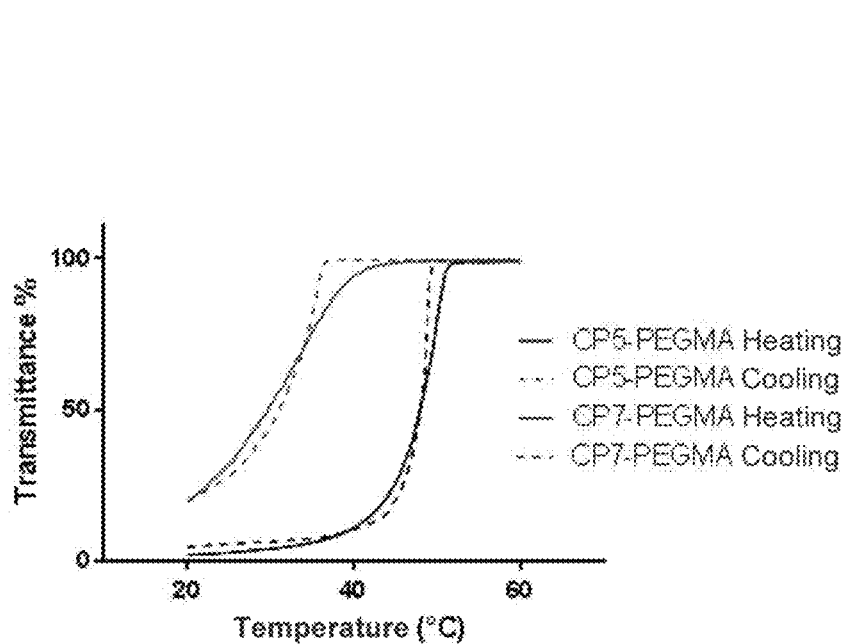
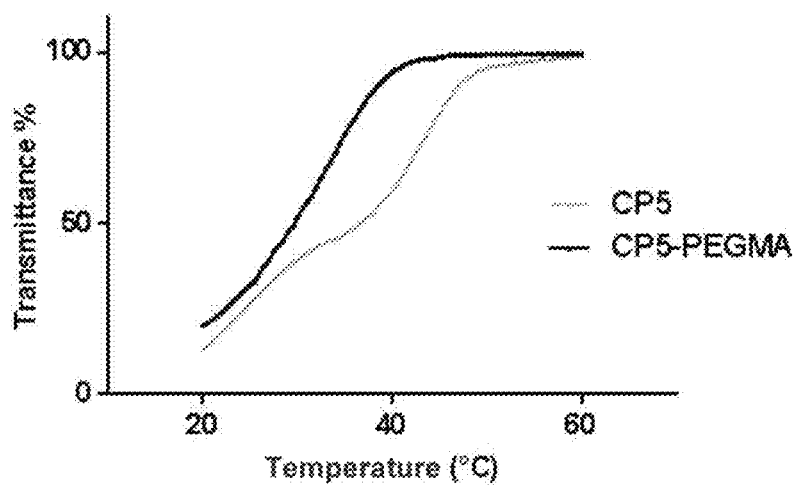
FIG. 2

A.
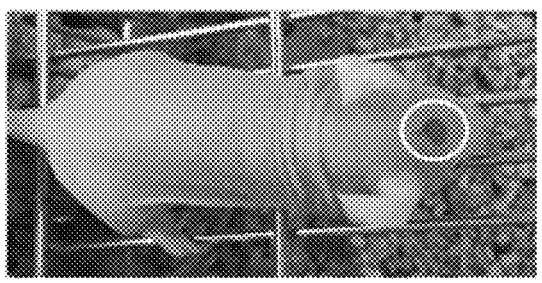 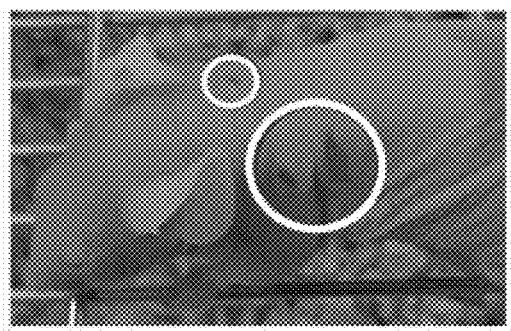
B.
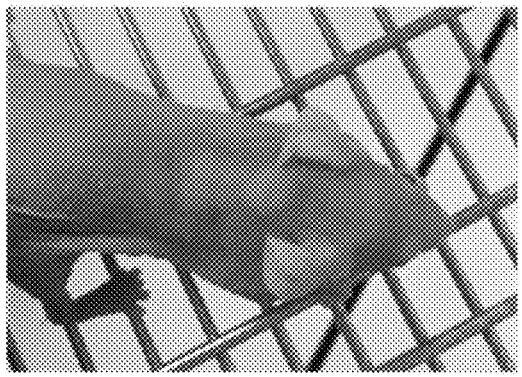 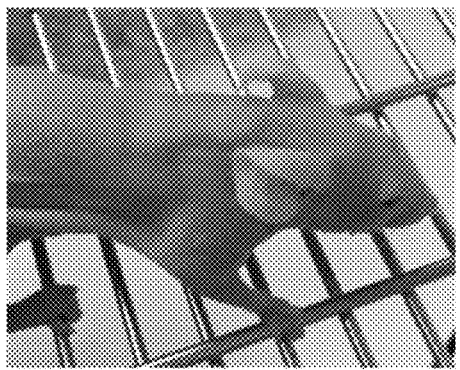
FIG.3

FIG.10 (beginning)

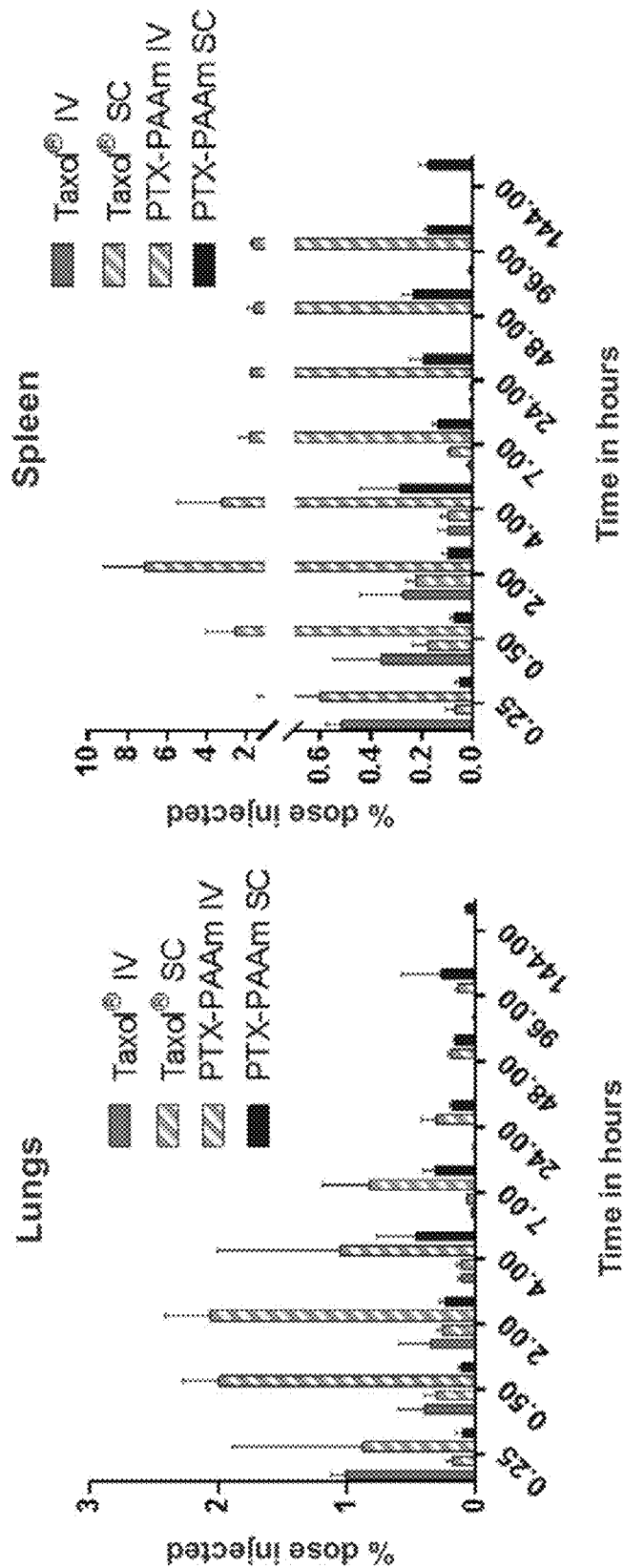
FIG.10 (continuation)

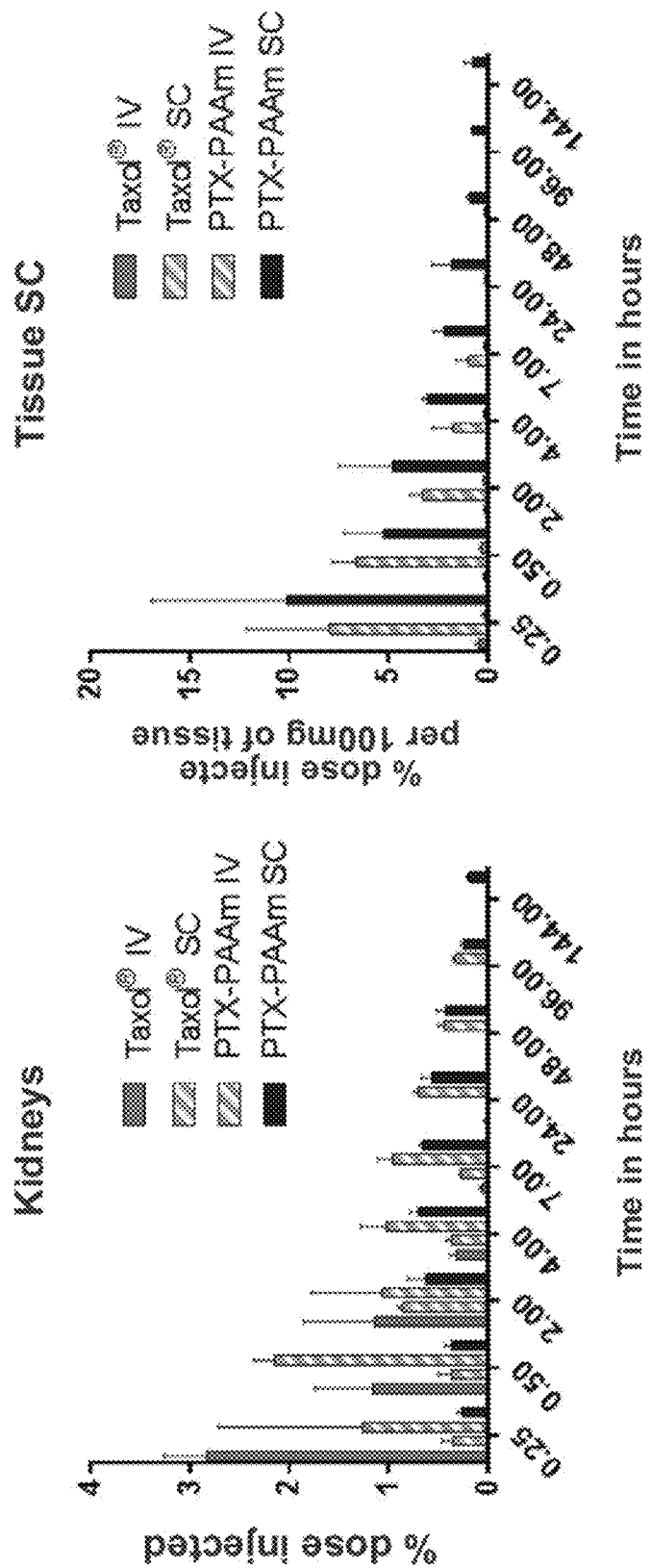
FIG.10 (conclusion)

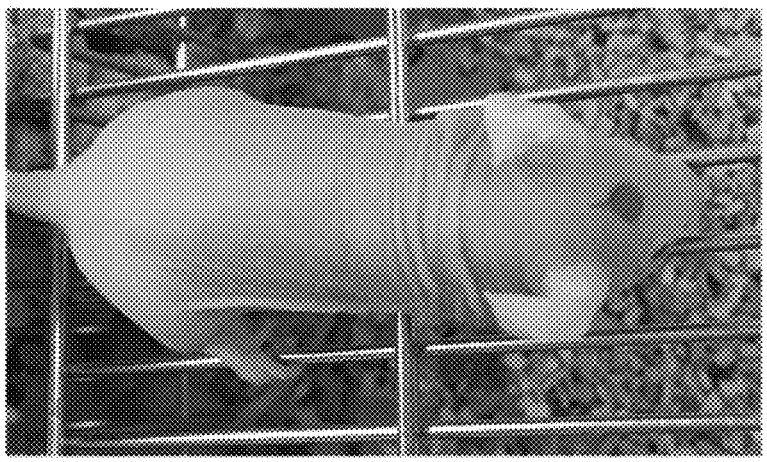
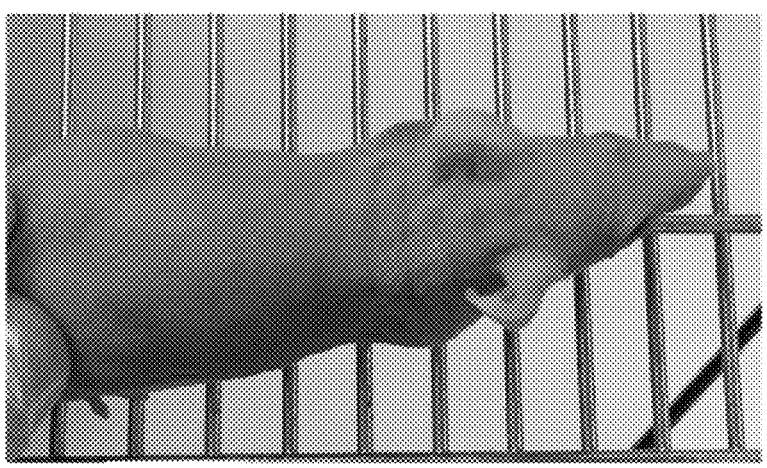
FIG.12

POLYMERIC PRODRUGS AND SUBCUTANEOUS AND/OR INTRAMUSCULAR ADMINISTRATION THEREOF

CROSS-REFERENCE TO RELATED APPLICATIONS

This is a National Stage of PCT international application PCT/EP2018/081636, filed on Nov. 16, 2018, which claims the priority of French Patent Application No. 17 60868 filed Nov. 17, 2017 and French Patent Application No. 17 60869 filed Nov. 17, 2017, each of which is incorporated herein by reference in its entirety.

FIELD OF THE INVENTION

The present invention relates to new prodrugs of active molecules. These prodrugs allow, in particular, the subcutaneous or intramuscular administration of active molecules, whose subcutaneous or intramuscular administration is problematic or impossible, in particular, because of toxicity at the injection site. The prodrugs of the invention comprise an active ingredient, covalently linked with a polymer chain, preferably a hydrophilic and/or heat-sensitive polymer chain.

STATE OF THE ART

To the knowledge of the inventors, during the development of formulations for subcutaneous (SC) or intramuscular (IM) injections three major parameters prevent their use: the bioavailability of the active ingredient (AI), the stability of the AI in the SC or IM formulation, and local reactions at the site of administration.

- AIs have low bioavailability by the SC route. Either their physico-chemical properties (logP, solubility, molar mass, etc.) do not allow them to cross the SC barrier, or they are not stable in biological medium and are degraded before reaching the circulation, and sometimes they even combine the two disadvantages;
- They induce serious local toxicity such as irritation or necrosis (irritant/vesicant effects) in the subcutaneous tissue. These reactions may have several sources such as the osmolarity of the solution, a vasoconstrictor effect of the AI, the mechanism of action or retention in the tissues;
- The low injection volumes inherent in SC administration are not compatible with current doses of chemotherapy. Usually, we may inject 2 ml by direct injection, and relatively larger volumes by slow injection (infusion, "insulin pump" type). These volumes will depend on the rate of absorption of the AI (up to 1 1/24 h for 5% glucose). It is therefore necessary to concentrate the AIs in solution. However, AIs are no longer stable in solution at high concentrations and will therefore crystallize or aggregate.

However, the subcutaneous (SC) route remains more attractive than the intravenous (IV) route because it is easier and faster to use. Self-administration by the patient at home may even be considered. However, in oncology, only 9 anticancer chemotherapies (methotrexate, cytarabine, azacitidine, cladribine, bleomycin, bortezomib, omacetaxine, rituximab, trastuzumab) are available by the SC route. Among them, we find few of the most effective and commonly prescribed AIs for the treatment of cancer.

Various actors are trying to solve the problems detailed above. For example, Otsuka (in collaboration with BMS) has developed a technology based on cyclodextrins. These cyclic oligosaccharides have a hydrophobic internal cavity and a hydrophilic outer surface. Therefore hydrophobic AIs will be encapsulated in the internal cavity, thus inducing an increase in their apparent solubility. This increase in solubility leads to an increase in SC bioavailability.

The Adocia company is developing bio-chaperone polymers which will associate with biomolecules such as insulin, through physico-chemical interactions. Insulin will be stabilized in individual ("monomeric") form and will have a higher SC bioavailability than insulin in its classic hexameric form (faster absorption of the "monomer" form because its molar mass is lower). So here we play on the stability of the insulin monomer at high concentration.

The company Halozyme is developing a formulation based on hyaluronidase; an enzyme made up mostly of hyaluronic acid that will reversibly degrade the SC tissue. The direct injection volume may, therefore, be increased from 2 to 5 ml.

Although all these formulations allow an improvement in SC administration by playing on bioavailability for Otsuka, stability for Adocia, or injection volume for Halozyme, they are only applicable to a limited number of molecules (respectively, neuroleptics, proteins (insulins) and monoclonal antibodies).

The limitations of the technologies currently available for the SC route are linked to the fact that they act on only one of the aforementioned parameters at a time (bioavailability and stability, injection volume) and none of them makes it possible to reduce the SC toxicities.

Thus, there is a need for technologies that allow subcutaneous or intramuscular administration of AI while avoiding the problems linked to its bioavailability and its stability, and, above all, not causing irritation/necrosis to the patient at the injection site.

Furthermore, the administration of a high concentration of AI to achieve effective therapeutic doses, for example from 5 mg/ml and in particular from 10 mg/ml, generally has the technical drawback that the formulation becomes too viscous and incompatible with SC injection.

OBJECTS OF THE INVENTION

The present invention aims to solve the technical problems stated above.

In particular, the present invention aims to solve the technical problem of providing an injectable composition in particular by the subcutaneous (SC) or intramuscular (IM) route of one or more active ingredients, for example anticancer active ingredients, while avoiding the problems of bioavailability and stability of the active ingredient, and not causing irritation, or even necrosis, to the patient at the injection site.

The present invention aims to solve the technical problem of providing an injectable composition, in particular by subcutaneous (SC) or intramuscular (IM) administration, with a high concentration of AI, and, in particular, concentrations 5 mg/ml, or even 10 mg/ml or more.

The present invention aims to solve the technical problem of providing an injectable composition, in particular by subcutaneous (SC) or intramuscular (IM) administration, of a therapeutically effective amount of at least one pharmaceutically active ingredient in a small volume of injectable solution, for example from 1 to 20 ml.

The present invention aims to solve the technical problem of providing an injectable composition, in particular by subcutaneous (SC) or intramuscular (IM) administration, of at least one pharmaceutically active ingredient formulated in a low viscosity solution that allows easy injection.

DESCRIPTION OF THE INVENTION

The inventors have developed a new polymeric prodrug technology that allows the administration of the active ingredients by the SC or IM route without any observed skin/local toxicity. It was surprisingly discovered that the prodrug approach makes it possible to deactivate the AI of interest at the level of the SC or IM tissue, and to release it by cleavage of the AI/polymer bond once it is in the general circulation or at the site of action. The chemical coupling between AIs and highly water-soluble polymers such as polyacrylamide also makes it possible to modify the physico-chemical properties of therapeutic molecules. The physico-chemical properties of the polymer will be conferred on the AI. Unlike other polymers used to form prodrugs (such as poly (ethylene glycol) and its derivatives), polyacrylamide can greatly increase the solubility of AI even when it has a low molar mass. These characteristics make it possible to maintain stability at high concentration, while limiting viscosity so as to maximize its absorption from SC or IM tissue, and to limit its metabolism to this level, thus leading to increased bioavailability. The fact of being able to modify the speed and rate of absorption, combined with the prodrug approach (where the AI is inactive until its release) makes it possible to suppress the local undesirable effects of necrotizing/irritant AIs. Once in the general circulation or at the site of action, the active ingredient is released from the prodrug by cleavage of the bond and it then regains its activity.

The technology developed by the inventors leads to the modification of the physico-chemical properties of the active ingredients. This allows their SC or IM administration in high concentration, while limiting the problems of irritation and necrosis. Advantageously, the polymeric prodrugs of the invention increase the bioavailability and the stability of the AI.

Advantageously, the polymeric prodrugs of the invention maintain stability at a high concentration of AI, and, in particular, at a concentration of at least 1 mg/ml, for example of at least 2 mg/ml, and preferably of at least 5 mg/ml in equivalent AI concentration. According to a variant, the polymeric prodrug is injectable at an equivalent concentration of AI of at least 10 mg/ml and preferably at least 20 mg/ml.

Advantageously, the polymeric prodrugs of the invention maximize the absorption of AI from the SC or IM tissue.

Advantageously, the polymeric prodrugs of the invention limit the metabolism of AI, thus leading to increased bioavailability.

Advantageously, the polymeric prodrugs of the invention allow SC injection of large doses of AI, while avoiding the phenomena of SC or IM irritation and/or necrosis.

Advantageously, the polymeric prodrugs of the invention make it possible to adapt to a large number of active ingredients, which makes the polymeric prodrugs, their preparation, and their uses particularly interesting.

Surprisingly, the inventors have identified polymeric prodrugs whose properties allow them to be administered by the SC or IM route without irritation or necrosis reactions.

The inventors have found that the physicochemical properties of the polymer are imparted to the prodrug, and, in particular, the properties of solubility in a solution for injection by the SC or IM route.

In fact, the use of polymeric prodrugs according to the present invention leads to obtaining solutions at equivalent concentrations of active ingredient, for example from 1 to more than 20 mg/ml in comparison with the low solubilities of certain active ingredients of around 1 µg/ml. The polymeric prodrugs of this invention were chosen for their high water solubility compared to a large number of polymers tested. As a result of their extremely hydrophilic nature, they will be able to dissolve hydrophobic AI while having a low molar mass. Due to this low molar mass, the charge rate will be high, the viscosity will be low, while absorption will be rapid at the level of the SC tissue (the absorption speed is inversely proportional to the molar mass). In addition, the choice of the bond between the polymer and the AI makes it possible to release the molecule only after absorption by the SC or IM tissue (no early release in the tissue). These three characteristics make it possible to inject large quantities of AI without toxicity. In addition, in vivo tests show the absence of manifestations of toxicity, irritation or necrosis following the SC administration of a cytotoxic in the form of a prodrug that usually leads to this type of reaction when injected without our formulation. The prodrugs used in the invention therefore show properties suitable for being administered by the SC or IM route.

SUMMARY OF THE INVENTION

The present invention relates to a polymeric prodrug comprising:
  a polymer chain formed at least in part by acrylamide monomer or one of its derivatives, such as for example N-hydroxyacrylamide, N-(4-hydroxybutyl) methacrylamide, N-(poly (ethylene glycol))-acrylamide, N-(3-methoxypropyl) methacrylamide, N-(2-(dimethylamino) ethyl)-N-methylmethacrylamide, N-(2-(diethylamino) ethyl)-N-methylmethacrylamide, said polymer comprising a proximal part and a terminal part;
  a first pharmaceutically active molecule covalently coupled to the proximal part of the polymer
  possibly a second pharmaceutically active molecule covalently coupled to the terminal part of the polymer.

The proximal and terminal parts are arbitrarily defined as the ends of an essentially linear polymer chain, i.e. the pendant chains, when present, are shorter in length than the main chain. In general, the main chain is the chain comprising the reactive groups for the polymerization, and which propagate during the polymerization. The proximal and terminal parts designate the ends of the polymer. Preferably, when the polymerization is directional, the proximal part designates the end which does not lengthen, while the terminal part designates the end which lengthens. The terms proximal and terminal "parts" generally and respectively designate the proximal and terminal ends, so that the proximal part may comprise the first AI and the first monomer, while the terminal part may comprise the last monomer and, when present, the second AI. The invention also speaks of proximal and terminal parts for the radical polymerization control agent.

The invention relates, in particular, to a polymeric prodrug comprising a proximal part and a terminal part and comprising:
  at least a first pharmaceutically active molecule,
  at least one polymer chain formed, at least in part, by acrylamide monomers or one of its derivatives, at least one radical polymerization control agent comprising a proximal part and a terminal part;
the first pharmaceutically active molecule being located in the proximal part of the prodrug polymer and covalently linked to the proximal part of the radical polymerization control agent, while the terminal part of the radical polymerization control agent is located in the terminal part of the prodrug polymer, and is covalently linked to the polymer chain.

The invention also relates to a water-soluble polymeric prodrug, comprising a proximal part and a terminal part and comprising:
at least one first pharmaceutically active molecule
at least one polymer chain
at least one radical polymerization control agent comprising a proximal part and a terminal part;
the first pharmaceutically active molecule being located in the proximal part of the prodrug polymer and covalently linked to the proximal part of the radical polymerization control agent,
the terminal part of the radical polymerization control agent being located in the terminal part of the prodrug polymer and being covalently linked to the polymer chain, said solubility being appreciated at a concentration of 200 mg/ml in distilled water with paclitaxel as the first pharmaceutically active molecule.

According to a variant, the polymer is formed at least in part by an acrylamide monomer or one of its derivatives, and by co-monomers to form random or block polymers, such as, for example, poly (acrylamide-co-acrylonitrile).

According to a specific variant, the polymer is a poly (acrylamide).

The present invention relates to a polymeric prodrug comprising:
a water-soluble polymer chain, said polymer comprising a proximal part and a terminal part;
a first pharmaceutically active molecule, covalently coupled to the proximal of the polymer;
possibly, a second pharmaceutically active molecule covalently coupled to the terminal part of the polymer;
said solubility being appreciated at a concentration of 200 mg/ml in distilled water with paclitaxel as the first pharmaceutically active molecule.

According to a variant, the polymer chain has a polydispersity index less than 1.5, said polydispersity index determined by steric exclusion chromatography.

According to a variant, the polymer chain has a molar mass of 1000 to 1,000,000 g/mol, preferably less than 100,000 g/mol, more preferably less than 50,000 g/mol.

Advantageously, the polymer comprises a radical polymerization control agent chosen from among the following radical polymerization control agents: Reversible Addition-Fragmentation Chain Transfer (RAFT), Atom Transfer Radical Polymerization (ATRP) and its derivatives (Copper (I) Mediated Radical Polymerization), Nitroxide-Mediated Polymerization (NMP), Cobalt Mediated Radical Polymerization (CoMRP), Organotellurium Mediated Living Radical Polymerization (TERP) and Organostibines Mediated Radical Polymerization (SBRP), and, for example, from among thiocarbonylthio transfer agents such as dithiocarbonate, xanthate, dithiocarbamate and trithiocarbonate, from among complexes based on transition metals (Cu, Fe, Ru, etc.), from among alkoxyamines, from among cobalt-based and organotellurium-based complexes, and from among organoantimoines.

According to a variant, the polymer may comprise a radical polymerization control agent comprising, in the terminal part, a terminal alkyl chain, for example comprising from 1 to carbon atoms, a carboxylic acid function, an alcohol function, an amine function, an amide function, a thiol function, said function being possibly supported by the terminal alkyl chain, and said function being possibly linked to a second pharmaceutically active molecule.

According to a variant, the polymer may comprise a radical polymerization control agent comprising, in the proximal part, a proximal function chosen from an amide, ester, carbonate, carbamate, succinate, disulfide, acetal, thioether, triazole function; and/or diglycolate, succinate, succinimidyl 4-(N-maleimidomethyl) cyclohexane-1-carboxylate (SMCC), glycinate, glucuronate, valine-citrulline, maleimide linker, said function and/or proximal linker forming a covalent bond with the first pharmaceutically active ingredient.

According to a variant, the active molecule is an anticancer molecule, an antibiotic molecule (bacterio/fungo-static, bacterio/fungo-toxic or antiviral agent), an antidiabetic molecule, a molecule treating vascular or cardiovascular pathologies, a molecule treating pathologies of the central nervous system, an anti-inflammatory molecule, an agonist molecule of a physiological receptor, an antagonist or partially antagonist molecule of a physiological receptor, an immunomodulatory molecule.

According to a variant, the active molecule may be an anticancer molecule chosen from, paclitaxel, docetaxel, gemcitabine, cladribine, capecitabine, daunorubicin, doxorubicin, epirubicin, idarubicin, actinomycin, amsacrine, dacarbazine, dactinomycin, vincristine, vimblastine, vindesine, methotrexate, colchiccine, cyclophosphamide, 6-mercaptopurine, azathioprine, lomustine, carmustine, dacarbazine, cisoroatin, tenoposide or etoposide, fotemustine, mitomycin C, mitoxantrone, streptozocin, trabectedin, vinflunine, vinorelbine, asernic trioxide, bendamustine, busulfan, cabazitaxel, carboplatin, eribulin, irinotecan, topotecan, ixabepilone, nelarabine, oxaliplatin, pralatrexate, temozolomide, pemetrexed, imatinib, sunitinib, and sorafenib.

Advantageously, the polymeric prodrug induces a release of the pharmaceutically active molecule spread over time into the blood circulation or at the site of action, and, for example, at the level of a tumor or at the intracellular level.

The present invention relates to a polymeric prodrug according to the invention and its use in a method of therapeutic treatment, or in a method of diagnosis, or in a method of medical imaging, in a human or animal, by subcutaneous or intramuscular administration.

The present invention relates to a polymeric prodrug according to the invention and its use in a method of therapeutic treatment of a human or animal by subcutaneous or intramuscular administration, said polymeric prodrug comprising a covalent bond between a pharmaceutically active molecule and a polymer, said pharmaceutically active molecule not being administered by the subcutaneous or intramuscular route due to its toxicity at the injection site (irritation/necrosis of the tissue) when it is not linked by covalent bond to said polymer, preferably said polymeric prodrug having a bioavailability of the molecule preventing local toxicities (at the injection site), and releasing the pharmaceutically active molecule into the blood circulation.

According to a variant, the method of treatment according to the invention may be a method of treating cancer.

The present invention relates to a controlled radical polymerization method, in particular by the method known as the initiator active ingredient, of at least one polymeric prodrug according to the invention, said method comprising the steps:

covalent coupling of at least one first pharmaceutically active molecule with a radical polymerization control agent comprising a proximal part and a terminal part, to form a first coupled molecule;

controlled radical polymerization of the first coupled molecule in the presence of acrylamide monomers or one of its derivatives, to form the polymeric prodrug;

possibly, the covalent coupling of a second pharmaceutically active molecule in the terminal part of the control agent, after controlled radical polymerization of the polymer.

The present invention also relates to a method for controlled radical polymerization of at least one polymeric prodrug according to the invention, said method comprising the steps of:

controlled radical polymerization of a polymer in the presence of acrylamide monomer or one of its derivatives to form a polymer comprising a proximal part and a terminal part;

covalent coupling of at least one first pharmaceutically active molecule with the proximal part of the polymer to form said polymeric prodrug;

possibly, the covalent coupling of a second pharmaceutically active molecule in the terminal part of the polymeric prodrug.

The present invention also relates to a medicament comprising at least one polymeric prodrug according to the invention.

The present invention also relates to a composition injectable into the tissue of a mammal, preferably a human, and, in particular, formulated for an injection by the subcutaneous or intramuscular route, said composition comprising a polymeric prodrug as defined according to the invention.

The present invention relates to a polymeric prodrug for use in a treatment method. This method comprises the subcutaneous or intramuscular administration of a pharmaceutically effective amount of said polymeric prodrug to a patient.

Definitions

In the present invention, the terms below are defined as follows:

"Polymer" refers to a polymer or a copolymer.

The term "radical polymerization initiator" refers to all of the compounds used to produce radicals and thus initiate radical polymerization. These compounds have a chemical function capable of releasing radicals under the action of heat, of irradiation of light, by oxidation-reduction reaction, ionizing radiation, electrochemical reactions and sonication. Non-limiting examples of initiators include compounds of the azo type, such as 2,2'-azobis (2-methylpropionitrile), 4,4'-azobis (4-cyanovaleric acid), 1,1'-azobis (cyclohexanecarbonitrile); of the inorganic peroxide type; or of the organic peroxide type such as benzoyl peroxide, lauroyl peroxide, methyl ethyl ketone peroxide, and tert-butyl peroxybenzoate.

The term "control agent" refers to all of the compounds used during a polymerization reaction in order to obtain polymers having a ratio of number average molar mass to weight average molar mass, or dispersity, less than 1.5. The nature of these compounds depends on the implementation of the controlled radical polymerization technique. For controlled polymerization by Reversible Addition-Fragmentation Chain Transfer (RAFT), these are dithiocarbonate (xanthate), trithiocarbonate, dithioester or dithiocarbamate compounds. For Nitroxide-Mediated Polymerization (NMP), the radical polymerization initiator and the control agent are combined in a single molecule of the alkoxyamine type. For Atom Transfer Radical Polymerization (ATRP), the radical polymerization initiator is an alkyl halide, while the control agent is a halogen atom involved in a reaction of oxidation-reduction orchestrated by a complex type catalyst based on transition metal.

The method of the "initiator active ingredient" implies a controlled radical polymerization technique using a control agent modified by chemical coupling with an active ingredient. Thus, the modified control agent carries an active ingredient molecule, while the polymer obtained also carries an active ingredient in the proximal part of each polymer chain.

"Alkyl" means any linear or branched saturated hydrocarbon chain, from 1 to 20 carbon atoms, preferably from 1 to 6 carbon atoms, such as, for example, methyl, ethyl, n-propyl, isopropyl, n-butyl, sec-butyl, isobutyl, tert-butyl, pentyl and its isomers (e.g. n-pentyl, isopentyl), hexyl and its isomers (e.g. n-hexyl, iso-hexyl).

The term "arylalkyl" refers to an alkyl group substituted by an aryl group and may be written: aryl-alkyl-.

The term "aryl" refers to a polyunsaturated aromatic hydrocarbyl group having a single ring (for example, phenyl) or several fused aromatic rings (for example, naphthyl) or covalently linked, typically containing 5 to 12 carbon atoms; preferably 6 to 10, in which at least one ring is aromatic. The aromatic ring may possibly include one to two additional rings (either cycloalkyl, heterocyclyl or heteroaryl) fused therewith. Non-limiting examples of aryl groups include phenyl, biphenylyl, biphenylenyl, 5 or 6 tetralinyl, naphthalene-1- or -2-yl, 4, 5, 6 or 7-indenyl, 1-, 2-, 3-, 4- or 5-acenaphthylenyl, 3-, 4- or 5-acenaphthenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

The term "approximately", placed before a number, means plus or minus 10% of the nominal value of this number.

"Pharmaceutically acceptable excipient" refers to an inert vehicle or support used as a solvent or diluent in which the pharmaceutically active agent is formulated and/or administered, and which does not produce an undesirable, allergic or other reaction when it is administered to an animal, preferably a human. This includes all solvents, dispersing media, coatings, antibacterial and antifungal agents, isotonic agents, absorption retardants, surfactants such as surfactant polymers, lipids and the like. The choice of pharmaceutically acceptable excipients may be made by those skilled in the art depending on the properties of the nature and the properties of the pharmaceutically active agent, the subject to be treated, and the administration route. For human administration, preparations must meet standards of sterility, general safety and purity, as required by regulatory authorities, such as, for example, the FDA or EMA.

"Pharmaceutically or therapeutically effective amount" relates to the necessary and sufficient amount of a pharmaceutical or therapeutic agent to be administered to a subject allowing the slowing or stopping of the progression, the aggravation, or the deterioration of at least one of the symptoms of an illness. This amount may help relieve symptoms of a disease or cure it.

"Pharmaceutical" refers to a compound or active ingredient in the health field, having, for example, properties that are therapeutic and/or useful for a therapeutic diagnosis, in particular for the purposes of treatment (curative and/or symptomatic and/or prophylactic), of a disease, or for therapeutic research. The pharmaceutical term thus groups together therapeutic molecules or active ingredients, as well as those of diagnosis.

"Aqueous medium" refers to a medium based on water molecules ($H_2O$), in particular an aqueous solution. Preferably, an aqueous medium comprises between 50% and 100% of water, by mass relative to the total mass of the medium. An aqueous medium may, in particular, be a biological fluid such as blood, lymph, saliva or urine.

"Active molecule" and "active ingredient" are synonymous and refer to a compound for therapeutic use relating to health. In particular, an active molecule may be indicated to treat or prevent a disease, preferably in a subject. This is called a pharmaceutically active molecule. Within the meaning of the present invention, the term "treatment of a disease" designates the reduction or attenuation of at least one undesirable effect or symptom of a disease, disorder or condition associated with an impairment of a function of an organ, tissue or cell. For the purposes of the present invention, the expression "preventing a disease" or "inhibiting the development of a disease" refers to the fact of preventing or avoiding the appearance of symptoms. By active ingredient is meant a compound having, in particular, therapeutic and/or useful properties for a therapeutic diagnosis, in particular for the purposes of the treatment (curative and/or symptomatic and/or prophylactic) of a disease, or for therapeutic research.

"Prodrug": The term "prodrug" refers to pharmacologically acceptable derivatives of active molecule compounds, such as, for example, amides or esters, the biotransformation product of which generates the biologically active molecule in vivo. Prodrugs are generally characterized by an increase in bioavailability and are easily metabolized to biologically active compounds in vivo. Preferably, a prodrug is a water-soluble polymer covalently linked with an active molecule.

"Polymeric prodrug": This term refers to the polymer conjugated to at least one active ingredient.

"Subject" refers to an animal, including a human. Within the meaning of the present invention, a subject may be a patient, i.e. a person receiving medical care, undergoing or having undergone medical treatment, or being monitored in the context of the development of a disease. In one embodiment the subject is treated for the first time. In another embodiment, the subject is resistant to another type of treatment, and is treated with the prodrugs of the present invention as part of a second, third or fourth intention.

"Upper Critical Solution Temperature (UCST)" refers to the critical temperature above which a thermosensitive polymer is completely soluble.

"Thermosensitive" refers to a property of a polymer whose physical properties change abruptly as a function of temperature. In the invention, the property concerned is the solubility of the polymer in an aqueous medium. Preferably, a heat-sensitive polymer has a Upper Critical Solution Temperature (UCST).

DETAILED DESCRIPTION OF THE INVENTION

Polymer

Advantageously, the polymeric prodrugs according to the invention are obtained by polymerization of a monomer or of co-monomers.

Advantageously, the polymeric prodrugs according to the invention are obtained by controlled radical polymerization.

Thus, the dispersity of the prodrug-polymer so formed is very low.

Advantageously, the polymeric prodrug according to the invention comprises an active molecule covalently linked with a hydrophilic polymer chain by the initiator active ingredient method. Advantageously, the AI is coupled to a polymerization control agent before the polymerization according to the method known as the initiator active ingredient method. In this method the AI is covalently coupled to a polymerization control agent. Once this coupling has been effected, it is possible to grow a vinyl polymer in a controlled manner from this adduct control agent/AI. The AI will eventually end up covalently coupled to the proximal end of the polymer. Unlike other methods of synthesis of polymeric prodrugs (in particular that consisting of a coupling between the AI and a preformed polymer, referred to as post-functionalization, or that coupling the AI to the monomer before polymerization), this technique makes it possible to position an AI at one end of each polymer chain. The resulting polymeric prodrugs have a well-defined structure, a high charge rate and simple purification. It is easily transposable to a large number of AIs and polymers.

According to one aspect, the polymeric prodrug according to the invention comprises an active molecule covalently linked with a chain of water-soluble polymer by the initiator active ingredient method.

Thus, advantageously, the controlled radical polymerization of the acrylamide monomers is carried out in the presence of the first molecule coupled to the chain transfer agent to form the polymeric prodrug. According to one embodiment, it is possible to polymerize in the presence of acrylamide monomers and co-monomers.

Alternatively, the polymeric prodrug may be composed of polyacrylamide, hydrophilic polyacrylamide derivatives, or a polyacrylamide copolymer such as poly (acrylamide-co-acrylonitrile).

Advantageously, the polymer according to the invention comprises a polyacrylamide structure whose repeating unit has the formula [—CH2-CH (CONH2)-]$_n$, where n represents the number of repeating units in the polymer (or copolymer).

According to one embodiment, it is possible to polymerize in the presence of derivatives of acrylamide monomers. For example, acrylamide derivatives such as N-hydroxyacrylamide, N-(4-hydroxybutyl) methacrylamide, N-(poly (ethylene glycol))-acrylamide, N-(3-methoxypropyl) methacrylamide, N-(2-(dimethylamino) ethyl)-N-methylmethacrylamide, N-(2-(diethylamino) ethyl)-N-methylmethacrylamide.

The procedure or method according to the invention advantageously makes it possible to provide a polymeric prodrug having a pharmaceutically active molecule (or AI) at one end of the prodrug-polymer molecule, and thus advantageously makes it possible to control the AI charge rate. In general, such control is not present in prior art techniques in which the AI is coupled either after polymerization, or with the monomer before polymerization. These techniques result in a variable number of AI per polymer chain and complex purification of the uncoupled AI.

According to one embodiment, a second pharmaceutically active molecule is coupled by covalent coupling to the terminal part of the control agent. This coupling takes place after the end of the radical polymerization.

Polymer Chain

Advantageously, the choice of the polymer and its size makes it possible to obtain the polymeric prodrugs which may be administered by the SC or IM route.

Advantageously, the size of the polymeric prodrugs is controlled by the radical polymerization conditions.

In one embodiment, the polymeric prodrug comprises an active molecule, covalently linked with a polyacrylamide chain by the initiator active ingredient method.

In one embodiment, the polymeric prodrug comprises an active molecule, covalently linked with a copolymer and obtained from acrylamide monomers and from one or more other comonomers.

In one embodiment, the polymeric prodrug comprises an active molecule, covalently linked with a copolymer and obtained from acrylamide and acrylonitrile monomers by the initiator active ingredient method, so as to obtain the poly (acrylamide-co-acrylonitrile) polymeric prodrug that is thermosensitive at UCST.

In one embodiment, the polymeric prodrug comprises an active molecule, covalently linked with a polymer by the method of the initiator active ingredient or copolymer obtained from hydrophilic monomers derived from acrylamide such as N-hydroxyacrylamide, N-(4-hydroxybutyl) methacrylamide, N-(poly (ethylene glycol))-acrylamide, N-(3-methoxypropyl) methacrylamide, N-(2-(dimethylamino) ethyl)-N-methylmethacrylamide, N-(2-(diethylamino) ethyl)-N-methylmethacrylamide.

According to one embodiment, it is possible to polymerize in the presence of other hydrophilic monomers.

According to one embodiment, the copolymer according to the invention is a random copolymer.

In another embodiment, the copolymer according to the invention is a statistical copolymer.

Preferably, the polymer of the polymeric prodrug according to the invention is not crosslinked.

Typically, the polymeric prodrug according to the invention does not form a crosslinked hydrogel.

Advantageously, a molar mass significantly greater than that of the active molecule improves the maintenance of the properties linked to the interactions between the polymer and the solvent, and, in particular, improves the solubility in aqueous phase of the active molecule.

As a result, in one embodiment the polymer of the invention has a molecular weight of 1,000 to 100,000 g/mol. In a particular embodiment, the polymer of the invention has a molecular weight of 2,000 to 70,000 g/mol, from 5,000 to 70,000 g/mol, from 5,000 to 60,000 g/mol, from 5,000 to 50,000 g/mol, from 5,000 to 40,000 g/mol, from 5,000 to 30,000 g/mol, from 5,000 to 40,000 g/mol, from 10,000 to 40,000 g/mol, from 15,000 to 40,000 g/mol, from 15,000 to 30,000 g/mol or from 20,000 to 30,000 g/mol.

According to a variant, the molar mass of the polymer (only the polymer part) is from 1,000 to 80,000 g/mol.

Advantageously, the terminal part of the polymeric prodrug varies the solubility and/or the viscosity of the polymeric prodrug.

According to one embodiment, the polymer chain, for example of polyacrylamide, comprises an alkyl terminal chain, for example comprising from 2 to 20 carbon atoms or a halogen —SH, —COOH, —NH$_2$ function. Advantageously, the length of the alkyl chain or its nature makes it possible to vary the viscosity of the polymeric prodrug.

According to a variant, the polymeric prodrug is thermosensitive, having a Higher Critical Solution Temperature (UCST) of 0 to 60° C. in an aqueous medium. The polymeric prodrug comprises an active molecule which is covalently linked with a thermosensitive polymer chain of poly (acrylamide-co-acrylonitrile).

So far, to the knowledge of the inventors, no one has described polymers having a UCST, grafted onto active molecules by the initiator active ingredient method. Those skilled in the art would expect an alteration in the thermosensitive character due to the chemical modification of the polymer by the active molecule.

The inventors have demonstrated that the covalent association of an active molecule with a polymer chain presenting a UCST has little effect on the thermosensitive nature of said polymer. Surprisingly, it is possible, once the active molecule has been conjugated, to modify the molar mass and the monomer composition in order to find a polymer with thermosensitive properties. Consequently, the coupling of the active molecule with an optimized polymer allows the preservation of the thermosensitive character of the polymer which always presents a UCST.

According to one embodiment, the poly (acrylamide-co-acrylonitrile) chain of these polymeric prodrugs has a molar mass of 1,000 to 100,000 g/mol.

According to one embodiment, the molar percentage of acrylonitrile is more than 0 to 100%, preferably 1 to 50%, and more preferably 5 to 35% relative to the number of moles of the polymer.

Active Molecule

Typically, the pharmaceutically active molecule to be used for the preparation of the polymeric prodrugs of the invention is a free molecule or a molecule linked with another molecule. According to one embodiment, the active molecule for the preparation of the polymeric prodrugs of the invention is free.

In general, the pharmaceutically active molecule to be used for the preparation of the polymeric prodrugs of the invention has a function capable of reacting with a controlled radical polymerization agent according to the invention, so as to couple the active molecule (or AI) and the polymerization agent by covalent bond.

According to one embodiment, the pharmaceutically active molecule to be used for the preparation of the polymeric prodrugs according to the invention is a molecule having at least one free function (capable of reacting with a controlled radical polymerization agent), for example chosen from the functions: —OH, —NH$_2$, —NH, —NHR (R=alkyl as defined), —SH, —COOH, —C═O, —CHO or halogen. In one embodiment, the free function is a nucleophilic function.

The pharmaceutically active molecule can not carry free functions. It may be chemically treated before it is coupled to the polymerization agent so that it has a free function (capable of reacting with the controlled radical polymerization agent). Several approaches are known in the prior art for functionalizing an active molecule. An indicative and non-limiting example for the present invention consists in the treatment of an active molecule with hyperoxides leading to the hydroxylation of the active molecule.

According to one embodiment, the free nucleophilic function of the active molecule is selected from the groups —OH, —NH$_2$, —NHR and —SH. Preferably, the nucleophilic function is —OH or —NH$_2$.

For example, in order to better control the grafting of the polymer chain on the active molecule, i.e. the other nucleophilic functions of the molecule, if any are present, may or may not be protected.

According to a first embodiment, the nucleophilic functions of the active molecule which do not participate in the controlled radical polymerization, are not protected.

According to a second embodiment, the nucleophilic functions of the active molecule which do not participate in controlled radical polymerization are protected by groups known in the prior art, for example tert-butoxycarbonyl chloride, di-tert-butyl dicarbonate, azide or amides of tert-butoxycarbonyl, tert-butyl (dimethyl) silyl chloride, tosyl chloride, alkyls, aryls, alkylaryls, esters, ethers, silylated ethers.

As indicated by the examples, the invention may be implemented independently of the polarity of the active molecule. Consequently, the active molecule to be used in the polymers of the invention is a polar, amphiphilic or apolar molecule. According to a first embodiment, the active molecule to be used in the polymers of the invention is a polar molecule. According to a second embodiment, the active molecule to be used in the polymers of the invention is an apolar molecule. According to a third embodiment, the active molecule to be used in the polymers of the invention is an amphiphilic molecule.

According to a variant, the charge rate is 0.1 to 20% (mass of the AI relative to the total mass of the prodrug-polymer molecule).

In one embodiment, the active molecule is chosen from a group of active molecules comprising:
- anti-cancer molecules,
- anti-biotic molecules (bacterio/fungo-static, bacterio/fungo-toxic, or antiviral agents),
- anti-diabetic molecules,
- molecules treating vascular and cardiovascular pathologies,
- molecules treating pathologies of the central nervous system
- anti-inflammatory molecules,
- physiological receptor agonist molecules,
- antagonistic or partially antagonistic molecules of physiological receptors,
- immunomodulatory molecules.

In one embodiment, the active molecule is an anti-cancer molecule chosen from, mercapaclitaxel, docetaxel, gemcitabine, cladribine, capecitabine, daunorubicin, doxorubicin, epirubicin, idarubicin, actinomycin, amsacrine, dacarbazine, dactinomycin, vincristine, vimblastine, vindesine, methotrexate, colchiccine, cyclophosphamide, azathioprine, 6-mercaptopurine, lomustine, carmustine, dacarbazine, cisplatin, fluorouracil, teniposide or etoposide, fotemustine, mitomycin C, mitoxantrone, streptozocin, trabectedin, vinflunine, vinorelbine, asernal trioxide, bendamustine, busulfan, cabazitaxel, carboplatin, eribulin, irinotecan, topotecan, ixabepilone, nelarabine, oxaliplatin, pralatrexate, temozolomide, pemetrexed, imatinib, sunitinib, sorafenib.

In one embodiment, the active molecule is chosen from anti-cancer molecules (paclitaxel, gemcitabine), from peptides (cyclic RGD) and/or fluorescent probes (rhodamine and Cyanine 5.5).

In one embodiment, the active molecule is an anti-cancer molecule chosen from, paclitaxel or gemcitabine. According to one embodiment, the prodrugs of the invention comprise paclitaxel as the active molecule. In one embodiment, the first active molecule is paclitaxel.

In one embodiment, the first active molecule is gemcitabine.

According to one embodiment, a polymeric prodrug according to the invention comprises an active molecule at one end.

According to one embodiment, a polymeric prodrug according to the invention comprises an active molecule at its proximal end.

According to one embodiment, a polymeric prodrug according to the invention comprises an active molecule at its terminal end.

According to one embodiment, a polymeric prodrug according to the invention comprises two active molecules, one at each end.

Polymerization

The present invention relates to molecules onto which a polymer chain, in particular as described above, is grafted.

Advantageously, the polymerization according to the invention is carried out by a controlled radical route.

Advantageously, the polymerization according to the invention is carried out by a radical route controlled by the initiator active ingredient method.

Thus, the polymer chain is grafted onto the active molecule by applying a controlled radical polymerization method. In one embodiment, the polymeric prodrug of the invention is obtained by a controlled radical polymerization method chosen from among:
- polymerization controlled by Reversible Addition-Fragmentation Chain Transfer (RAFT),
- radical polymerization controlled by Nitroxide-Mediated Polymerization (NMP),
- radical polymerization controlled by Atom Transfer Radical Polymerization (ATRP),
- radical polymerization controlled by Single Electron Transfer-Living Radical Polymerization (SET-LRP),
- radical polymerization controlled by cobalt,
- radical polymerization controlled by organotellates, or
- radical polymerization controlled by organostilbine.

Typically, the polymeric prodrug further comprises a chain transfer agent.

In one embodiment, the polymeric prodrug is synthesized by radical polymerization controlled by Reversible Addition-Fragmentation Chain Transfer (RAFT).

In one embodiment, the polymeric prodrugs according to the invention are obtained by controlled radical polymerization of the type controlled by Reversible Addition-Fragmentation Chain Transfer (RAFT), by reacting at least one monomer, an initiator of radical polymerization and a controlled radical polymerization agent (also called chain transfer agent) onto which is coupled the pharmaceutically active molecule.

In particular, a polymeric prodrug according to the invention is prepared by controlled radical polymerization and comprises, according to one variant, the covalent coupling of at least one first pharmaceutically active molecule with a radical polymerization control agent comprising a proximal part and a terminal part, so as to form a first coupled molecule.

The radical polymerization control agent comprises a proximal part and a terminal part because, during the polymerization, the polymerization control agent (or chain transfer agent) is cleaved with a part, referred to here as proximal, which remains linked to the AI which is positioned at the start of the polymer chain, and a part, referred to here as terminal, which is fixed at the end of the polymer chain so as to complete it. This polymerization control agent makes it possible to precisely and advantageously control the length of the polymer chain.

According to one variant, we refer to the first coupled molecule to designate the AI coupled to the polymerization control agent, or to the proximal part of the control agent. In one embodiment, the polymer of the prodrug according to the invention further comprises a RAFT-type chain transfer agent chosen from among:

trithiocarbonates such as 3,5-bis (2-dodecylthiocarbono-thioylthio-1-oxopropoxy) benzic, 3-butenyl 2-(dodecylthiocarbonothioylthio)-2-methylpropionate, 2-(2-carboxyethylsulfanylthiocarbonylsulfanyl)-proprionic acid, 4-((((2-carboxyethyl) thio) carbonothioyl) thio)-4-cyanopentanoic acid, 2-cyanobutan-2-yl 4-chloro-3, 5-dimethyl-1H-pyrazole-1-carbodithioate, 2-cyanobutanyl-2-yl 3,5-dimethyl-1H-pyrazole-1-carbodithioate, 4-cyano-4-[(dodecylsulfanylthiocarbonyl) sulfanyl] pentanoic acid, 2-(butylthiocarbonothioylthio) propanoic acid, 4-cyano-4-(ethylcarbonothioylthio) pentanoic acid, 4-cyano-4-[(dodecylsulfanylthiocarbonyl) sulfanyl] pentanol, cyanomethyl (3,5-Dimethyl-1H-pyrazole)-carbodithioate, cyanomethyl dodecyl trithiocarbonate, cyanomethyl [3-(trimethoxysilyl) propyl] trithiocarbonate, 2-cyano-2-propyl dodecyl trithiocarbonate, S,S-dibenzyl trithiocarbonate, 2-(dodecyl-thiocarbonothioylthio)-2-methylpropionic acid, 2-(dodecyl-thiocarbonothioyl-thio)-2-methylpropionic acid, 3-azido-1-propanol ester, 2-(dodecylthiocarbonothioyl-thio)-2-methylpropionic acid, N-hydroxysuccinimide ester of 4-cyano-4-[(dodecylsulfanylthiocarbonyl) sulfanyl] pentanoic acid, pentafluorophenyl ester of 2-(dodecylthiocarbonothioylthio)-2-methylpropionic acid, 2-(dodecylthiocarbonothioylthio) propionic acid, methyl 2-(dodecyl)-2-methylpropionate, pentaerythritol tetrakis [2-(dodecylthiocarbonothioylthio)-2-methylpropionate], phthalimidomethyl butyl trithiocarbonate, poly (acrylic acid) having a 2-(dodecylthiocarbonothioylthio)-2-methylpropionic acid end, glycol) bis [2-(dodecylthiocarbonothioyl-thio)-2-methylpropionate], poly (ethylene poly (ethylene glycol) methyl ether 4-cyano-4-[(dodecylsulfanyl-thiocarbonyl) sulfanyl] pentanoate, poly (ethylene glycol) methyl ether (4-cyano-4-pentanoate dodecyl trithiocarbonate), poly (ethylene glycol) methyl ether (4-cyano-4-pentanoate dodecyl trithiocarbonate), poly (ethylene glycol) methyl ether (4-cyano-4-pentanoate dodecyl trithiocarbonate), poly (ethylene 2-(dodecylthiocarbonothioylthio)-2-methylpropionate, glycol) methyl ether poly (ethylene glycol) methyl ether 2-(dodecylthiocarbonothioylthio)-2-methylpropionate, poly (ethylene glycol) methyl ether (2-methyl-2-propionic acid dodecyl trithiocarbonate) L-lactide) 4-cyano-4-[(dodecylsulfanyl-thiocarbonyl) sulfanyl] pentonate, poly (L-lactide) 4-cyano-4-[(dodecylsulfanyl-thiocarbonyl) sulfanyl] pentonate, poly (D,L-lactide), 4-cyano-4-[(dodecylsulfanyl-thiocarbonyl) sulfanyl] pentonate, polystyrene with an end of 2-(dodecylthiocarbonothioylthio)-2-methylpropionic acid. or 1,1,1-tris [(dodecylthiocarbonothioylthio)-2-methylpropionate] ethane;

dithiocarbamates such as benzyl 1H-pyrrole-1-carbodithioate, cyanomethyl diphenylcarbamodithioate, cyanomethyl methyl (phenyl) carbamodithioate, cyanomethyl methyl (4-pyridyl) carbamodithioate, 2-cyanopropan-2-yl N-methyl-(pyridin-4-yl) carbamodithioate, methyl 2-[methyl (4-pyridinyl) carbamothio-ylthio] propionate, 1-succinimidyl-4-cyano-4-[N-methyl-N-(4-pyridyl) carbamothioylthio] pentanoate;

dithioabenzoates such as benzyl benzodithioate, cyanomethyl benzodithioate, 4-cyano-4-(phenylcarbonothioyl-thio) pentanoic acid, N-succinimidyl ester of 4-cyano-4-(phenylcarbonothioylthio) pentanoic acid, 2-cyano-2-propyl benzodithioate, 2-cyano-2-propyl4-cyanobenzodithioate, ethyl 2-(4-methoxyphenylcarbonothioylthio) acetate, ethyl 2-methyl-2-(phenylthiocarbonylthio) propionate, ethyl 2-(phenylcarbonothioylthio)-2-phenylacetate, ethyl 2-(phenylcarbonothioylthio) propionate, 1-(methoxy-carbonyl) ethyl benzodithioate, 2-(4-methoxyphenyl-carbonothioylthio) ethanoic acid, 2-nitro-5-(2-propy-nyloxy) benzyl 4-cyano-4-(phenylcarbonothioylthio) pentanoate, 2-(phenylcarbonothioylthio) propanoic acid, or 2-phenyl-2-propyl benzodithioate;

switchable RAFT agents such as cyanomethyl methyl (4-pyridyl) carbamodithioate, 2-cyanopropan-2-yl N-methyl-N-(pyridin-4-yl) carbamodithioate, methyl 2-[methyl (4-pyridinyl) carbamothioylthio] propionate, or 1-succinimidyl-4-cyano-4-[N-methyl-N-(4-pyridyl) carbamothioylthio] pentanoate.

The chain transfer agent is, for example, chosen from: 4-cyano-4-[(dodecylsulfanylthiocarbonyl) sulfanyl] pentanoic acid, 2-(dodecylthiocarbonothioylthio)-2-methylpropionic acid, 4-cyano-acid 4-(phenylcarbonothioylthio) pentanoic acid, 2-(2-carboxyethylsulfanylthiocarbonylsulfanyl) propionic acid, 2-(butylthiocarbonothioylthio) propanoic acid, 4-cyano-4-(ethylcarbonothioylthio) pentanoic acid, benzodithioate 2-cyanopropan 2-yl, or 2-cyano-2-propyl dodecyle trithiocarbonate. The conventional radical initiator is chosen from among: 2,2'-azobis (2-methylpropionitrile), 1,1'-azobis (cyclohexanecarbonitrile), 4,4'-azobis (4-cyanovaleric) acid, 2,2'-azobis (2-methylbutyronitrile), benzoyl peroxide, lauroyl peroxide, methyl ethyl ketone peroxide, tert-butyl peroxybenzoate.

In one embodiment, the chain transfer agent is chosen from among: 4-cyano-4-[(dodecylsulfanylthiocarbonyl) sulfanyl] pentanoic acid, 2-(dodecylthiocarbonothioylthio)-2-methylpropionic acid, 4-cyano-4-(phenylcarbonothioylthio) pentanoic acid 2-(2-carboxyethylsulfanylthiocarbonylsulfanyl) propionic acid, 2-(butylthiocarbonothioylthio) propanoic acid, 4-cyano-4-(ethylcarbonothioylthio) pentanoic acid, benzodithioate of 2-cyanopropan-2-yl, or 2-cyano-2-propyl dodecyle trithiocarbonate.

In one embodiment, the chain transfer agent is chosen from among:
4-cyano-4-[(dodecylsulfanylthiocarbonyl) sulfanyl] pentanoic acid, 2-(butylthiocarbonothioylthio) propanoic acid, 4-cyano-4-(ethylcarbonothioylthio) pentanoic acid, N-hydroxysuccinimide ester 4-cyano-4-[(dodecylsulfanylthiocarbonyl) sulfanyl] pentanoic acid.

In one embodiment, the chain transfer agent is 4-cyano-4-[(dodecylsulfanylthiocarbonyl) sulfanyl] pentanoic acid (CDP).

In one embodiment, the transfer agent is directly linked to the active molecule. However, during radical polymerization, the transfer agent, by virtue of its polymerization control function, is split into two parts, one proximal which remains linked to the active ingredient and the other which reacts with the terminal part of the growing polymer.

According to a variant, the transfer agent is covalently linked to the pharmaceutically active molecule by an ester, amide, carbonate, carbamate, acetal, disulfide, thioether, triazole 4-(N-maleimidomethyl) cyclohexane-1-function;

diglycolate, succinate, succinimidyl carboxylate (SMCC), glycinate, glucuronate, valine-citrulline, maleimide linker, said function and/or proximal linker forming a covalent bond with the first active pharmaceutical ingredient.

In another embodiment, the transfer agent is previously functionalized with an oligomer of a hydroxy carboxylic acid. According to this embodiment, this oligomer chain which is located after grafting between the active molecule and the transfer agent, makes it possible to control the rate of release of the active molecule from the polymeric prodrug of the invention. According to one embodiment, the oligomer is a dimer, preferably diglycolic acid.

In addition, a radical polymerization initiator is necessary because it allows the initiation of the polymerization and thus makes the polymer chain grow from the active molecule functionalized by the RAFT agent. The initiator may be of the azo type such as 2,2'-azobis (2-methylpropionitrile), 1,1'-azobis (cyclohexanecarbonitrile), 4,4'-azobis (4-cyanovaleric) acid, 2,2'-azobis (2-methylbutyronitrile); inorganic peroxide type; or organic peroxide type such as benzoyl peroxide, lauroyl peroxide, methyl ethyl ketone peroxide, tert-butyl peroxybenzoate. In one particular embodiment, the free radical initiator is 2,2'-azobis (2-methylpropionitrile), CAS number: 78-67-1.

Block Polymer

In one embodiment, the polymeric prodrug according to the invention is a polymeric prodrug whose active molecule is covalently linked with a block copolymer. The latter comprises the polymer or copolymer as described above, and an extension with at least one hydrophilic polymer. In fact, the presence of the transfer agent at the end of the polymer or copolymer chain allows the addition of an additional polymer chain. The copolymer of the invention may comprise at least two blocks.

According to one embodiment, the prodrug according to the invention comprises a polymer, the chain of which further comprises an extension of its chain with an additional polymer, preferably the additional polymer being a water-soluble polymer. In one embodiment, the water-soluble polymer is chosen from poly [oligo (ethylene glycol) methyl ether methacrylate], poly [oligo (ethylene glycol) methyl ether acrylate], poly [oligo (ethylene glycol) methacrylate], polyacrylamide, glycopolymers (synthesized from methacrylate, acrylate, acrylamide vinyl ether or styrenic type monomers bearing a sugar function), poly (N,N-dimethyl acrylamide), polystyrene sulfonate, poly (N-vinyl pyrrolidone), hydrophilic polypeptides and polysaccharides.

In one embodiment, the water-soluble polymer is polyacrylamide.

Method

In a second aspect, the invention refers to the method for the preparation of the polymer, as described above.

Method for Obtaining the Polymer

Those skilled in the art may choose the suitable polymerization technique from those known in the prior art as a function of the physicochemical properties of the active molecule and of the structural and physicochemical characteristics desired for the polymer.

According to one embodiment, the method comprises at least one step of polymerization from the active molecule.

According to this embodiment, the method for preparing a polymer according to the invention comprises the steps of:
i) coupling an active compound, with a chain transfer agent as described above,
ii) polymerization of the monomer(s) as described above, from the active molecule.

According to one embodiment, the method comprises at least one step of controlled radical polymerization from the active molecule.

The controlled radical polymerization may be chosen from techniques known in the prior art such as:
polymerization controlled by Reversible Addition-Fragmentation chain Transfer (RAFT),
radical polymerization controlled by Nitroxide Mediated Polymerization (NMP),
radical polymerization controlled by Atom Transfer Radical Polymerization (ATRP),
radical polymerization controlled by Single Electron Transfer-Living Radical Polymerization (SET-LRP)
radical polymerization controlled by cobalt,
radical polymerization controlled by organotellates, or
radical polymerization controlled by organostilbine.

In one embodiment, the method for preparing the polymeric prodrug according to the invention comprises at least one RAFT polymerization step.

According to this embodiment, the method for preparing a polymer according to the invention comprises the steps of:
i) coupling an active compound with a chain transfer agent as described above,
ii) polymerization of the monomer(s) as described above, from the transfer agent.

For controlled radical polymerization, such as RAFT polymerization, step (ii) is carried out in the presence of a radical polymerization initiator (free radical generator). The polymerization initiator allows the initiation of polymerization, and thus increases the polymer chain from the active molecule functionalized by the RAFT agent. The initiator may be of the azo type such as 2,2'-azobis (2-methylpropionitrile), 1,1'-azobis (cyclohexanecarbonitrile), 4,4'-azobis (4-cyanovaleric) acid, 2,2'-azobis (2-methylbutyronitrile); of the inorganic peroxide type; or of the organic peroxide type such as benzoyl peroxide, lauroyl peroxide, methyl ethyl ketone peroxide, tert-butyl peroxybenzoate.

In one particular embodiment, the free radical initiator is 2,2'-azobis (2-methylpropionitrile), CAS No.: 78-67-1.

In one embodiment, step (ii) is carried out at room temperature. In another embodiment, step (ii) is carried out at a temperature of 25° C. to 150° C.

Telechelic Polymeric Prodrugs

The present invention offers the advantage of providing a platform which may be applied to a wide variety of active ingredients, imaging and/or targeting agents. A functional group at each end of a polymer chain may be used to chemically link the molecule of interest, thus making it possible to manufacture mono- or bi-functional systems called telechelic polymers. It is possible to design a large number of systems ranging from the simplest system (a molecule grafted at one end of the polymer chain) to more complex systems called heterobifunctional, where we may have a pharmaceutically active molecule at one end, and an imaging agent or targeting ligand at the other end of the polymer. Furthermore, various polymeric prodrugs with various active ingredients may also be synthesized and then formulated together to produce combined therapies.

This type of telechelic polymers of macromolecular architecture is particularly interesting because it makes it possible to create polymeric prodrugs with different properties and applicable to many fields. Heterobifunctional polymers are more particularly interesting because they allow two different functionalities to be combined in the same compound. These polymeric prodrugs according to the invention are therefore particularly suitable for biomedical applications, where it will be possible to combine on the same chain two types of molecules which may be pharmaceutically/biologically active for different purposes, for example:

For a targeted delivery of active ingredient, by combining an active ingredient and a targeting ligand (e.g. antibody, ligand, peptide, etc.)

For imaging, by combining a targeting ligand and a tracing molecule such as a fluorophore. These polymeric prodrugs may, for example, be used for detection and imaging in the case of cancer, using specific markers for tumor cells.

Many techniques exist for synthesizing these heterobifunctional polymers. According to one variant, the method for preparing telechelic polymeric prodrugs comprises one or more pre or post polymerization modifications to couple the different molecules of interest.

According to a variant, a polymeric prodrug comprising a first active ingredient is covalently bonded to a peptide, typically a peptide coupling.

For example, the following synthetic principle may be used to carry out a bioconjugation between a peptide of interest and a polyacrylamide polymer terminated by the RAFT agent:

active molecule. According to a different embodiment, the compositions may comprise polymeric prodrugs comprising various active molecules and the same polymer chain. This allows us to have two active molecules with a different pharmacodynamic profile in the same formulation. According to another embodiment, the compositions may comprise polymeric prodrugs comprising active molecules and different polymer chains. This makes it possible to have, in the same formulation, two active molecules with a different pharmacodynamic profile and whose release is adapted as a function of these physicochemical properties.

In a third embodiment, the compositions may comprise at least one polymeric prodrug according to the invention and at least one free active molecule, wherein their pharmaceutically acceptable salts or prodrugs are as known in the prior art. By free active molecule is meant an unbound molecule, or, at the very least, a molecule that is not covalently linked with the polymer.

Formulations

The present invention relates to compositions in the form of an aqueous solution comprising an aqueous medium and at least one polymeric prodrug according to the invention.

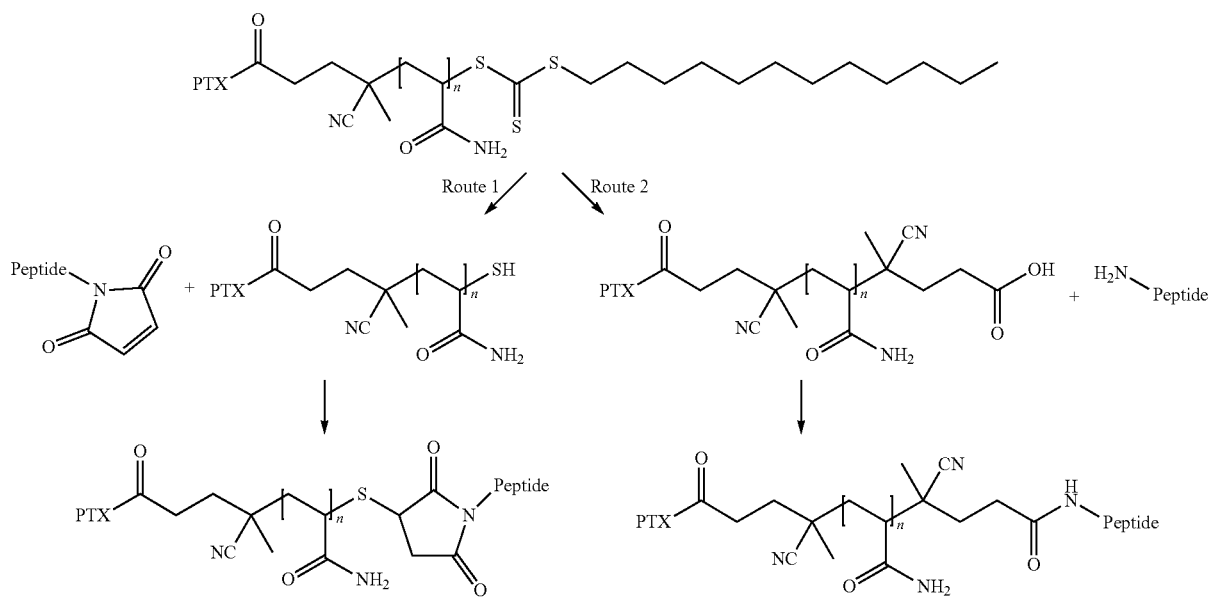

The first route (route 1) makes it possible to associate the peptide with the polymer via a maleimide type linker via a thiol-maleimide coupling, while the second (route 2) allows the coupling to be carried out directly by the formation of a peptide bond via a peptide coupling.

According to a variant, the polymerization may be initiated by the peptide, after which the coupling with the active ingredient is carried out after polymerization.

The invention relates to a composition comprising at least one polymeric prodrug according to the invention.

In a first embodiment, the compositions comprise a single polymeric prodrug according to the invention.

In a second embodiment, the compositions comprise at least two, at least three, at least four, or at least five polymeric prodrugs according to the invention. According to this embodiment, the compositions comprise polymeric prodrugs comprising the same active molecule. The presence of polymeric prodrugs with different polymer chains allows bi-modal, tri-modal or pluri-modal release of the Advantageously, the polymeric prodrug according to the invention is soluble in an aqueous medium.

Typically, the polymeric prodrug according to the invention is soluble in distilled water of at least 100 mg/ml, preferably 150 mg/ml, and more preferably at 200 mg/ml.

Preferably, the solubility of the polymeric prodrug is tested according to the following method:

The various polymeric prodrugs are dissolved in an equivalent concentration (200 mg/ml) and then centrifuged for 30 min at 16,783 g. The insolubility is observed by the appearance of a whitish or colored deposit in the bottom of the Eppendorf.

Advantageously, the solution comprising the polymeric prodrug according to the invention is not very viscous.

Advantageously, the viscosity of the solution of the polymeric prodrug may be modulated as a function of the size and of the nature/composition of the polymer. Controlled radical polymerization here also presents an important technical advantage of the invention.

Advantageously, the polymeric prodrug according to the invention makes it possible to concentrate the AI without significantly increasing the viscosity of the formulation, which makes it possible to limit the quantities (in particular by volume) of the injected formulation.

Advantageously, a polymeric prodrug according to the invention may be formulated in injectable form.

Advantageously, the polymeric prodrug according to the invention is formulated in an easily injectable aqueous solution.

For example, the viscosity of the solution comprising a polymeric prodrug according to the invention allows its injection via a 26 G needle. Advantageously, the solution comprising a polymeric prodrug according to the invention requires an injection force of less than 30 N through a 26 G needle. Preferably, the solution comprising a polymeric prodrug according to the invention is injectable through a 26 G needle at a concentration of at least 50 mg/ml, for example at least 100 mg/ml, and preferably at least 125 mg/ml. Alternatively, the solution comprising a polymeric prodrug according to the invention may be injected through a 26 G needle at a concentration of at least 150 mg/ml, and preferably at least 200 mg/ml.

Preferably, we test the injectability (or syringability) (expressed in Newton as a function of the concentration) according to the following method:

The syringability/injectability of polymer solutions is estimated using custom-made equipment as described by Burckbuchler et al. (Eur. J. Pharm. Biopharm., 76, 2010, 351-356) coupled to a texture analyzer (TA.XT Plus Texture Analyzer, Stable Micro Systems) having a force sensor of 30 kg. 400 µL of each solution is withdrawn and then injected through a 1 ml syringe (MeritMedical, Medaillon® Syringe) and a 26G×½" needle (Terumo Neolus, 0.45×12 mm) at a speed of 1 mm/s. The injection force is measured at the rate of 25 measurements per second.

Uses

Advantageously, at least certain physicochemical properties of the polymer are imparted to the AI. In particular, the polymer makes it possible to increase the solubility of the AI, so as to maintain stability at high concentration, to maximize its absorption, and to limit its metabolization, thus leading to increased bioavailability.

The present invention relates, in particular, to a polymeric prodrug for use in a method of therapeutic treatment. The method comprises administering a therapeutically effective amount of the polymeric prodrug to a patient.

Advantageously, the prodrug approach (where the AI is inactive until its release) makes it possible to suppress the local undesirable effects of necrotizing/irritant AIs. Typically, once in the general circulation, the active ingredient is released from the polymer by cleavage of the bond and then regains its activity. The cleavage is obtained due to the biological conditions present in the blood circulation. Once in the general circulation, the active ingredient is released from the prodrug by cleavage of the bond and then regains its activity.

Typically, the polymeric prodrug is injected into a tissue (by the SC or IM route in particular) and passes into the bloodstream. The polymeric prodrug is then cleaved to release the AI of interest into the bloodstream.

Advantageously, the control of the nature of the monomer, of the size and of the dispersity of the polymer, of the nature of the polymerization control agent, and of the bond between it and the AI, makes it possible to modify the speed and the rate of absorption, coupled with the prodrug (where the AI is inactive until its release), and makes it possible to suppress the local undesirable effects of necrotizing/irritant AIs.

The polymeric prodrugs of the invention and their compositions may have several applications in the biomedical field.

According to a variant, the AI designates an active molecule linked to a targeting agent making it possible to target a specific area to be treated and, for example, to direct the active molecules released towards their site of action.

According to a variant, the AI designates an active molecule linked to a diagnostic agent allowing the imaging of a specific area to be treated.

According to a variant, the AI designates a targeting agent linked to a diagnostic agent making it possible to target the AI towards the tissue or cells to be treated.

The invention also refers to a medicament comprising at least one polymeric prodrug according to the invention.

The invention also relates to the use of the polymeric prodrug according to the invention for the prevention and/or treatment of a disease, in particular of a human or animal.

The invention also relates to the use of at least one prodrug according to the invention for the preparation of a medicament.

Typically, the medicament comprises at least one polymeric prodrug according to the invention in a therapeutically effective amount. According to one embodiment, the medicament further comprises pharmaceutically acceptable excipients. These excipients correspond to the standards of the European Pharmacopoeia or the FDA.

Those skilled in the art determine a drug formulation as a function of the disease to be prevented and/or treated, the route of administration of the medicament, and the nature of the active molecule. In one embodiment, the formulations are injectable formulations.

According to this embodiment, the administration is by bolus or continuous (infusion), preferably the administration is by bolus. According to this embodiment, the formulations are injectable formulations for administration:
  subcutaneously,
  intramuscularly,
  intratumorally,
  intradermally, or
  intravenously,
  preferably subcutaneously or intramuscularly.

Preferably, a polymeric prodrug according to the invention is administered (or administrable) by the subcutaneous or intramuscular route.

Methods

The invention also refers to a polymeric prodrug for use in a method of therapeutic treatment. This method comprises administering a therapeutically effective amount of at least one polymeric prodrug according to the invention to a subject, in particular a human or animal.

The treatment methods may relate to the treatment of diseases as described above.

In a particular embodiment, the method of treatment is a method of treating cancer.

The administration of at least one polymeric prodrug according to the invention may be simultaneous with the administration of other active molecules, formulated according to the invention or not.

The administration of at least one polymeric prodrug according to the invention may be sequential to the administration of other active molecules, formulated according to the invention or not.

In one embodiment, these formulations make it possible to increase the bioavailability of the active ingredient and are administered by the subcutaneous, intramuscular, intratumoral or intradermal route, preferably by the subcutaneous or intramuscular route.

Given the versatility of the invention which makes it possible to couple several types of active molecules to a polymer chain, the diseases which may be prevented or treated with the medicament according to the invention are not limited to cancers, bacterial infections, viral infections, fungal infections, parasitic infections, inflammatory diseases, metabolic diseases, micro-vascular diseases, macro-vascular diseases, cardiovascular diseases, pulmonary diseases, endocrine diseases or diseases of the central nervous system.

According to the invention, the type of cancers which may be treated by the administration of a polymeric prodrug according to the invention are not particularly limited since the treatment depends on the grafted active molecule. The active molecule grafted onto the polymer being chosen as a function of its biological, pharmacodynamic and pharmacokinetic properties in relation to the cancer to be treated.

In one embodiment, the cancer treated may be a solid cancer such as breast cancer, liver cancer, melanoma, cancer of the ovaries or endometrium, prostate and/or bladder, stomach, intestines, Kaposi's sarcoma, brain cancer, bone cancer, pancreatic cancer or lung cancer.

In another embodiment, the cancer is a cancer of the blood cells such as leukemia.

According to one embodiment, the active molecule is released quickly, for example 80% by weight of the active molecule may be released in less than 24 hours.

According to one embodiment, the active molecule may be released slowly, for example 50% by weight of the active molecule is released over more than 72 hours.

BRIEF DESCRIPTION OF THE FIGURES

FIG. 2 at top, shows transmittance vs. temperature curves showing the UCST behavior of the CP5-PEGMA and CP7-PEGMA particles at a polymer concentration equal to 4.5 mg/ml. The bottom of FIG. 2 shows the comparative curve of UCST behaviors of CP5 and CP5-PEGMA obtained after PEGylation and formulation of CP5.

FIG. 3 (top (A)) shows the local toxicity effects of subcutaneous administration of a solution of paclitaxel in PBS. FIG. 3 (bottom (B)), shows the absence of local toxicity following subcutaneous administration of a solution of paclitaxel formulated as a prodrug according to the invention PTX-P (AAm-co-AN) with 20% of AN.

FIG. 10: Pharmacokinetics and biodistribution of radiolabelled PTX in the commercial formulation of Taxol®, or in the form of PTX-PAAm administered at the rate of 7 mg/kg equivalent of PTX (0.14 mg of total PTX per mouse) intravenously and subcutaneously. The results for PTX-PAAm take into account free PTX plus PTX coupled with PAAm.

FIG. 12 (top) shows the local toxicity effects of subcutaneous administration of a solution of paclitaxel in PBS. FIG. 12 (bottom) shows the absence of local toxicity following the subcutaneous administration of a paclitaxel solution formulated as a prodrug according to the invention PTX-PAAm.

EXAMPLES

Figure 1:
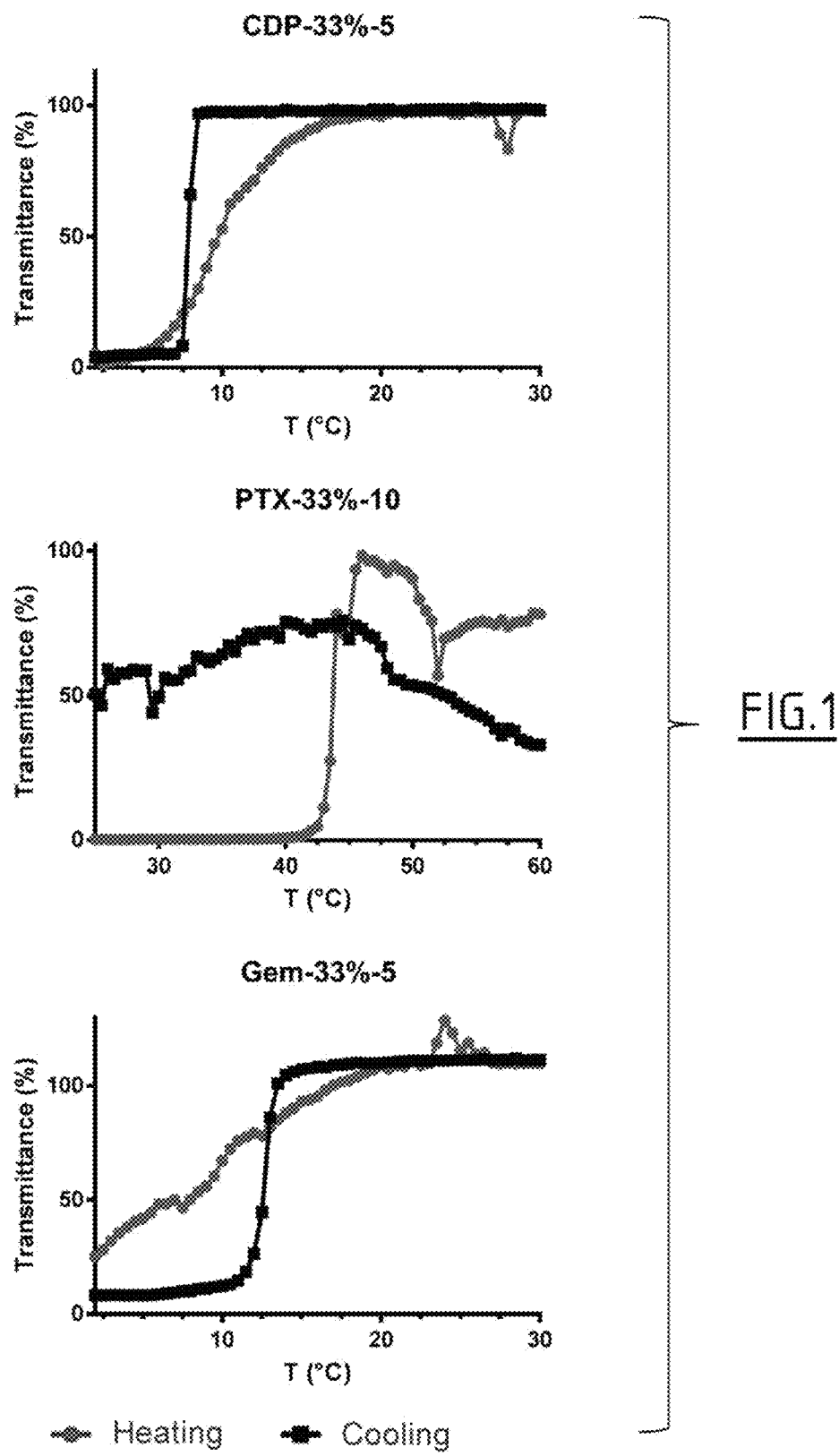
FIG. 1 shows three spectra of transmittance as a function of the temperature of 3 copolymers according to the invention having different RAFT agents: CDP-33%-5, PTX-CDP-33%-10, and Gem-33%-5. Acquisition at 4.5 mg/ml in PBS, at 600 nm, and at a temperature increase rate of 0.5° C./min.

The present invention will be better understood upon reading the following examples which illustrate the invention without limitation.

Abbreviations

AAm: designates acrylamide-CAS No. 79-06-1
AIBN: designates the radical initiator Azobisisobutyronitrile-CAS No. 78-67-1
AN: designates acrylonitrile-CAS No. 107-13-1
CDP: designates the RAFT control agent 4-cyano-4-[(dodecylsulfanylthiocarbonyl) sulfanyl] pentanoic acid-CAS No. 870196-80-8
CDP-ol: designates the RAFT functionalizing agent 4-cyano-4-[(dodecylsulfanylthiocarbonyl) sulfanyl] pentanol-CAS No. 1394136-26-5
Flash chromatography: designates a preparative separation method. The mobile phase crosses the stationary phase by applying a pressure of 10 to 20 psi
DCM: designates anhydrous dichloromethane-CAS No. 75-09-2
DMAI: designates 4-Dimethylaminopyridine-CAS No. 1122-58-3
DMF: designates N, N-Dimethylformamide-CAS No. 200-679-5
DMSO: designates Dimethylsulfoxide-CAS No. 67-68-5
EDC-HCl: designates 1-ethyl-3-(3-dimethylaminopropyl) carbodiimide hydrochloride-CAS No. 25952-53-8
EtOAC: designates ethyl acetate-CAS No. 7487-88-9
Gem: designates Gemcitabine hydrochloride-CAS No. 122111-03-9
GemTBDMS: designates Gemcitabine whose alcohol functions are protected by tert-Butyldimethylsilyl
H: designates hours
NHS: designates N-hydroxysuccinimide-CAS No. 6066-82-6
PEGMA: designates poly (ethylene glycol) methyl ether methacrylate, average Mn 300 g/mol-CAS No. 26915-72-0
PTX-A %-B: designates the polymer of paclitaxel-CDP-Poly (AAm-co-AN) with a molecular weight of B kg/mol and comprising A % of acrylonitrile relative to the moles of the polymer.

PTX-A %-B-PEGMA-C: designates the polymer of paclitaxel-CDP-Poly (AAm-co-AN) with a molecular weight of B kg/mol and comprising A % of acrylonitrile and C % of PEGMA relative to moles of the polymer PTX: designates paclitaxel-CAS No. 33069-62-4

Brine: designates a saturated aqueous solution of sodium chloride

TBAF: designates tetra-n-butylammonium fluoride-CAS No. 429-41-4

TBDMS: designates the tert-Butyldimethylsilyl radical

TBDMSCI: designates tert-Butyldimethylsilyl chloride-CAS No. 18162-48-6

THF: designates tetrahydrofuran-CAS No. 109-99-9

Material and Methods

Equipment

All reagents were supplied by Sigma Aldrich except the free radical initiator AIBN which was supplied by Acros. The acrylamide (AAm) and AIBN were recrystallized from chloroform and absolute ethanol, respectively. The acrylonitrile (AN) was purified on a basic alumina column to remove the monomethyl ether of hydroquinone. As for the other chemical reagents, they were used as received.

Methods

NMR

Proton nuclear magnetic resonance (NMR) spectroscopy. The $^1$H NMR analysis of small molecules was done using a Brucker Avance 300 to 300 MHz spectrometer in $CDCl_3$. All the $^1$H NMR analyses of the polymer samples were carried out using a Bruker Avance 3 HD 400 spectrometer at 400 MHz and at a temperature of 70° C. in do-DMSO.

UCST Transition Measurement

UV-visible spectroscopy: For the transmittance measurements of aqueous solutions of polymers at a fixed concentration of 4.5 mg/ml, the absorption spectra were recorded on a Perkin-Elmer Lambda 25 UV-visible spectrophotometer by making a ramp temperature rise and fall from 20 to 60° C. at a speed of 0.5° C./min thanks to a Peltier effect system.

Viscosity/Syringability Measurements

Viscosity is measured using syringability studies as a function of concentration. The syringability of polymer solutions has been estimated using custom-made equipment (Burckbuchler et al., Eur. J. Pharm. Biopharm., 76, 2010, 351-356) coupled with a texture analyzer (TA.XT Plus Texture Analyzer, Stable Micro Systems) with a 30 kg force sensor. 400 µl of each solution is withdrawn and then injected through a 1 ml syringe (MeritMedical, Medaillon® Syringe) and a 26G×½" needle (Terumo Neolus, 0.45×12 mm) at a speed of 1 mm/s. The injection force is measured at the rate of 25 measurements per second. Each sample is injected 3 times in a row. By this method, we consider that a solution is difficult to inject if the force required for injection exceeds 30 N.

Example 1: Coupling of Paclitaxel (PTX) to the Control Agent 4-cyano-4-[(dodecylsulfanylthiocarbonyl) sulfanyl] pentanoic (CDP)

The following example presents the chemical modification of the CDP control agent so that it is linked to a PTX molecule by an ester bond; the illustration below corresponds to the chemical structure of the synthesized product:

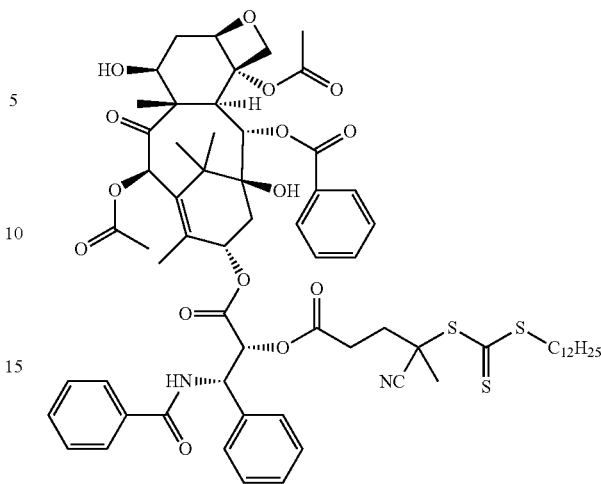

770 mg (1.80 mmol) of CDP, 231 mg (1.90 mmol) of DMAI, and 362 mg (1.90 mmol) of EDC·HCl are dissolved in a flask fitted with a magnetic bar with 5 ml of Anhydrous DCM, and mixed under argon at room temperature using a magnetic stirrer. After 15 min, a solution of 557 mg (0.66 mmol) of PTX in 2 ml of anhydrous DCM is added dropwise. The reaction mixture is brought to 30° C. After 12 h of stirring, a solution of 160 mg (0.83 mmol) of EDC·HCl and 120 mg (1.00 mmol) of DMAI in 1 ml of anhydrous DCM is added, then the reaction mixture is left to stir for another 12 hours at 30° C. The organic phase is washed with an aqueous $NaHCO_3$ solution and dried over $Na_2SO_4$ before evaporation of the solvent. The product is purified by chromatography on silica gel with a DCM/EtOAc gradient (16% to 50%). A sticky yellow powder is isolated with a yield of 65%, $^1$H NMR (300 MHZ, $CDCl_3$) δ8.17 (d, J=7.6 Hz, 2H), 7.78 (d, J=7.5 Hz, 2H), 7.72-7.31 (m, 15H), 6.93 (d, J=8.9 Hz, 1H), 6.54-6.15 (m, 2H), 6.01 (d, J=8.9 Hz, 1H), 5.70 (d, J=7.0 Hz, 1H), 5.51 (d, J=3.2 Hz, 1H), 5.00 (d, J=8.7 Hz, 1H), 4.47 (s, 1H), 4.28 (dd, J=34.7, 8.5 Hz, 2H), 3.84 (d, J=6.8 Hz, 1H), 3.34 (t, J=9.4 Hz, 1H), 2.51 (d, J=13.8 Hz, 6H), 2.25 (s, 3H), 1.96 (s, 2H), 1.83 (d, J=3.1 Hz, 3H), 1.78-1.60 (m, 10H), 1.38-1.13 (m, 20H), 0.90 (t, J=6.5 Hz, 3H). $^{13}$C NMR (75 MHZ, $CDCl_3$) δ216.76, 203.76, 171.19, 170.69, 169.81, 167.88, 167.03, 142.63, 136.75, 133.68, 133.47, 132.88, 132.04, 130.23, 129.18, 128.74, 128.60, 127.15, 126.51, 118.97, 84.45, 81.08, 79.14, 76.43, 75.59, 75.11, 74.65, 72.13, 72.00, 58.53, 52.79, 46.26, 45.60, 43.18, 37.13, 35.54, 33.61, 31.90, 29.61, 29.53, 29.42, 29.33, 29.07, 28.94, 27.66, 26.82, 24.81, 24.75, 22.74, 22.68, 22.10, 20.82, 14.83, 14.12, 9.61.

This species corresponds to paclitaxel covalently coupled to the CDP control agent called PTX-CDP in the following examples.

Example 2: Polymerization of Acrylamide by the Initiator Active Ingredient Method with PTX-CDP as a Control Agent This example presents the production of a paclitaxel-polyacrylamide polymeric prodrug by RAFT type polymerization of acrylamide in the presence of PTX-CDP, the following illustration corresponds to the chemical structure of the synthesized polymeric prodrug:

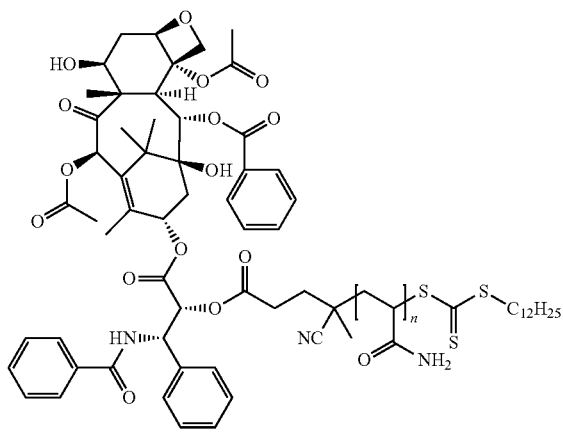

0.8 mg (0.005 mmol) of AIBN, 30 mg (0.024 mmol) of PTX-CDP, 454 mg (6.39 mmol) of AAm and 1.76 g (1.6 ml) of DMSO are introduced in a 7 ml straight bottle with a magnetic bar. The flask is sealed with a septum and the reaction mixture is bubbled with argon for 15 min. The reaction mixture is introduced into an oil bath previously heated to 70° C., and the reaction runs for 24 h with stirring. The polymer is then precipitated twice in an excess of cold methanol before being dissolved in DMSO and dialyzed in water using a 3.5 kD Spectra/Por 3 dialysis rod for three days. The solution is then lyophilized for 24 h in order to obtain a yellowish solid. $M_n$ 21.600, $M_w/M_n$ 1.12.

Example 3: Comparison of the Solubilities and the Viscosities of Polymeric Paclitaxel Prodrugs Synthesized by the Initiating Active Ingredient Method Various polymeric paclitaxel prodrugs were prepared and their solubility and viscosity were compared.

Synthesis of Paclitaxel Polymeric Prodrugs

The preparation of the various paclitaxel prodrugs follows the same method as Example 2, by changing the monomer used in place of the acrylamide: either N,N-dimethylacrylamide (DMAAm), or oligo (ethylene glycol) methyl ether methacrylate (OEGMA), i.e. glycerol monomethacrylate (GMA). These three monomers are known for their water solubility. For the linear paclitaxel-poly (ethylene glycol) prodrug, the synthesis consisted of a simple ester coupling already described by Ceruti et al. (Journal of Controlled Release, 63, 2000, 141-153).

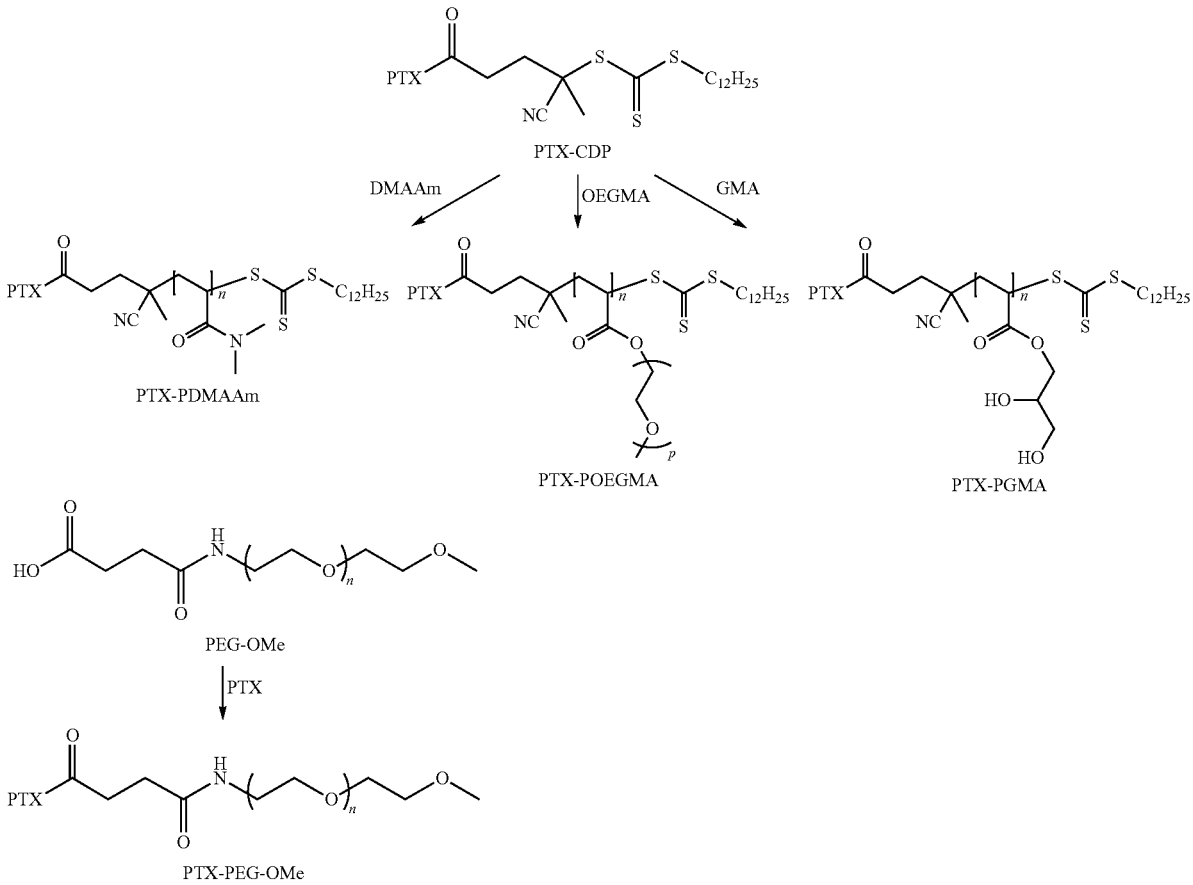

The polymers obtained have the following characteristics: PTX-PAAm $M_n$ 21.600, $M_w/M_n$ 1.12 (Example 2); PTX-PDMAAm $M_n$ 20,200, $M_w/M_n$ 1.02; PTX-POEGMA $M_n$ 24,500; PTX-PGMA $M_n$ 20,500, $M_w/M_n$ 1.11; PTX-PEG $M_n$ 21,000, $M_w/M_n$ 1.05.

Comparison of Solubilities of Polymeric Prodrugs

The solubility is evaluated at a concentration of 200 mg/ml of polymeric prodrugs, to distinguish the soluble polymeric prodrugs from the polymeric prodrugs in suspension, one or two centrifugations (16,873 g, 30 min) are carried out. Solubility is assessed by the absence of visible aggregates at the level of the Eppendorf base.

Surprisingly, all the polymer solutions have a deposit except for PTX-PAAm for which the solution remains transparent. PAAm therefore allows complete solubilization of paclitaxel at 200 mg/ml. The other prodrugs therefore have a lower solubility than PTX-PAAm.

Viscosity Studies of Different Polymeric Prodrugs by Syringability

Figure 4:
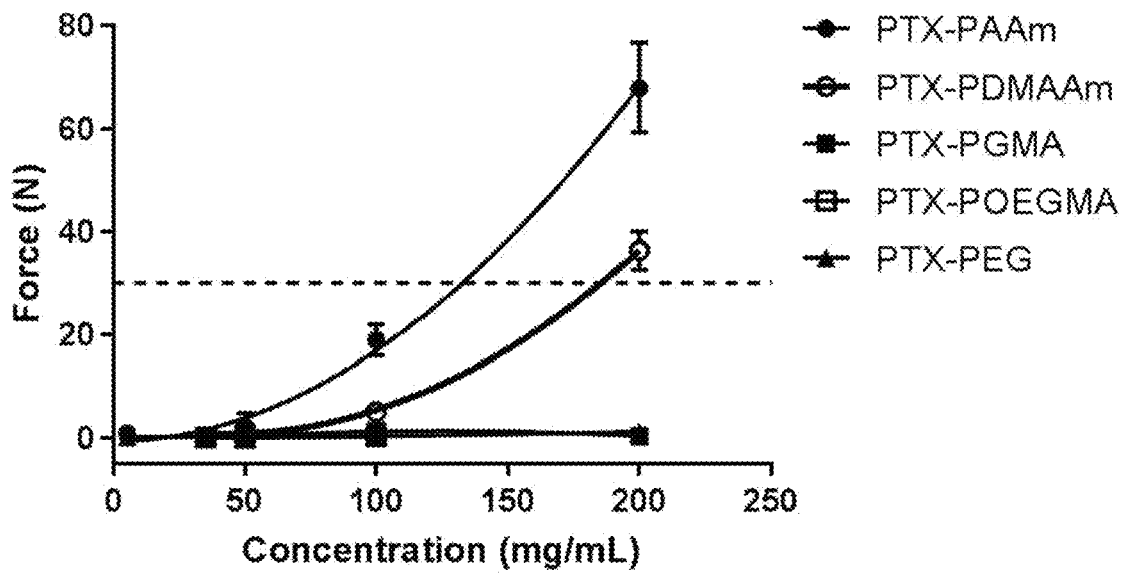
FIGS. 4 and 5: Graphs of the results of the viscosity studies of various polymeric prodrugs by syringability (Force (N) as a function of the concentration (mg/ml)).

Viscosity is a reflection of the solubility of a polymer. The phenomena of entanglement of the polymer chains are greater when the polymeric prodrug is very soluble, which leads to increased viscosity. Viscosity is measured using syringability studies as a function of concentration. The syringability of polymer solutions has been estimated using custom-made equipment (Burckbuchler et al., Eur. J. Pharm. Biopharm., 76, 2010, 351-356) coupled with a texture analyzer (TA.XT Plus Texture Analyzer, Stable Micro Systems) with a 30 kg force sensor. 400 µl of each solution is withdrawn and then injected through a 1 ml syringe (MeritMedical, Medaillon® Syringe) and a 26G×½" needle (Terumo Neolus, 0.45×12 mm) at a speed of 1 mm/s. The injection force is measured at the rate of 25 measurements per second. Each sample is injected 3 times in a row. By this method, we consider that a solution is difficult to inject if the force required for injection exceeds 30 N. The results are shown in FIG. 4.

The viscosity of PTX-PAAm is higher than that of other polymers which is linked to the strongest entanglement of the polymer chains and therefore to the greatest viscosity. Surprisingly, PAAm is the polymer having the strongest capacity to dissolve very hydrophobic PAs such as PTX.

Example 4: Comparison of the Viscosities of Polyacrylamide Prodrugs of Paclitaxel as a Function of the Nature of the Terminal Part of the Prodrug In this example, the viscosity of three PTX-PAAm prodrugs was compared as a function of the nature of the terminal part of the prodrug. To do this, three control agents were synthesized by the same synthetic route as that given in example 1 from different RAFT agents: one terminated by a C12 alkyl chain (example 1, noted RAFT-C12), another with a C4 alkyl chain (2-(butylthiocarbonothioylthio) propanoic acid, designated RAFT-C4) and a final one terminated by a C2 alkyl chain (4-cyano-4-(ethylcarbonothioylthio) pentanoic acid, designated RAFT-C2). Then these were used to polymerize acrylamide as described in Example 2 to obtain the prodrugs PTX-PAAm-C12 (Example 2), PTX-PAAm-C4, and PTX-PAAm-C2 respectively. The following illustration summarizes these different syntheses:

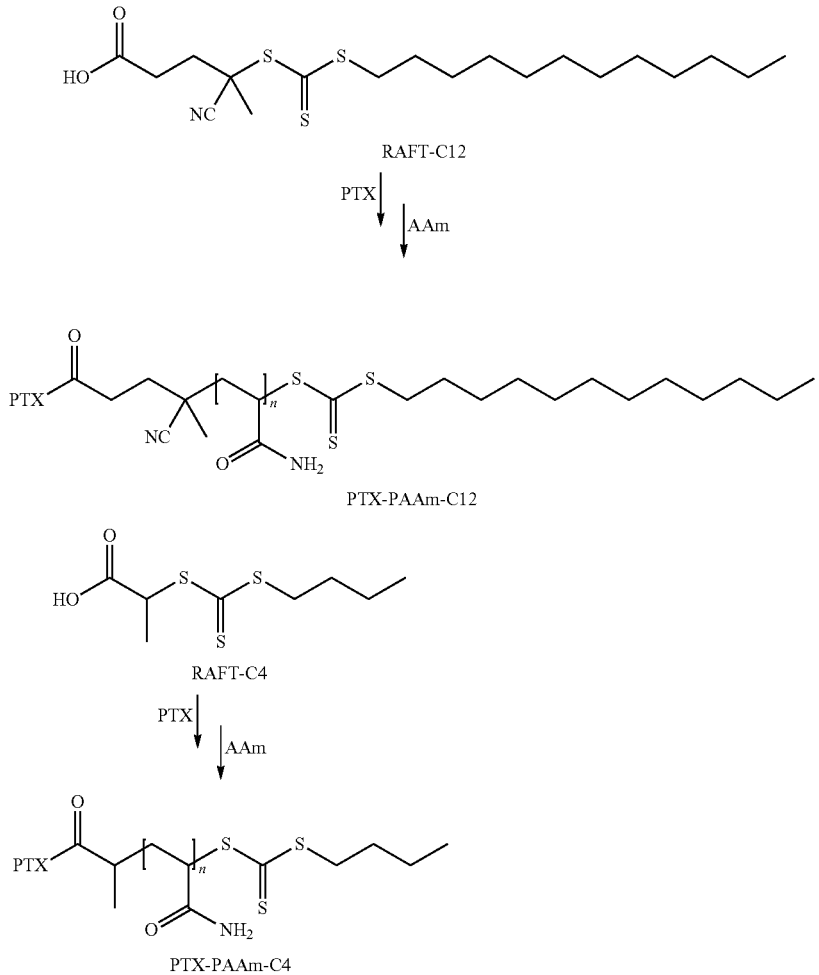

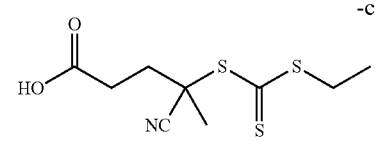

RAFT-C2

PTX ↓  ↓ AAm

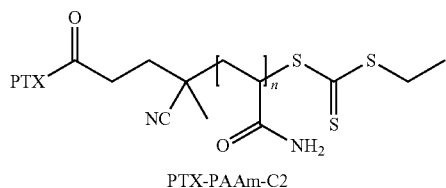

PTX-PAAm-C2

The polymers obtained have the following characteristics: PTX-PAAm-C12 $M_n$ 21,600, $M_w/M_n$ 1.12 (Example 1); PTX-PAAm-C4 $M_n$ 26.400, $M_w/M_n$ 1.04; PTX-PAAm-C2 $M_n$ 24, 100, $M_w/M_n$ 1.09.

Figure 5:
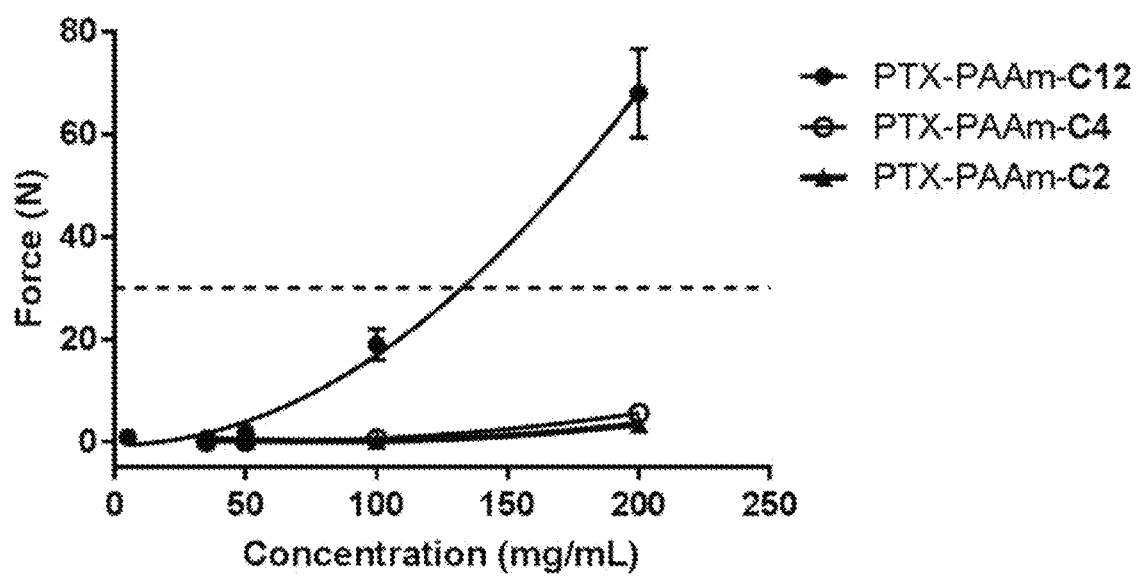

The viscosity of the various prodrugs was measured by the same method described in Example 3; the results are grouped in FIG. 5.

Surprisingly, a decreasing viscosity was observed depending on the nature of the terminal part of the prodrug: PTX-PAAm-C12>PTX PAAm-C4>PTX PAAm-C2.

Example 5: Polymerization Initiated by a Peptide (RGD)

Synthesis of the new RAFT agent RGD-CDP, the chemical structure of which is given in the illustration below:

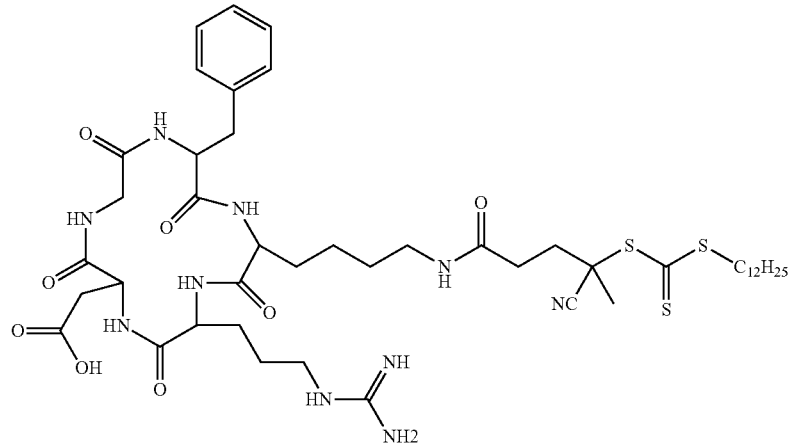

Cyclo-RGD (50.00 mg, 0.083 mmol) is dissolved in anhydrous DMF (3 ml), then DIPEA is added and the solution is stirred. In a separate vial, NHS-activated CDP (41.00 mg, 0.083 mmol) is dissolved in anhydrous DMF (2 ml) and the solution is added dropwise to the RGD solution. The resulting solution is stirred for 24 h at room temperature under an argon atmosphere. After 24 h, RGD (25.00 mg, 0.042 mmol) is added, and the solution is stirred overnight. The DMF is then removed to give a yellow solid which is triturated in DCM and dried. RGD-CDP is obtained in the form of a yellow solid (80.5 mg) with a yield of 98%. $^1$H NMR (300 MHz, DMSO-$d_6$) δ8.40 (s, 1H), 8.09 (t, J=7.4 Hz, 2H), 8.00 (d, J=5.1 Hz, 2H), 7.70 (d, J=7.1 Hz, 1H), 7.60 (s, 1H), 7.21 (m, 6H), 4.60 (m, 1H), 4.46 (m, 1H), 4.19 (m, 1H), 4.06 (m, 1H), 3.97 (s, 1H), 3.09 (m, 3H), 2.95 (s, 3H), 2.60 (s, 2H), 2.35 (d, J=6.6 Hz, 3H), 1.86 (s, 3H), 1.25 (s, 18H), 0.85 (t, J=6.8 Hz, 3H); $^{13}$C NMR (75 MHZ, DMSO-$d_6$) δ171.65, 171.13, 170.57, 157.10, 137.23, 129.54, 128.57, 126.73, 49.34, 47.55, 36.88, 35.58, 34.34, 29.34, 28.95, 28.59, 27.72, 25.67, 24.36, 22.54, 14.39; IR v=3270, 2924, 2854, 1635, 1546, 1439, 1379, 1200, 1182, 1075, 1130, 799, 720, 698, 606, 517 cm$^{-1}$.

Synthesis of the Polymer

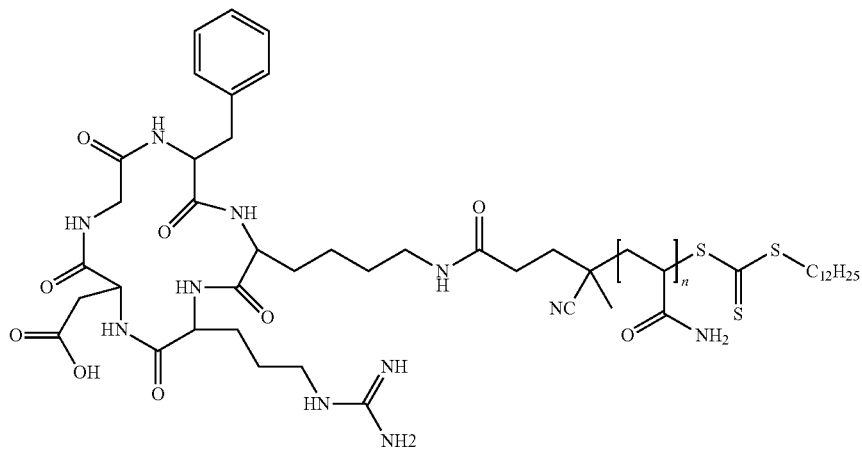

The polymerization of acrylamide is then carried out in the presence of this new RAFT agent by following the procedure described in Example 2. At the end of the purification, a white solid is obtained. $^1$H NMR (400 MHZ, DMSO-$d_6$) δ8.30 (s, 2H), 8.09 (t, J=7.4 Hz, 2H), 7.76 (s, 2H), 7.58 (d, J=9.0 Hz, 2H), 7.20 (m, 6H), 6.73 (m, 330H), 3.36 (m, 2H), 3.23 (s, 1H), 2.68 (m, 1H), 2.33 (m, 3H), 2.13 (s, 170H), 1.56 (s, 345H), 1.27 (s, 18H), 0.87 (t, J=6.8 Hz, 3H); $^{13}$C NMR (75 MHZ, DMSO-$d_6$) δ176.97); IR v=3335, 3194, 2933, 1652, 1610, 1451, 1415, 1347, 1321, 1191, 1124, 491 cm$^{-1}$.

Example 6: Synthesis of Rhodamine Fluorescent Polymers

The rhodamine (Rho) piperazine used was synthesized following a synthetic route already described by Nguyen et al. (Organic Letters, 2003, 5, 3245-3248). This is coupled to the RAFT CDP agent to obtain the Rho-CDP, the structure of which is given in the following illustration:

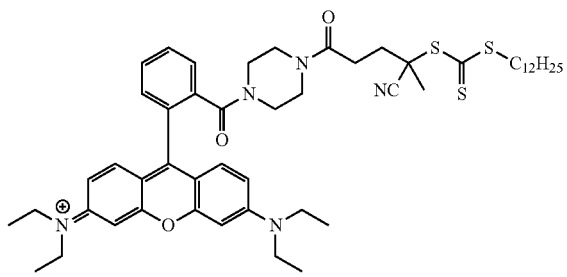

The rhodamine piperazine (200.00 mg, 0.39 mmol) was dissolved in dry DCM (12 ml). Under an argon atmosphere, HATU (223.00 mg, 0.59 mmol), DIPEA (0.20 ml, 1.20 mmol) and CDP (158.00 mg, 0.39 mmol) were added and the solution was stirred overnight at room temperature. The solvent was removed in vacuo and the crude mixture was purified by column chromatography (DCM up to 2% MeOH/DCM) to give a pink powder (170 mg) with a yield of 49%. Rf=0.75 (DCM/MeOH 5%); $^1$H NMR (300 MHZ, DMSO-$d_6$) δ7.76 (m, 4H), 7.54 (s, 2H), 7.13 (dd, J=18.4, 10.1 Hz, 4H), 6.95 (s, 3H), 3.66 (d, J=6.7 Hz, 9H), 3.40 (t, J=29.9 Hz, 18H), 2.09 (s, 2H), 1.85 (s, 2H), 1.63 (s, 2H), 1.23 (m, 21H), 0.84 (t, J=6.1 Hz, 3H); $^{13}$C NMR (75 MHZ, CDCl$_3$) δ157.71, 155.70, 148.72, 132.35 (CH2), 130.04 (CH2), 127.23 (CH2), 114.38, 110.01, 96.09 (CH2), 46.07, 41.45, 36.83, 32.14, 29.17, 27.69, 22.49, 13.78, 12.84 (CH2); IRv=2922, 1634, 1585, 1465, 1411, 1335, 1272, 1245, 1178, 1132, 1072, 1006, 835, 682, 556 cm$^{-1}$; HR-MS (ESI+): m/z calculated for C51H70N5O3S3+ [M+H]+ 896.4635 found 896.4641.

Synthesis of the Polymer

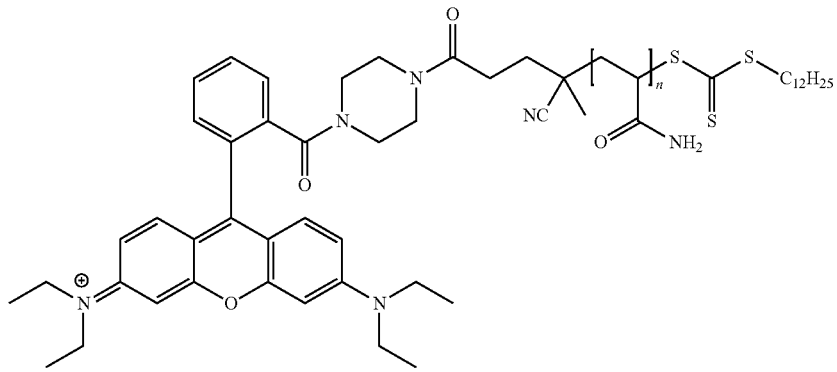

The polymerization of acrylamide is then carried out in the presence of this new RAFT agent by following the procedure described in example 2. At the end of the purification, a pink solid is obtained. $^1$H NMR (400 MHZ, DMSO-$d_6$) δ7.77-7.72 (m, 2H), 7.70-7.65 (m, 1H), 7.52-7.48 (m, J=8.6 Hz, 2H), 7.23-6.40 (m, 501H), 3.66 (dd, J=14.3, 7.2 Hz, 5H), 3.32 (m, 6H), 2.66 (m, 2H), 2.33-2.29 (m, 5H), 2.15 (s, 227H), 1.54 (m, 484H), 1.25 (s, 18H), 1.23 (s, 5H), 1.21 (s, 3H), 1.17 (s, 1H), 1.15 (s, 1H), 0.86 (t, J=6.8 Hz, 3H); $^{13}$C NMR (75 MHZ, DMSO-$d_6$) δ177.35; IR ν=3344, 3193, 1652, 1415, 1146, 1330, 556 cm$^{-1}$.

Example 7: Synthesis of Cyanine 5.5 Fluorescent Polymers

Firstly, the polyacrylamide is synthesized with the RAFT CDP agent activated by N-hydroxysuccinimide following the protocol given in example 2. The structure of the polymer is given in the following illustration:

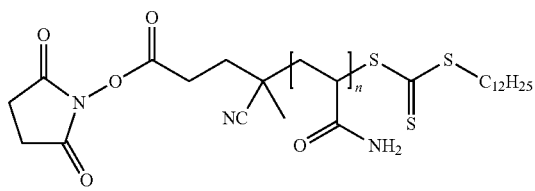

This polymer is then dissolved in DMSO (0.7 ml). In a separate bottle, Cyanine (0.005 mmol) and TEA (1.4 µL, 0.01 mmol) are dissolved in DMSO (0.3 ml) and added dropwise to the polymer solution. The mixture is stirred under argon overnight at room temperature. A precipitate is formed after adding cold methanol, the precipitate is filtered and redissolved in DMSO, and the solution is dialyzed in Milli-Q water for 24 h. The solution is lyophilized to give a blue solid. $^1$H NMR (400 MHZ, DMSO-$d_6$) δ6.77 (s, 458H), 2.12 (s, 232H), 1.69 (s, 112H), 1.47 (s, 329H), 1.26 (s, 18H), 0.87 (t, J=6.3 Hz, 3H); $^{13}$C NMR (75 MHZ, DMSO-$d_6$) δ177.36; IR ν=3337, 3190, 1651, 1607, 1451, 1412, 1317, 1120 cm$^{-1}$.

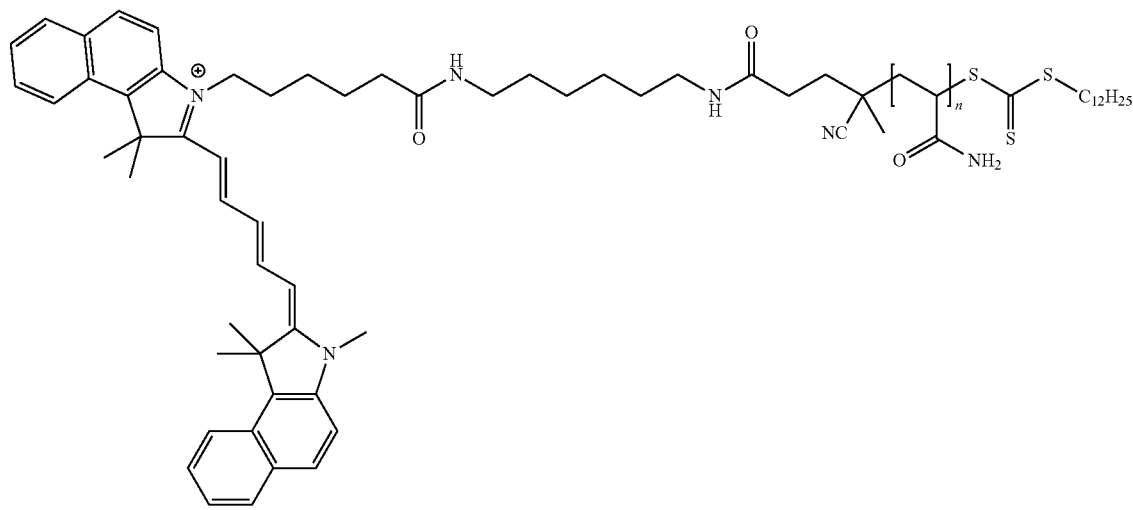

Example 8: Synthesis of Polyacrylamide Prodrugs with Different Bonds Between the Active Ingredient and the Polymer In order to change the chemical bond between the polyacrylamide and the active ingredient, here paclitaxel, we have synthesized three new RAFT agents with different bonds: diglycolate bond for PTX-digly-CDP, carbamate for PTX-carbamate-CDP, and carbonate for PTX-carbonate-CDP.

PTX-Digly-CDP Synthesis

This synthesis is carried out in two stages; a first consists in reacting the CDP with glycolic anhydride in the presence of a base (triethylamine). The reaction is carried out at room temperature for 24 h and quantitatively forms CDP-glycolic acid 1. A coupling between the latter with paclitaxel in the presence of EDC as coupling agent and DMAI as base for 24 h at 30° C. gives the product PTX-digly-CDP 2 with a yield of 50%.

an aqueous NaHCO$_3$ solution and dried over Na$_2$SO$_4$. The product is purified by chromatography on silica gel with a DCM/EtOAc gradient (16 up to 50%). The product is isolated as a yellow powder with 50% yield. $^1$H NMR (300 MHz, CDCl$_3$) δ8.17 (d, J=7.5 Hz, 2H), 7.77 (d, J=7.6 Hz, 2H), 7.69-7.33 (m, 15H), 7.13 (d, J=9.1 Hz, 1H), 6.35-6.19 (m, 2H), 6.05 (dd, J=9.1, 2.5 Hz, 1H), 5.70 (d, J=7.0 Hz, 1H), 5.61 (s, 1H), 4.98 (d, J=8.8 Hz, 1H), 4.57-4.39 (m, 1H), 4.40-4.03 (m, 10H), 3.84 (d, J=6.9 Hz, 1H), 3.33 (t, J=7.2 Hz, 1H), 2.49 (s, 3H), 2.24 (s, 3H), 2.06-1.80 (m, 12H), 1.70 (s, 5H), 1.39-1.20 (m, 23H), 0.89 (t, J=6.5 Hz, 3H). $^{13}$C NMR (75 MHZ, CDCl$_3$) δ217.21, 203.75, 171.18, 169.84, 169.45, 168.98, 167.65, 167.14, 167.00, 142.54, 136.75, 133.64, 133.56, 132.91, 131.98, 130.24, 129.22, 129.13, 128.72, 128.64, 128.57, 127.27, 126.59, 119.23, 109.97, 84.44, 81.07, 79.14, 76.44, 75.57, 75.13, 74.47, 72.09, 68.15, 68.02, 63.75, 58.51, 52.75, 46.68, 45.58, 43.20, 37.07, 35.54, 31.89, 29.60, 29.53, 29.40, 29.32, 29.06,

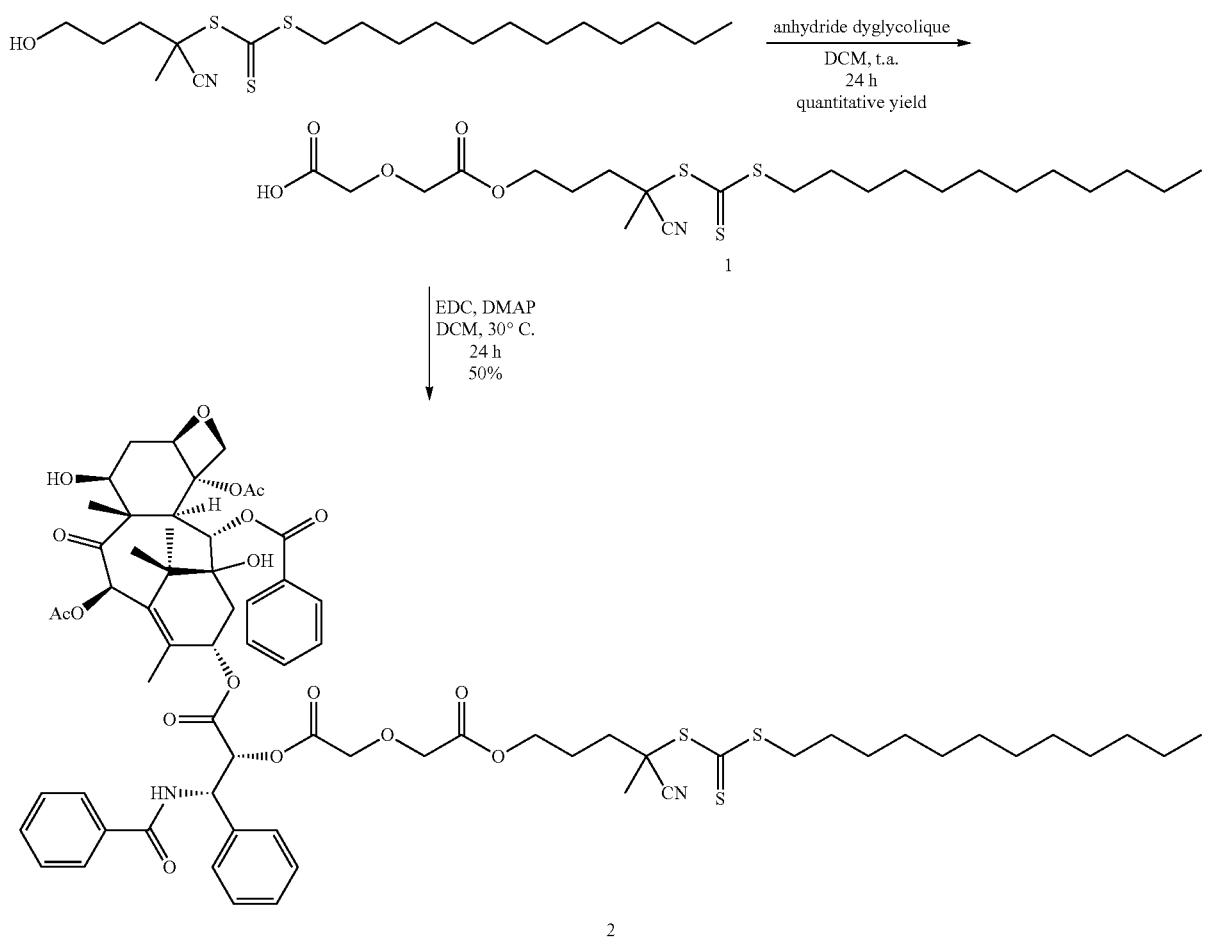

(NB: anhydride glycolique = glycolic anhydride)

CDP 1 (800 mg, 1.40 mmol), DMAI (170 mg, 1.40 mmol), EDC·HCl (276 mg, 1.40 mmol) of anhydrous DCM (6 ml) are dissolved in a flask. Then paclitaxel (1.00 g, 1.17 mmol) in anhydrous DCM (2 ml) is added to the flask. After 7 of reaction at 30° C., EDC·HCl (130 mg, 0.68 mmol) and DMAI (75.0 mg, 0.61 mmol) are added and the mixture is stirred overnight at 30° C. The organic phase is washed with 28.92, 27.67, 26.84, 24.86, 24.79, 24.19, 22.72, 22.67, 22.16, 20.82, 14.80, 14.11, 9.62.

PTX-Carbamate-CDP Synthesis

This synthetic route includes 3 parts summarized in the illustration below: The first part consists of the formation of CDP-NH$_2$. The latter has never been described in the literature. First, CDP is activated in the presence of NHS and DCC to provide product 4 with 60% yield. The next step is to couple a diaminoethane chain with CDP-NHS to form a peptide bond. In order to avoid double coupling, the diaminoethane is protected by a group (BOC). Diaminoethane-BOC was added to a solution of CDP-NHS in anhydrous DCM at 0° C. to give the product 5 with a yield of 91%. Then a deprotection step of product 5 in the presence of trifluoroacetic acid at room temperature provides the CDP-NH$_2$, product 6; quantitatively, this product is used in the next step without any purification.

The second part is the activation of paclitaxel with paranitrophenyl chloformate to give PTX-PNPh. This reaction is carried out by successive addition of formate for 4 h on a solution of paclitaxel in anhydrous dichloromethane at −50° C. and in the presence of pyridine. After purification, the PTX-PNPh, product 7, is obtained with a yield of 45%.

The third part consists in coupling the activated paclitaxel PTX-PNPh with CDP-NH$_2$ in the presence of triethylamine at −20° C. in anhydrous DMF, PTX-carbamate-CDP, product 8, is obtained with a yield of 51%.

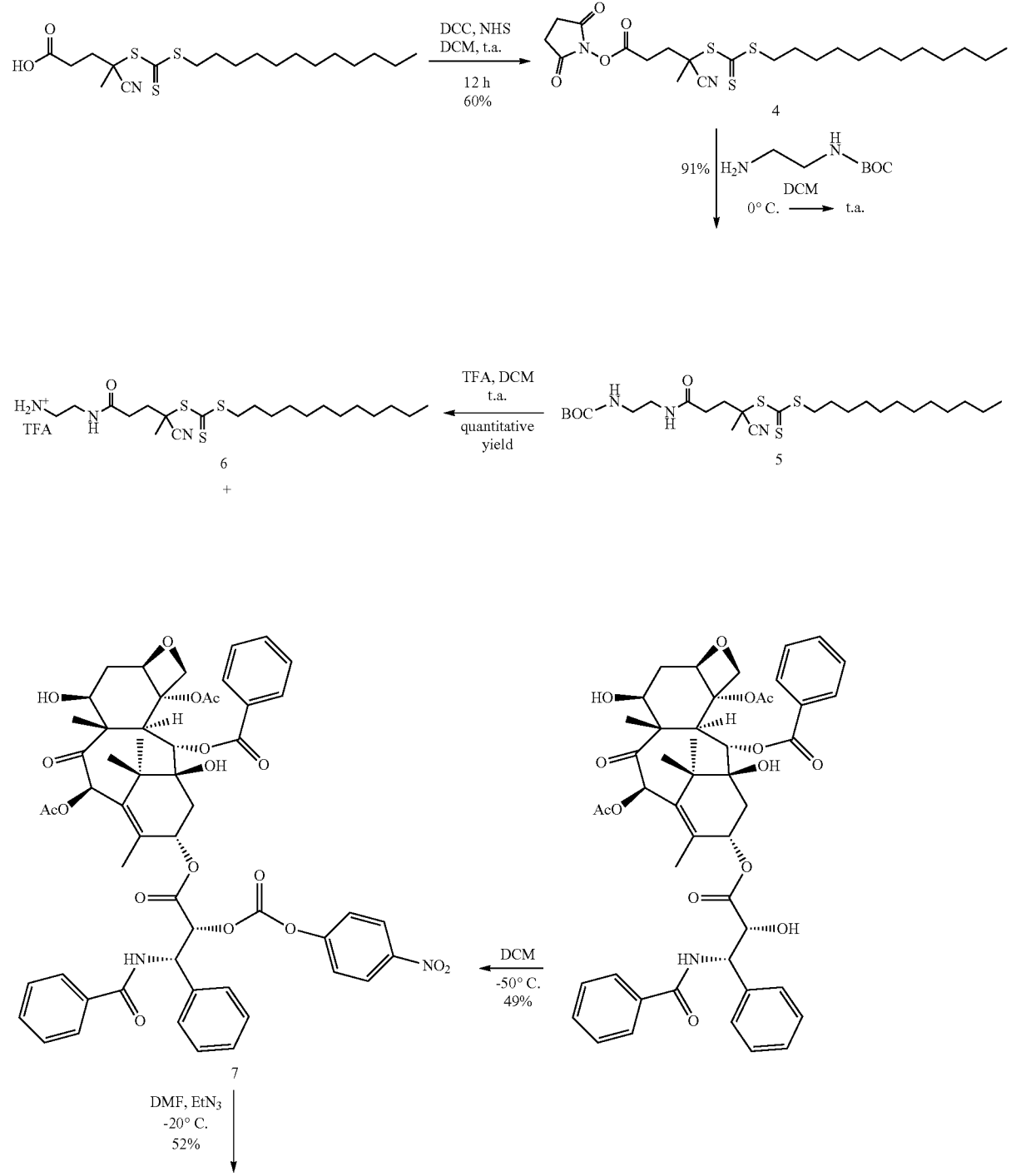

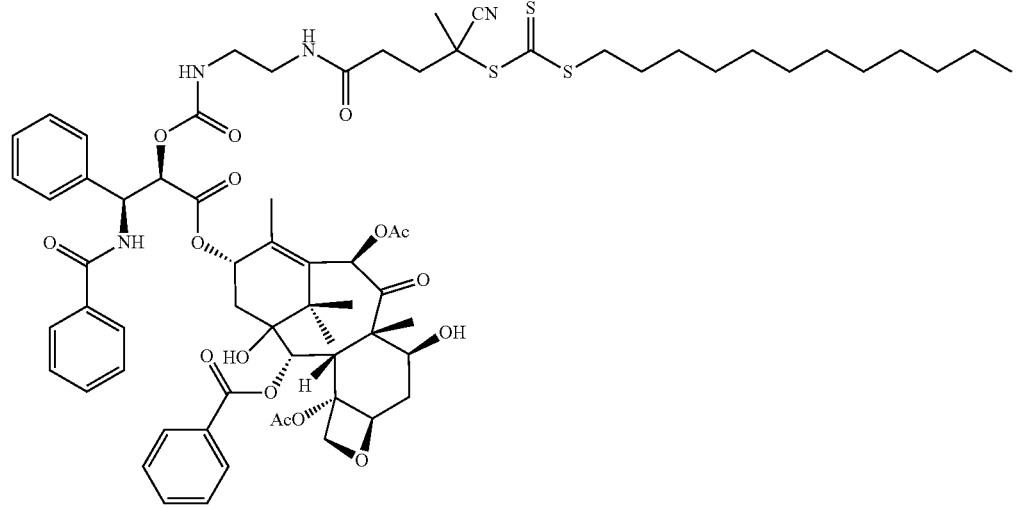

8

In a flask containing a solution of paclitaxel (16.00 mg, 0.028 mmol) and Et3N (10 μL) in anhydrous DMF (2 ml), is added dropwise a solution of CDP and Et3N in anhydrous DMF under argon and at −30° C. The mixture is stirred for 2:30 h at −20° C. It is then diluted with a saturated bicarbonate solution and extracted with AcOEt. The organic phases are evaporated and the crude residue is purified by chromatography on silica gel (AcOEt: Cyclohexane 1:1). The product is obtained as a light yellow powder with a yield of 51%.

$^1$H NMR (300 MHZ, CDCl$_3$) δ 8.16 (d, J=7.6 Hz, 2H), 7.78 (d, J=7.5 Hz, 2H), 7.69-7.31 (m, 15H), 7.09 (dd, J=16.4, 7.7 Hz, 1H), 6.28 (m, J=18.3 Hz, 2H), 6.09-5.87 (m, 2H), 5.70 (d, J=7.0 Hz, 1H), 5.50 (d, J=2.8 Hz, 1H), 5.00 (d, J=10.0 Hz, 2H), 4.27 (m, J=25.6 Hz, 4H), 3.83 (s, 2H), 3.32 (t, J=7.5 Hz, 2H), 2.56 (s, 3H), 2.45 (s, 6H), 2.25 (s, 3H), 1.95 (s, 3H), 1.85 (s, 3H), 1.67 (d, J=17.9 Hz, 10H), 1.26 (d, J=9.8 Hz, 20H), 0.90 (t, J=6.5 Hz, 3H). HRMS (ESI)+ calculated for C29H89N4O16S3 1325.5436, found 1325.5425.

Synthesis of PTX-Carbonate-CDP

This synthesis is carried out using PTX-PNPh and the RAFT CDP agent terminated by an alcohol function, CDP-OH. The mixture is stirred for 48 h at room temperature in anhydrous DCM and in the presence of a base (DMAI), PTX-carbonate-CDP, product 9 is obtained with 65% yield.

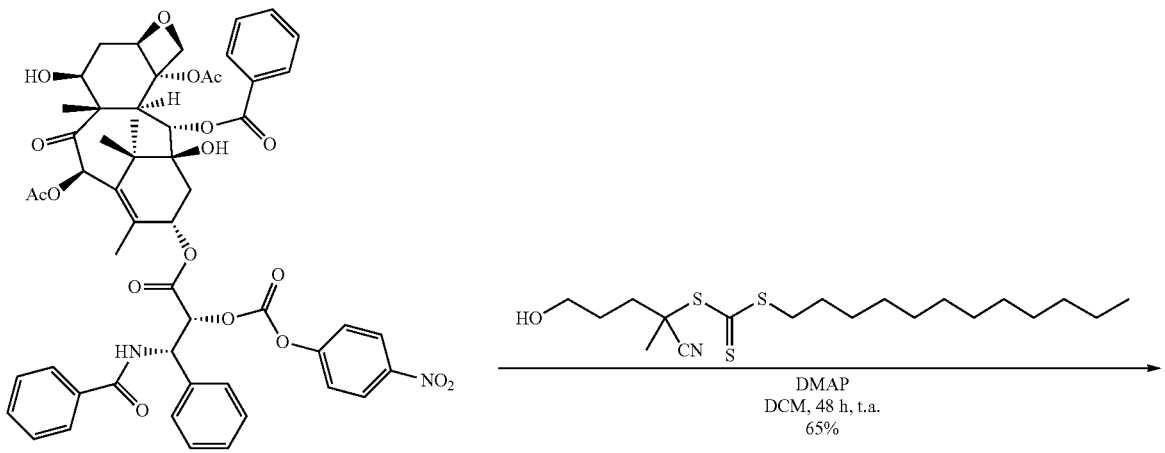

-continued

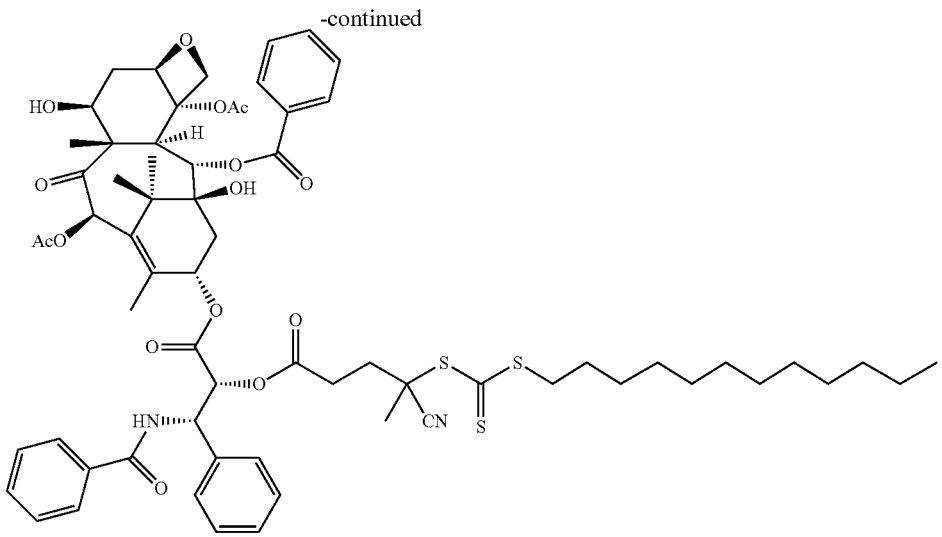

9

In a flask are mixed activated paclitaxel PTX-PNPh (60.00 mg, 0.058 mmol), CDP-OH (23.00 mg, 0.058 mmol), and DMAP (8.30 mg, 0.068 mmol) and anhydrous DCM (4 ml). The mixture is stirred for 48 h at room temperature, protected from light. It is then diluted with DCM and washed with saturated sodium bicarbonate. The organic phases are dried over $Na_2SO_4$ and evaporated. The product is purified by chromatography on silica gel (Cyclo/AcOEt 20→50%) and is obtained as a light yellow powder with 65% yield. $^1$H NMR (300 MHZ, $CDCl_3$) δ8.17 (d, J=7.3 Hz, 2H), 7.78 (d, J=8.0 Hz, 2H), 7.72-7.30 (m, 15H), 6.95 (d, J=9.1 Hz, 1H), 6.32 (s, 2H), 6.02 (d, J=8.5 Hz, 1H), 5.71 (d, J=7.1 Hz, 1H), 5.44 (s, 1H), 5.00 (d, J=8.7 Hz, 1H), 4.45 (d, J=6.8 Hz, 1H), 4.35 (d, J=8.6 Hz, 1H), 4.23 (d, J=7.2 Hz, 2H), 3.84 (d, J=7.5 Hz, 1H), 3.34 (t, J=7.3 Hz, 2H), 2.49 (s, 3H), 2.25 (s, 3H), 2.01-1.85 (m, 10H), 1.71 (s, 8H), 1.39-1.13 (m, 20H), 0.90 (t, J=6.5 Hz, 3H). $^{13}$C NMR (75 MHz, $CDCl_3$) δ203.78, 203.62, 171.25, 169.85, 167.83, 142.61, 136.66, 133.69, 132.87, 132.07, 130.23, 129.17, 128.74, 128.59, 127.16, 126.57, 84.45, 81.10, 79.18, 76.46, 75.59, 75.10, 72.13, 67.82, 58.53, 57.70, 52.74, 47.65, 47.23, 46.65, 45.57, 43.21, 37.07, 35.55, 35.39, 31.91, 29.62, 29.54, 29.42, 29.34, 29.08, 28.94, 27.68, 26.85, 24.92, 24.19, 22.74, 22.69, 22.17, 20.84, 14.84, 14.13, 9.61.

Synthesis of Paclitaxel-Polyacrylamide Prodrugs with Different Chemical Bonds

The polyacrylamide prodrugs of paclitaxel with different chemical bonds were synthesized by following the procedure described in Example 2 and using the synthesized RAFT agents: PTX-digly-CDP, PTX-carbamate-CDP and PTX-carbonate-CDP. The following polymers are obtained: PTX-digly-PAAm $M_n$ 27.300, $M_w/M_n$ 1.10; PTX-carbamate-PAAm $M_n$ 27.100, $M_w/M_n$ 1.17; PTX-carbonate-PAAm $M_n$ 27,800, $M_w/M_n$ 1.09.

Release Kinetics of Paclitaxel in PBS and Murine Plasma

Paclitaxel release experiments were performed in PBS (Tween 80, 1%) and in murine plasma. The PTX, the PTX-ester-PAAm (example 2), the PTX-digly-PAAm and the PTX-carbonate-PAAm were incubated in PBS and murine plasma at 37° C. at the same concentration (1 μg/ml eq. PTX). At 0, 2 h, 4 h, 6 h, 24 h and 48 h, 200 μL of sample is taken for quantification.

Sample preparation: 200 μl aliquots are mixed with 600 μl of acetonitrile and 20 μl of deuterated Paclitaxel (PTX-d5) at 1 μg/ml (internal standard). The samples are shaken for 15 minutes and centrifuged for 10 minutes before analysis.

LC conditions: Column: Column C18 (HILIC) (Nucleodur, EC 125/2, 100-5-C18, Macherey-Nagel, Hoerdt, France). Mobile phase: Acetonitrile/water (50/50) with 0.1% formic acid; Duration: 8 min.

Figure 6:
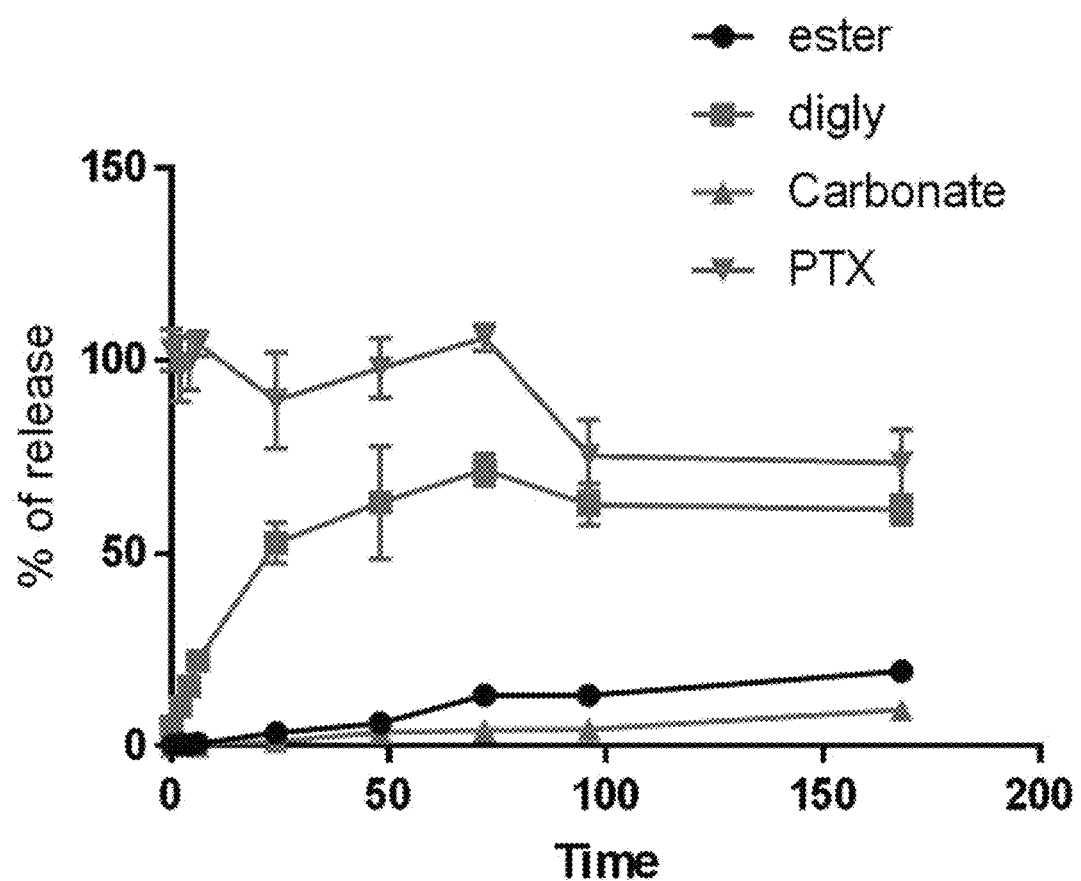
FIGS. 6 and 7: release in PBS (FIG. 6) and in murine plasma (FIG. 7) of paclitaxel from prodrug polymers having different chemical bonds between the PTX and the polymer (ester, diglycolate, carbonate).
Figure 7:
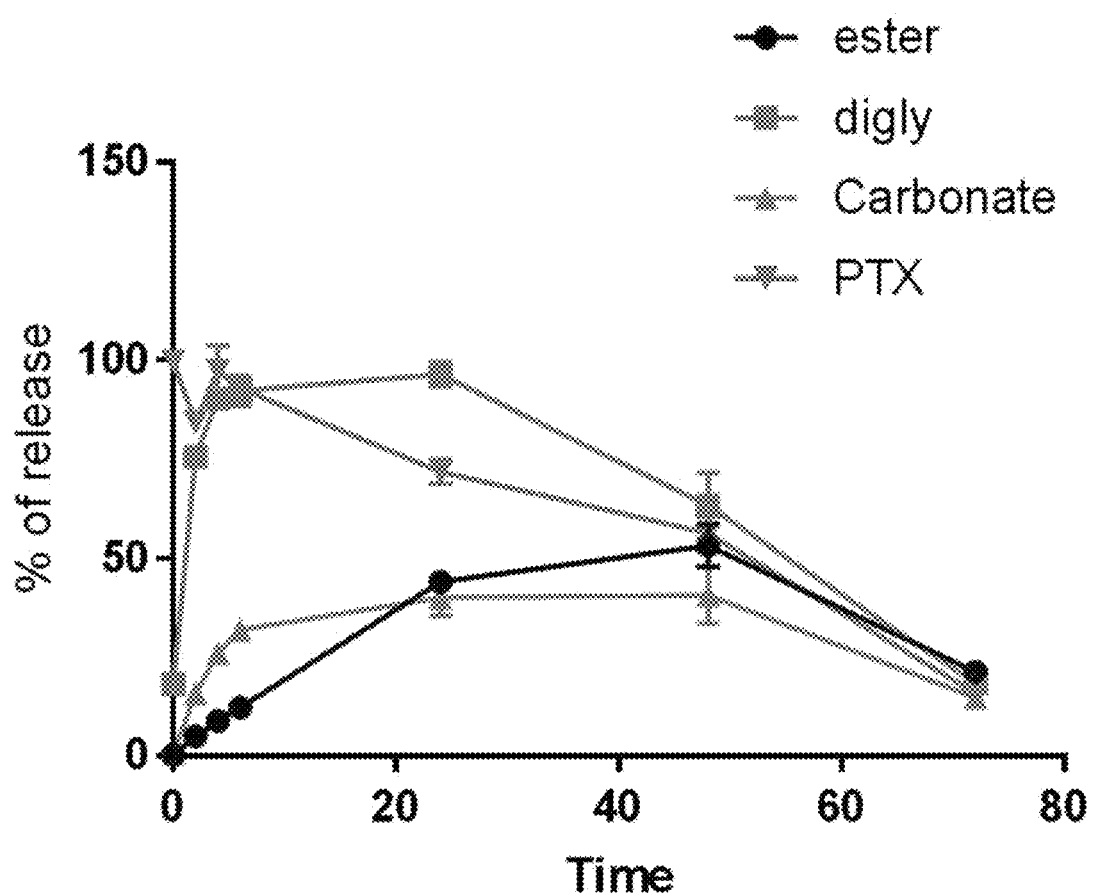

ESI-MS/MS conditions: The analyses are carried out on a triple quadrupole mass spectrometer (TQD) detector with electrospray ionization interface (ESI) (Quattro Ultima, Waters, Guyancourt, France). The electrospray and mass parameters were optimized by direct infusion of pure analytes into the system. ESI parameters: capillary voltage 3.5 kV, conical voltage 35V, source temperature 120° C. desolvation temperature 350° C., with a nitrogen flow rate of 506 l/h. Mass parameters: Transitions are monitored as follows: PTX 854/286; PTX-d5 859/291. Calibration: the calibration curve was linear in the range of 5 to 1000 ng/ml (y=0.0047x+0.0838 $R^2$=0.9936 in PBS and y=0.0052x at 0.0131 $R^2$=0.9949 in murine plasma). The release profiles are illustrated in FIGS. 6 and 7.

Polymeric prodrugs with carbonate or ester linkages exhibit better stability in PBS than with a diglycolate linkage. The same trend is observed in murine plasma but the ester and carbonate bonds quantitatively release more active molecule (here PTX).

Example 9: Telechelic Polymers

Route 1: Bioconjugation by Thiol-Maleimide Coupling.

The synthesis is divided into different stages: firstly, the peptide is coupled to a linker having a maleimide function, the trithiocarbonate function at the end of the polymer chain is then modified to give a thiol and then the two elements are coupled by a thioether bond.

SMCC/Peptide Coupling

The first step consists in coupling the targeting ligand to the linker by peptide coupling. The cyclic RGD of cyclo sequence (-Arg-Gly-Asp-D-Phe-Lys) has a free amine originating from the lysine residue which may be used for peptic coupling with the linker.

The trifluoroacetic salt of cyclo-RGD 5 (50.00 mg, 0.083 mmol) was dissolved in dry DCM (3 ml). DMF was added dropwise until the solid was dissolved. DIPEA (0.023 ml, 0.12 mmol) was added and the solution was stirred. In a separate bottle, SMCC (27.70 mg, 0.083 mmol) was dissolved in dry DCM (2 ml) and the solution was added dropwise to the RGD solution. The resulting solution was stirred at room temperature for 24 h. The crude mixture was purified by preparative HPLC (H$_2$O/ACN 10 to 50% in 15 minutes) and lyophilized to give a white powder (69.2 mg) yield 51%. $^1$H NMR (400 MHZ, DMSO-d$_6$) δ8.39 (m, amide protons), 8.31 (s, amide protons), 8.29-8.13 (m, amide protons), 7.77 (d, J=8.6 Hz, Ha), 7.71 (t, J=5.4 Hz, H arginine), 7.23 (m, HI), 7.15 (dd, J=10.2, 4.3 Hz, Hk), 6.99 (m, Hw), 4.59 (dd, J=8.5 Hz, Hi), 4.44 (s, Hg), 4.26 (s, He and Hm), 4.13 (m, Hf), 3.23 (d, J=7.0 Hz, Hv), 3.08 (m, Hq), 2.95 (m, Hb), 2.63 (m, Hj), 2.19 (dd, J=16.3, 4.8 Hz, Hr), 2.00 (m, Hu), 1.68 (m, Hd or Hn), 1.61 (m, Hd or Hn), 1.55-1.39 (m, Ho/Hp/Hc), 1.38-1.19 (m, Ho/Hp/Hc), 1.19-1.04 (m, Ho/Hp/Hc); $^{13}$C NMR (100 MHZ, DMSO-d$_6$) δ174.87, 173.71, 172.16, 171.25, 170.65, 167.78, 156.93, 138.27, 134.34, 128.94, 127.99, 126.00, 54.83, 53.30, 50.96, 48.68, 43.78, 43.07, 37.83, 36.68, 36.13, 31.81, 31.49, 29.44, 28.57, 27.33, 24.61, 22.94.

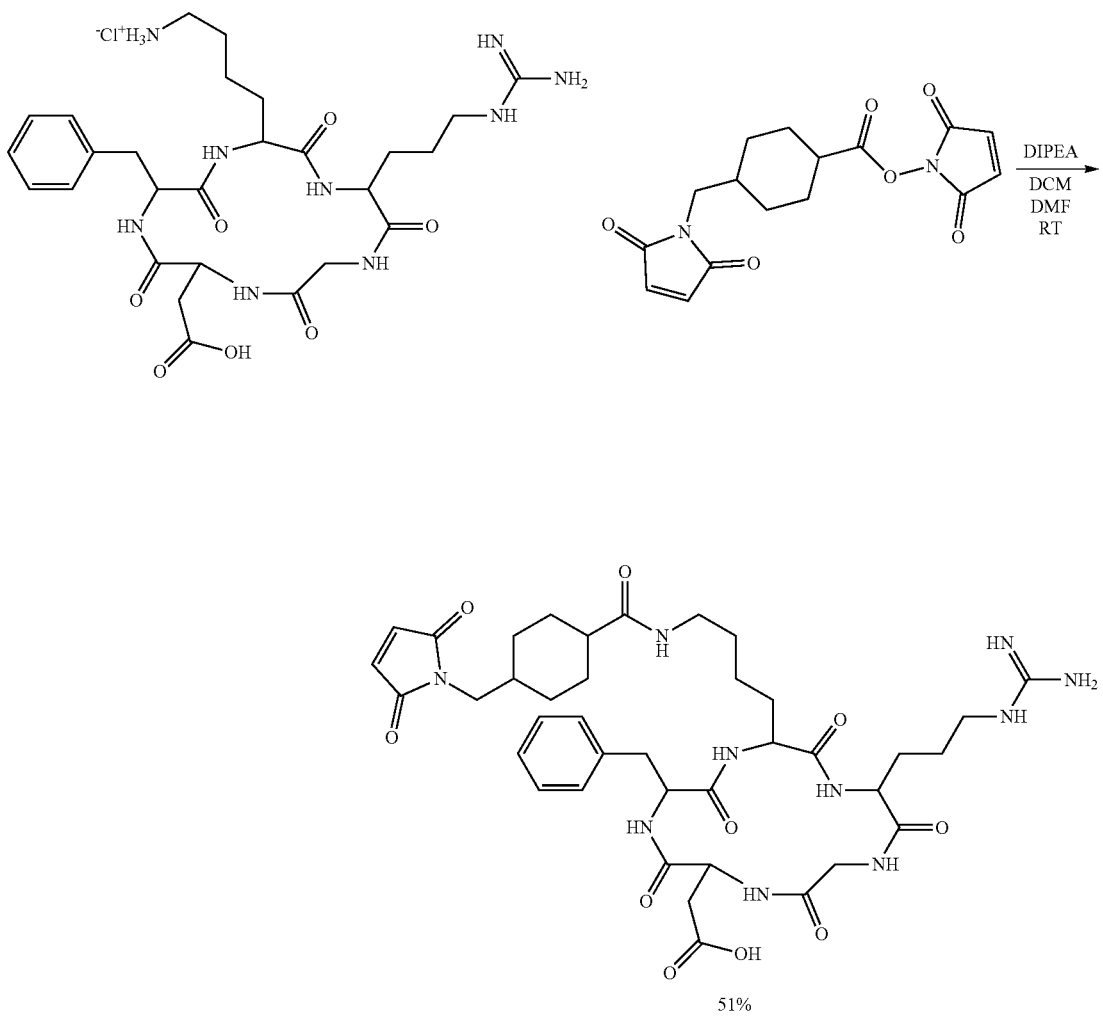

Illustration 4: Synthesis of the RGD-SMCC Conjugate

LC-MS analysis of the reaction crude made it possible to highlight the formation of the desired RGD/SMCC conjugate.

Modification of the Trithiocarbonate Function by Aminolysis

In order to achieve the thiol-maleimide coupling, the second step consists in modifying the RAFT agent at the end of the polymer chain to give a thiol. This reaction is carried out by cutting the trithiocarbonate function of the CDP with an amine by aminolysis.

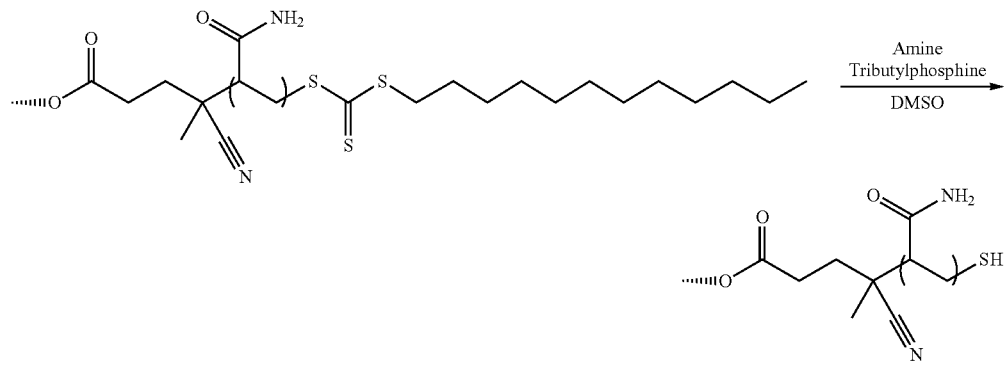

The PTX-PAAm-CDP was dissolved in DMSO and the solution was degassed with argon for 10 min. Propylamine and n-tributylphosphine were added to the solution and stirred at room temperature for 48 h under an argon atmosphere. PAAm-SH was obtained in the form of a powder after precipitation in cold diethyl ether. The powder was resuspended in DMSO and dialyzed in Milli-Q water for 3 days. The solution was lyophilized to give a white solid, PTX-PAAm-SH. $^1$H NMR (400 MHZ, DMSO-d$_6$) δ8.97 (s, 1H), 8.00 (d, J=7.2 Hz, 2H), 7.84 (d, J=7.4 Hz, 2H), 7.70-7.46 (m, 13H), 7.28-6.43 (m, 615H), 6.31 (s, 2H), 5.90 (m, 2H), 5.66 (m, 2H), 5.46 (d, J=7.0 Hz, 1H), 5.41 (d, J=7.9 Hz, 1H), 4.92 (d, J=10.0 Hz, 1H), 4.65 (d, J=6.4 Hz, 1H), 4.46 (s, 1H), 4.08-4.00 (m, 3H), 2.67 (dd, J=3.8, 1.9 Hz, 4H), 2.32 (dd, J=3.7, 1.8 Hz, 6H), 2.13 (s, 290H), 1.66 (s, 141H), 1.63 (s, 325H), 1.25 (s, 12H), 0.85 (t, J=7.0 Hz, 3H); $^{13}$C NMR (75 MHZ, DMSO-d$_6$) δ177.48; IR v=3346, 3196, 2942, 1655, 1615, 1451, 1415, 1347, 1322, 1123, 519 cm$^{-1}$.

The following stage of synthesis of the bioconjugate by thioether bond comprises the coupling between the thiol of the maleimide linker with the free thiol of the polymer previously obtained.

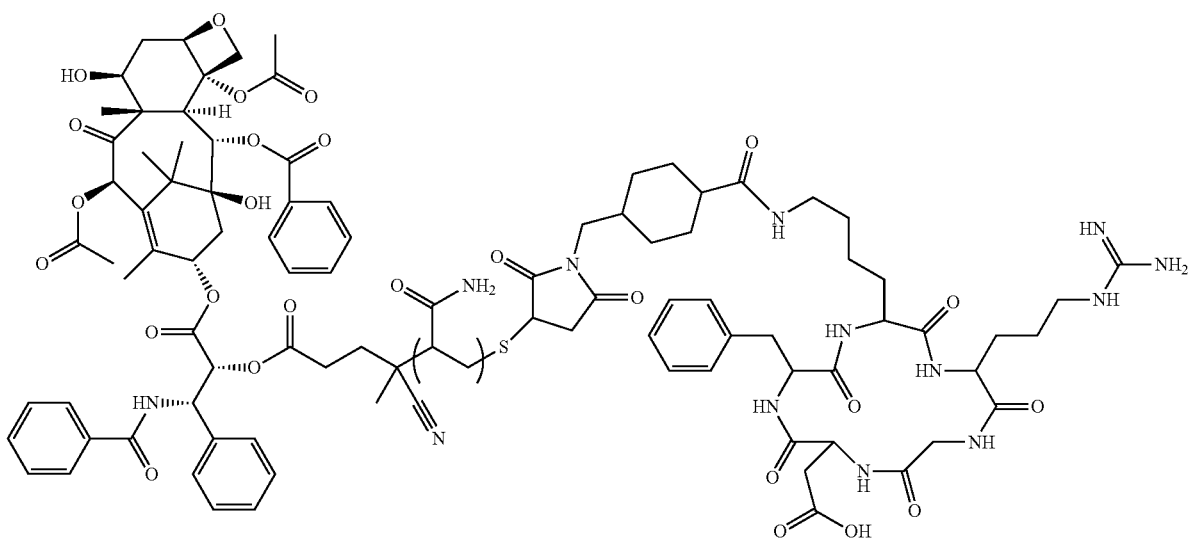

PTX-PAAm-RGD Bioconjugate Obtained by Thioether Bond

2. Route 2: Bioconjugation by Peptide Coupling

The second synthetic route for the PTX-PAAm-RGD bioconjugate represents an alternative strategy allowing the peptide to be coupled to the polymer by a peptide bond which is more stable than the thioether bond. This synthesis consists firstly in modifying the trithiocarbonate group by the radical route to give a chain terminated by a carboxylic acid, then in coupling the targeting ligand by peptide coupling, according to for example the synthesis:

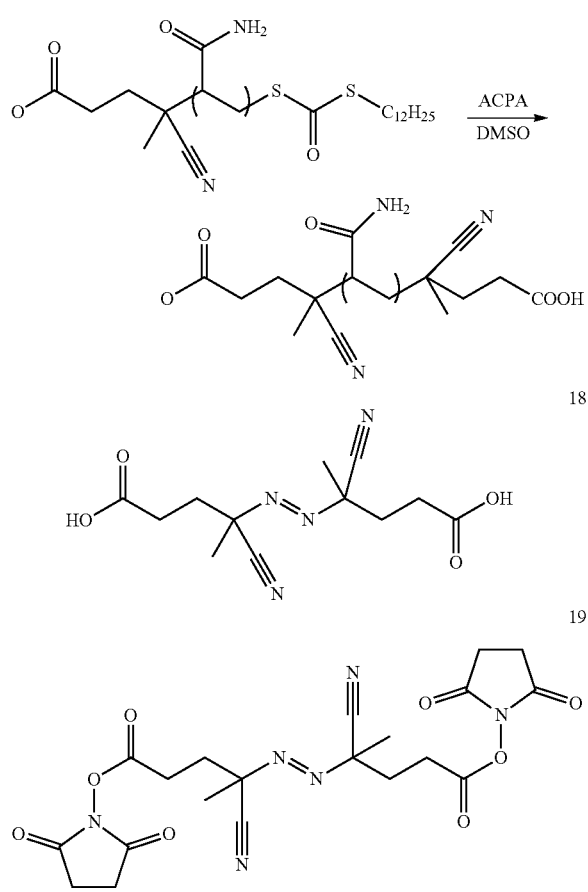

ACPA and ACPA pre-activated by NHS

PTX-PAAm-CDP (300 mg, 0.015 mmol), ACPA (84 mg, 0.30 mmol) and DMSO were added to a round bottom flask. The solution was degassed with argon for 10 min, then heated to 80° C. for 48 h. The solution was cooled and the polymer was precipitated by dropwise addition into cold diethyl ether to give a powder. The powder was resuspended in DMSO and dialyzed in Milli-Q water for 3 days. The solution was lyophilized to give a white solid, PTX-PAAm-COOH with a yield of 50%. $^1$H NMR (400 MHZ, DMSO-$d_6$) δ8.97 (m, 1H), 8.00 (d, J=7.4 Hz, 2H), 7.85 (d, J=7.5 Hz, 2H), 7.70 (t, J=7.3 Hz, 2H), 7.62 (t, J=7.8 Hz, 2H), 7.57-7.40 (m, 8H), 7.40-6.35 (m, 756H), 5.90 (m, 2H), 5.67 (m, 2H), 5.46 (d, J=6.8 Hz, 1H), 5.42 (m, 1H), 4.92 (d, J=10.4 Hz, 1H), 4.64 (d, J=7.0 Hz, 1H), 4.47 (s, 1H), 3.64 (d, J=6.6 Hz, 2H), 2.21 (s, 360H), 1.69 (s, 186H), 1.48 (d, J=42.9 Hz, 564H), 1.25 (s, 9H), 0.87 (t, J=6.0 Hz, 3H); $^{13}$C NMR (75 MHZ, DMSO-$d_6$) δ177.32; IR v=3346, 3196, 2937, 1652, 1613, 1451, 1417, 1353, 1322, 1124, 519 cm$^{-1}$.

The PTX-PAAm-COOH (80.00 mg, 0.004 mmol) is then dissolved in water (8 ml). Next, NHS (0.5000 mg, 0.0048 mmol) and EDC·HCl (1.500 mg, 0.008 mmol) are added. The mixture is stirred at r.t. for 24 h. Then, the cyclo-RGD trifluoroacetate (2.4 mg, 0.004 mmol) and the DIPEA (1.4 μL, 0.008 mmol) are added and the mixture is stirred again for 24 hours. PTX-PAAm-RGD is obtained as a white powder after dialysis in Milli-Q water for 4 days and lyophilization (yield 82%). $^1$H NMR (400 MHZ, DMSO-$d_6$) δ8.96 (m, 1H), 8.00 (d, J=7.3 Hz, 2H), 7.85 (d, J=7.2 Hz, 2H), 7.71 (t, J=7.2 Hz, 2H), 7.62 (t, J=7.5 Hz, 2H), 7.48 (m, 11H), 6.76 (m, 720H), 5.90 (m, 2H), 5.68 (m, 2H), 5.46 (d, J=7.0 Hz, 1H), 5.40 (m, 1H), 4.92 (d, J=9.0 Hz, 1H), 4.64 (d, J=6.6 Hz, 1H), 4.46 (s, 1H), 3.64 (d, J=7.1 Hz, 2H), 2.29-1.95 (m, 333H), 1.55 (t, J=53.7 Hz, 713H), 1.25 (s, 8H), 0.87 (t, J=6.9 Hz, 3H); $^{13}$C NMR (75 MHZ, DMSO-$d_6$) δ177.31; IR v=3345, 3195, 2933, 1652, 1614, 1452, 1416, 1351, 1321, 1123, 491 cm$^{-1}$.

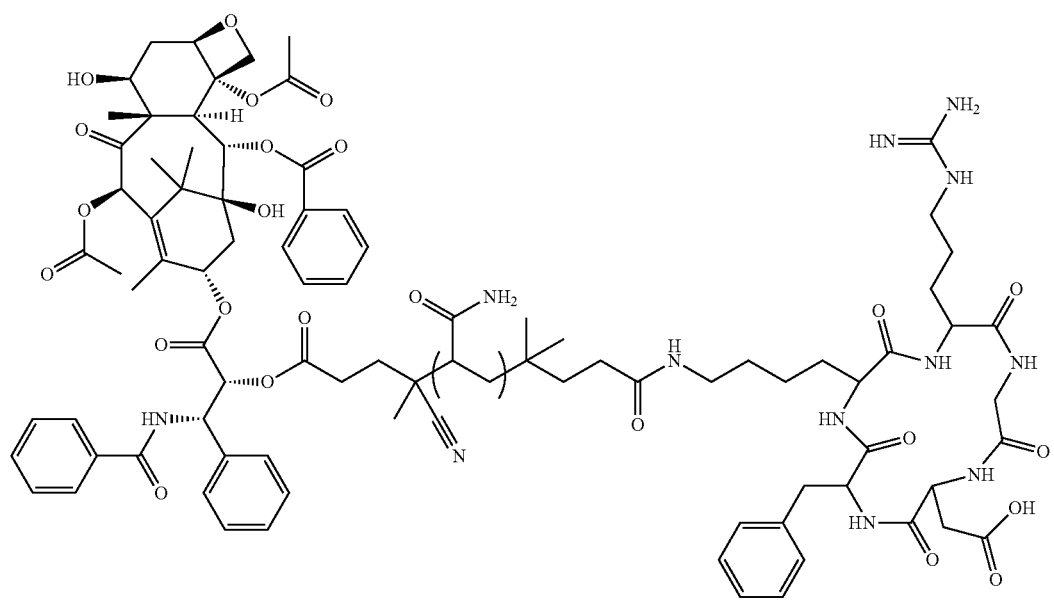

Synthesis of the PTX-PAAm-Rho Polymer

The synthesis of this polymer was carried out by the thiol-maleimide coupling method previously described. First, rhodamine and cyanine were coupled to the maleimide

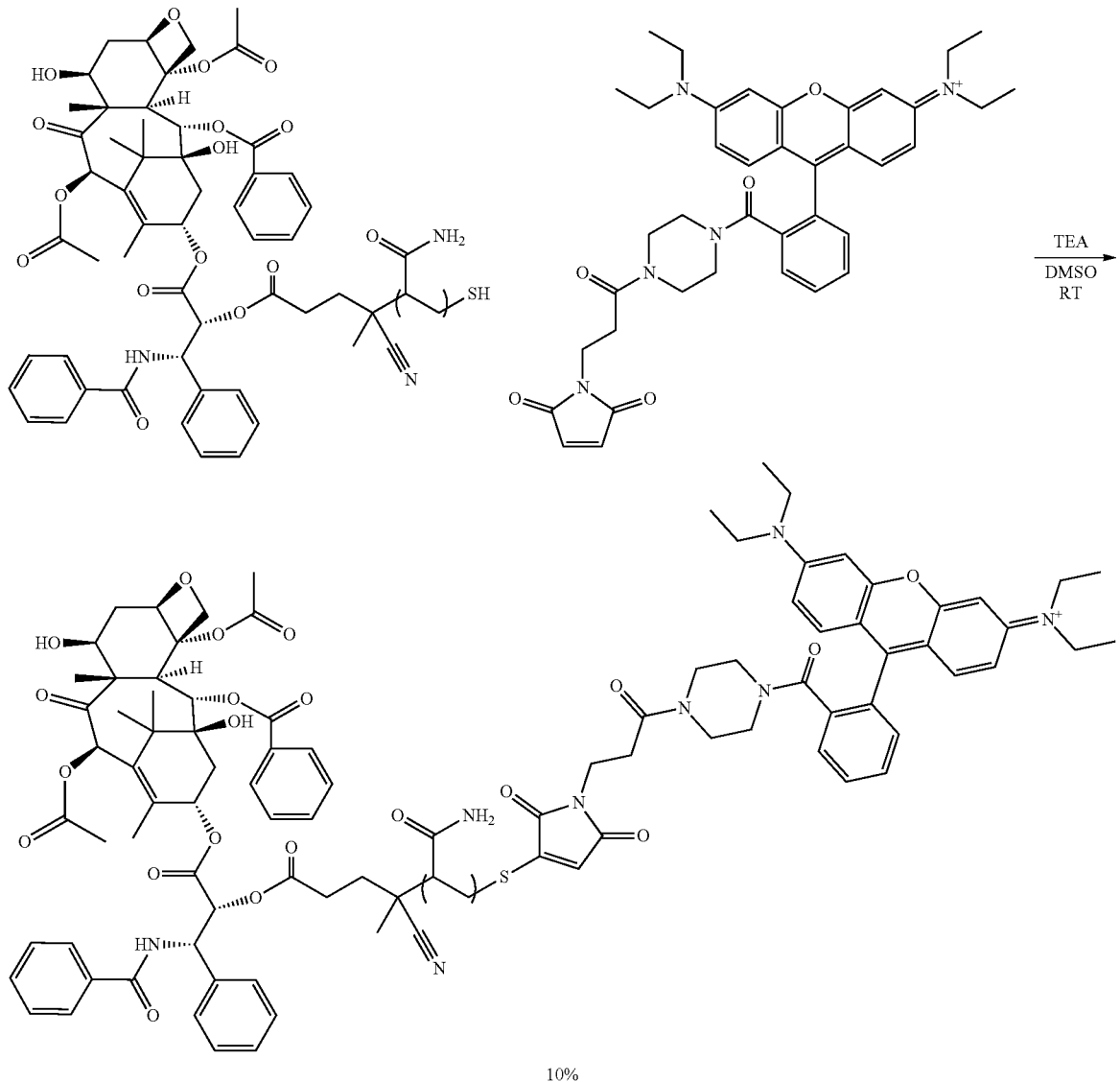

linker, then coupling was carried out between the maleimide function and the thiol of the PTX-PAAm polymer obtained after aminolysis.

PTX-PAAm-SH (30.00 mg, 0.0015 mmol) is dissolved in DMSO (1.5 ml) in a flask. In a separate bottle, Rhodamine-maleimide (2.03 mg, 0.003 mmol) and TEA (1 µl, 0.003 mmol) are dissolved in DMSO (1.5 ml). This solution is added dropwise to the polymer solution. The mixture is stirred under argon at room temperature for 36 h and is then dialyzed in water for three days. PTX-PAAm-Rhodamine is obtained as a pink powder with 73% yield; $^1$H NMR (400 MHz, DMSO-$d_6$) δ8.97 (s, 1H), 8.01 (d, J=7.0 Hz, 2H), 7.85 (d, J=7.3 Hz, 2H), 7.70 (d, J=7.4 Hz, 2H), 7.66-7.60 (m, 2H), 7.48 (m, 9H), 7.36-6.28 (m, 524H), 5.92 (m 2H), 5.47 (d, J=4.9 Hz, 1H), 5.42 (m, 1H), 4.93 (d, J=9.0 Hz, 1H), 4.64 (m, 2H), 4.46 (s, 1H), 4.16 (s, 2H), 3.64 (d, J=7.2 Hz, 2H), 2.20 (s, 281H), 1.70 (s, 123H), 1.48 (d, J=43.7 Hz, 376H), 1.26 (s, 11H), 0.86 (t, J=7.0 Hz, 3H); $^{13}$C NMR (75 MHZ, DMSO-$d_6$) δ177.31; IR v=3337, 3190, 2929, 1651, 1451, 1411, 1318, 1121 cm$^{-1}$.

Example 10: Decrease in SC Toxicity

In vivo tests have shown that, unlike the paclitaxel formulation currently used in clinics (Taxol®), a composition according to the invention does not cause toxicity in the SC tissue after injection. The results obtained with a SC administration of Taxol and of polymer-Paclitaxel at 30 mg/kg (paclitaxel equivalent) once a day for 4 days, show the toxicity at the injection site with Taxol but not with the polymer-Paclitaxel (FIG. 12).

The same studies were carried out with a polymer according to the invention coupled with Cyanine 5.5. Free Cyanine 5.5 is very necrotizing for SC tissue while Cyanine 5.5-PAAm does not cause any SC toxicity (SC administration of Cyanine 5.5 (high) and Cyanine 5.5-polymer (low) at 0.8 mg/kg (cyanine equivalent) once).

The inventors are, to their knowledge, the first to show that the polymeric prodrug approach makes it possible to avoid the irritant/necrotizing effects of AIs after SC injection.

Example 11: Toxicity Study

Figure 9:
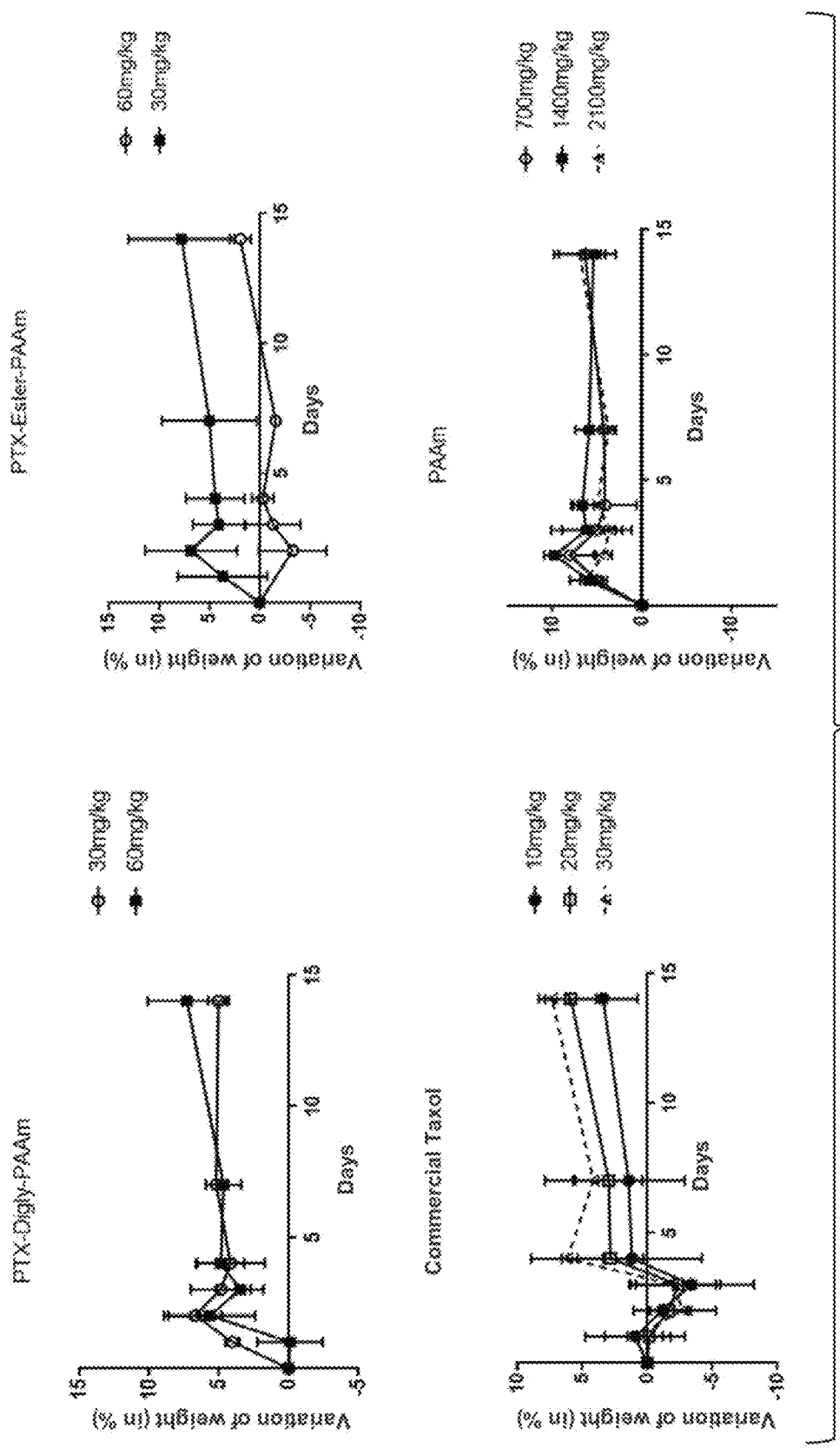
FIG. 9: toxicity study in a murine model. Variation in the weight of the mice as a function of time for PTX-digly-PAAm, PTX-ester-PAAm, Taxol and PAAm.

Toxicity has been studied in mice. Increasing amounts of PTX (commercial formulation of Taxol), PAAm (without PA), PTX-ester-PAAm (Example 2) and PTX-digly-PAAm (Example 8) were injected on DO. The weight of the mouse is followed; a weight loss of −10% is a sign of serious toxicity. No toxicity was observed with the various formulations tested. The results are shown in FIG. 9.

Example 12: Pharmacokinetics and Biodistribution Study (Radiolabelled PTX)

7 week old female BALB/c OlaHsd mice (~22 g; Envigo, France) were used. The radiolabelled Taxol® and the radiolabelled PTX*-PAAm (synthesized as in Example 1 with radiolabelled paclitaxel [3H]-PTX) were injected at a dose of 7 mg·kg$^{-1}$ (1 µCi per mouse) to effect pharmacokinetics and biodistribution studies. The mice were divided into four groups: (i) Taxol® injected intravenously; (ii) Taxol® injected subcutaneously; (iii) PTX-PAAm injected intravenously, and (iv) PTX-PAAm injected subcutaneously. Each group consisted of 40 mice divided into 10 different times (0.25 h, 0.5 h, 1 h, 2 h, 4 h, 7 h, 24 h, 48 h, 96 h and 144 h) leading to 4 mice per group. Radiolabeled PTX was added to the Taxol® formulation, while radiolabelled PTX-PAAm was added to PTX-PAAm (approximately 1 µCi were injected per mouse) to perform pharmacokinetics and biodistribution. At each end point, the mice were euthanized with pentobarbital and the blood was taken by cardiac puncture before the plasma was recovered by centrifugation in tubes containing EDTA (VACUETTE® K3 EDTA tube, centrifugation 5 min, 3000 g). Livers, kidneys, spleens, lungs and some SC tissue at the injection site were also collected. All the samples were stored in a freezer (−20° C.) for a maximum of one week before analysis. For the radioactivity count, approximately 100 µl of plasma and 100 mg of each organ/tissue were removed and weighed with precision. The organs were first dissolved by adding 1 ml of soluble solution (PerkinElmer, USA) and the samples were placed overnight in an oven at 60° C. They were then whitewashed by twice adding 100 µL of 30% $H_2O_2$ (weight/volume) and heated for 30 min at 60° C. in an oven. Finally, the treated plasma and organ samples were mixed with Hionic-FluorUltimagold (PerkinElmer, USA) and the radioactivity was measured with a versatile LS 6500 scintillation counter (Beckman Coulter). Radioactive counting allowed access to the total PTX concentration: [Total PTX]=[free PTX]+[PTX-PAAm]. The results are shown in FIG. 10.

Pharmacokinetic and biodistribution studies were also conducted for the polyacrylamide compound containing paclitaxel. Paclitaxel was radiolabelled and coupled to the polymer by an ester link (stable link) so that it could be followed in the blood and in various organs (liver, lungs, kidneys, spleen, SC tissue). The radiolabeling technique makes it possible to follow the total Paclitaxel (total paclitaxel=coupled paclitaxel+uncoupled paclitaxel). Commercial Taxol is used as a control. At a dose of 7 mg/kg (in paclitaxel equivalent), Taxol injected by the IV route has a short half-life (a few tens of minutes). At the same dose, by the SC route, the combination of its slow absorption and its rapid metabolism leads to very low plasma concentrations (Cmax<1 µg/mL). After IV injection, as shown qualitatively with rhodamine, the coupling of paclitaxel to the polymer leads to a significant increase in half-life and the concentrations are still detectable 6 days after the injection. After SC administration of the polymeric prodrug, significant bioavailability (>85%) is obtained, rapid absorption (Cmax at 4 h) and a half-life comparable to that of IV injection. When comparing the AUC of the polymeric prodrug (total paclitaxel=coupled paclitaxel+uncoupled paclitaxel) to Taxol IV there is an increase by a factor of 70. Coupling to the polymer therefore increases the circulation time of paclitaxel by preventing its metabolism.

Biodistribution studies show a predominantly hepatic elimination of paclitaxel. This is delayed for the paclitaxel polymer in accordance with pharmacokinetics. In the other organs, the quantities are small without worrying accumulation. The quantities of paclitaxel-polymer at the injection site decrease rapidly, which confirms the rapid passage of the prodrug into the circulation and the good bioavailability of the polymer-Paclitaxel.

The present invention therefore makes it possible to increase the solubility, the stability at high concentration and the bioavailability of the active ingredient. These results, combined with the prodrug approach, surprisingly eliminate the toxic effects on the SC tissue.

Example 13: Pharmacokinetics and Biodistribution Study

Figure 11:
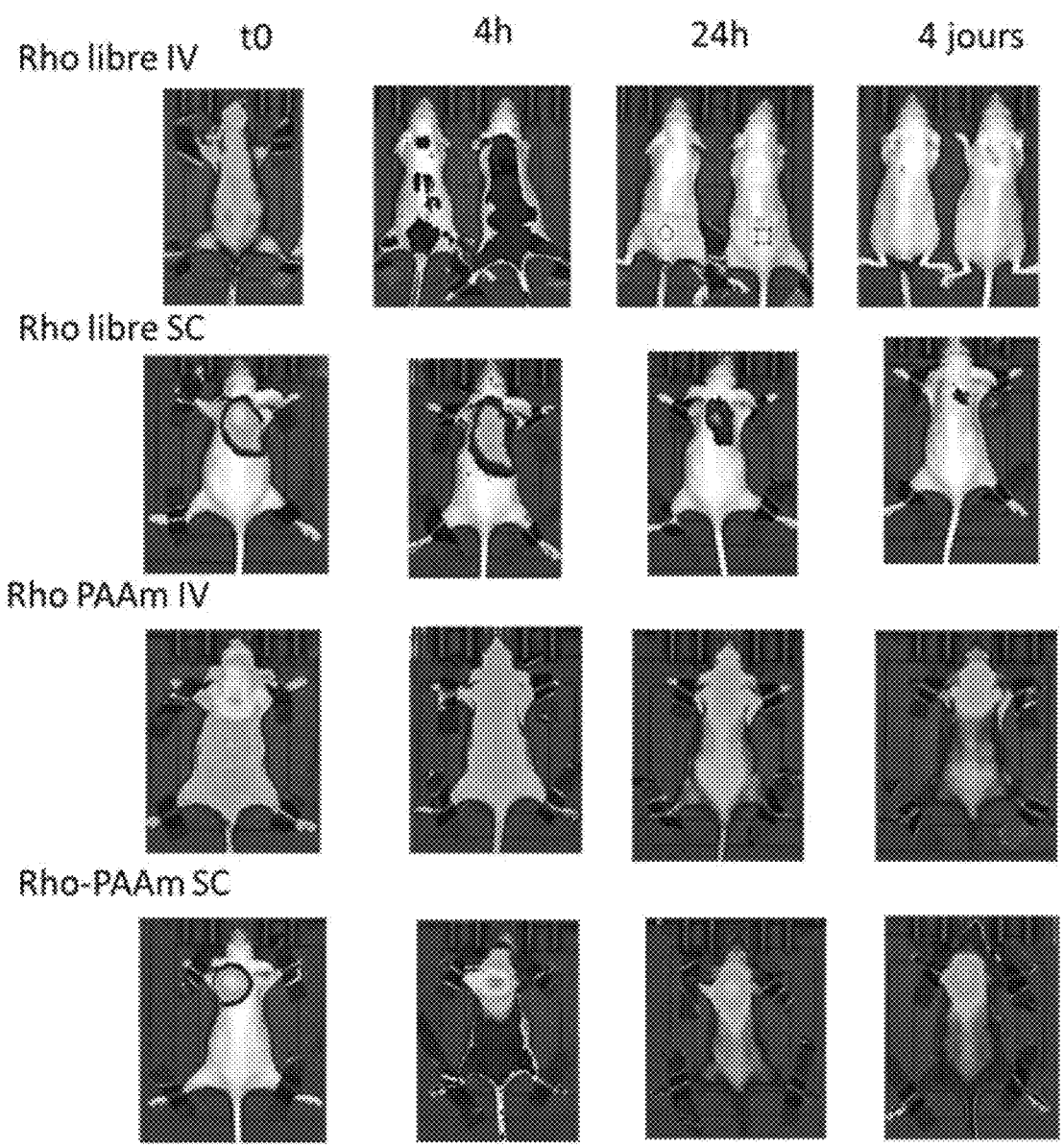
FIG. 11: Biodistribution study in a murine model of free rhodamine and Rhodamine-PAAm administered by the IV and SC routes.

The polyacrylamide was labeled with a fluorescent probe (Rhodamine, example 6) and the fluorescence monitored in vivo in mice using a Lumina imaging system (PerkinElmer) with the excitation filters between 500 and 535 nm, and the filters emission between 575 and 650 nm. The results are shown in FIG. 11.

The free rhodamine injected by the SC route has good bioavailability (the fluorescence decreases in 24 hours at the injection site) and is rapidly eliminated. When Rhodamine-PAAm is injected by route IV, rhodamine is still detectable 4 days after the injection. The grafting to the polymer protects the probe against metabolism and excretion, the half-life is greatly increased. Rhodamine-polymer administered via the SC route is bioavailable and has an increased circulation time (still present at 4 days). These results show that coupling to the polymer increases the circulation time of the active molecule. The present invention is therefore advantageous for slowing down the elimination of the active ingredients once coupled.

The diglycolate bond which frees the PTX more quickly makes it possible to have higher concentrations over time. The ester bond which releases more slowly allows a prolonged release. The carbonate bond releases weakly.

Figure 8:
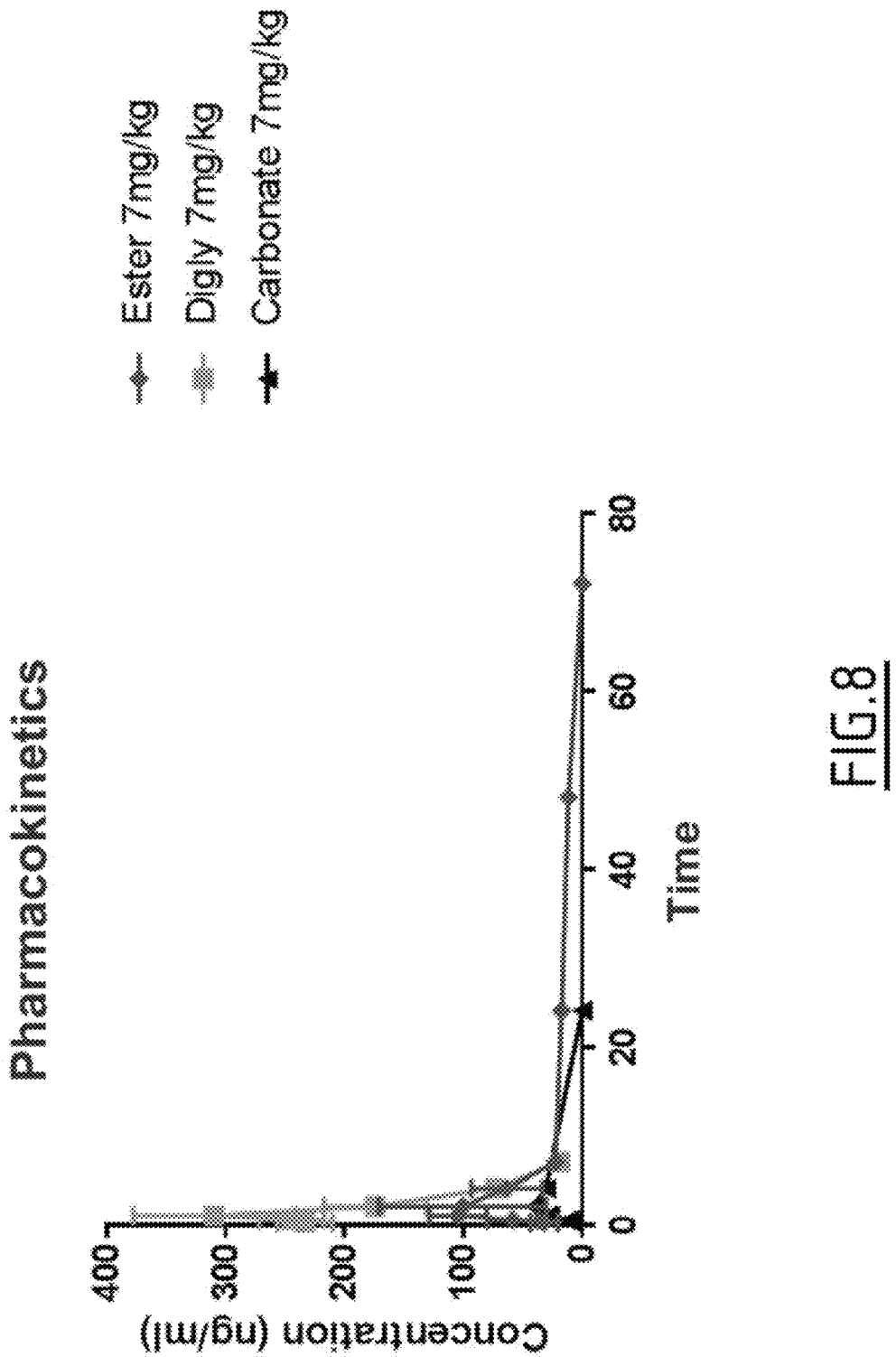
FIG. 8: pharmacokinetics in a murine model of the PTX released in the plasma after degradation of the polymer bond (concentration (mg/ml) as a function of time in minutes) assayed by mass spectrometry.

It is thus possible to vary the release profile according to the polymer of the invention used as illustrated in FIG. 8.
Synthesis of Random and Block Copolymers

Example 14: Synthesis of Gemcitabine-poly (acrylamide-co-acrylonitrile)-CDP

The following example presents the synthesis of a polymer having a polar molecule as a grafted active molecule.
Protection of the Hydroxyl Functions of Gemcitabine In a flask, 4 g (13.3 mmol) of gemcitabine hydrochloride are mixed with 5.1 g (33.8 mmol) of tertbutyldimethylsilylchloride, and 2.75 g (40.4 mmol) of imidazole in 6 g (6.36 ml) of anhydrous DMF. Then 1.5 g (2.07 ml or 14.9 mmol) of triethylamine are added dropwise. The mixture is stirred at 25° C. for 24 h.

The imidazole salts are filtered and the DMF is evaporated. A saturated aqueous solution of $NaHCO_3$ is added and this solution is extracted with ethyl acetate (3 times). The organic EtOAc phases are grouped and washed with brine then dried over $MgSO_4$ and concentrated.

The residue is purified by flash chromatography on silica gel (Eluent: EtOAc).

5.94 g of GemTBDMS are obtained in the form of a white powder, i.e. a yield of 93%.

Coupling of GemTBDMS to CDP 1.2 g (2.97 mmol) of CDP are added to a mixture of 9 g (10.12 ml) of anhydrous THF and 370 mg (510 µl or 3.66 mmol) of triethylamine. The mixture is cooled to 0° C. and a solution of ethyl chloroformate (190 µl or 2.03 mmol is added dropwise in 3.6 g (4.05 ml) of THF. The mixture is stirred at 0° C. for 30 minutes.

A solution of 1 g (2.03 mmol) GemTBDMS is added dropwise into 6 g (6.36 ml) of DMF. The reaction mixture is stirred at 20° C. for 2 days.

The volatile solvents are evaporated. The solution obtained is diluted with brine and extracted with ethyl acetate. The EtOAc phases are grouped and washed with brine then dried over $MgSO_4$ then concentrated in a rotary evaporator.

The residue is purified by flash chromatography on silica gel (Eluent: petroleum ether/EtOAc 4:1).

699.4 mg of GemTBDMS-CDP are obtained in the form of a yellow/orange paste, i.e. a yield of 39.2%.

Grafting of the Poly (AAm-Co-AN) Polymer Chain 3.73 mg (0.023 mmol) AIBN, 45.88 mg (0.114 mmol) GemTBDMS-CDP, 415.46 mg (5.85 mmol) AAA, 152.87 mg (2.88 mmol) of AN and 2.40 g (2.182 ml) of DMSO are introduced into a straight bottle fitted with a magnetic bar. The flask is sealed with a septum and the reaction mixture is bubbled with argon for 15 min. The reaction mixture is introduced into an oil bath previously heated to 70° C. and the reaction runs for 24 h with stirring.

Subsequently, the GemTBDMS-P polymer (AAm-co-AN) is precipitated once in methanol and then dried.

De-Protection of the Hydroxyl Functions of Gemcitabine-TBDMS-P (AAm-Co-AN)

About 700 mg of polymer is dissolved in 5.5 ml of DMSO to which 880 µl of TBAF are added. The reaction mixture is left for 45 min with stirring at room temperature. The whole is then precipitated in cold methanol.

The $^1$H NMR spectrum confirms the presence of Gem-P (AAm-co-AN).

The product obtained is characterized by a molar mass of 25,700 g/mol.

Example 15: Synthesis of Paclitaxel-Poly Polymers (AAm-Co-AN)

Coupling of Paclitaxel (PTX) to CDP According to Example 1

Grafting of the Poly Polymer Chain (AAm-Co-AN)

By applying the grafting protocol derived from Example 1 with addition of the acrylonitrile monomer, several polymers of Paclitaxel-Poly (AAm-co-AN)-CDP are obtained and presented in Table 1. The advantage of this copolymer comes from its UCST thermosensitivity.

TABLE 1

Presentation of the starting products for the synthesis of the CDP-P (AAm-co-AN), PTX-P (AAm-co-AN) polymers obtained.

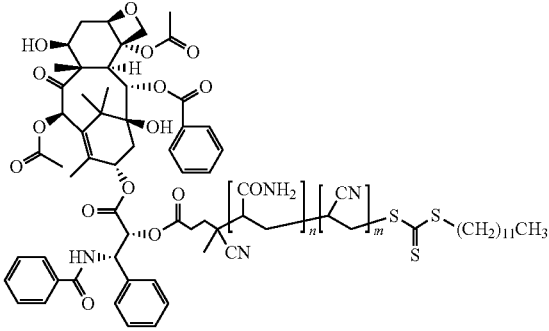

PTX-P (AAm-co-AN)

| Polymer | AAm (mg) | AN (mg) | CDP (mg) | AIBN (mg) | DMSO (g) |
|---|---|---|---|---|---|
| CDP-33%-5 | 415.46 | 152.87 | 45.88 | 3.73 | 2.40 |
| PTX-33%-10 | 415.46 | 152.87 | 140.90 | 3.73 | 2.40 |

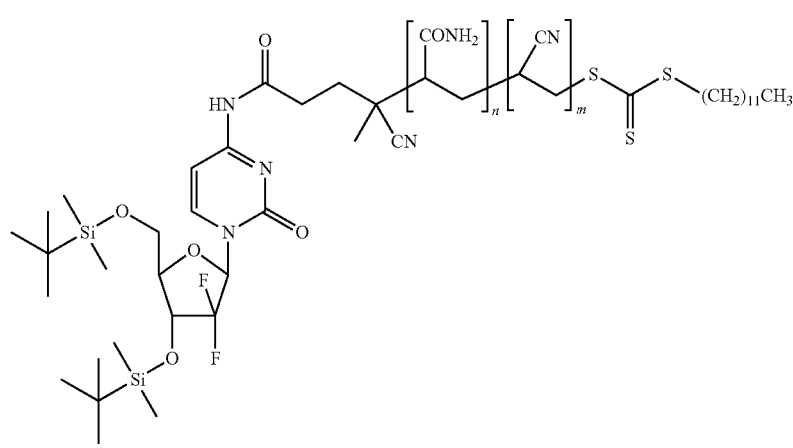

GemTBDMS-CDP-Poly(AAm-co-AN)

TABLE 1-continued

| | | | | | |
|---|---|---|---|---|---|
| PTX-30%-5 | 415.46 | 133.02 | 135.97 | 3.60 | 2.30 |
| PTX-24%-5 | 415.46 | 98.01 | 127.30 | 3.27 | 2.11 |
| PTX-21%-5 | 415.46 | 82.50 | 123.45 | 3.27 | 2.03 |
| PTX-0%-5 | 415.46 | 0 | 103 | 2.73 | 1.61 |
| PTX-0%-10 | 415.46 | 0 | 51.50 | 1.36 | 1.61 |
| PTX-0%-20 | 2492.78 | 0 | 154.50 | 4.09 | 9.64 |
| PTX-5%-15 | 415.46 | 16.32 | 38.90 | 1.03 | 1.69 |
| PTX-10%-15 | 415.46 | 34.46 | 40.53 | 1.07 | 1.79 |
| PTX-15%-15 | 415.46 | 54.73 | 42.36 | 1.12 | 1.89 |
| PTX-13%-15 | 415.46 | 46.34 | 41.6 | 1.10 | 1.85 |
| PTX-19%-15 | 415.46 | 72.80 | 40.35 | 1.11 | 1.87 |
| PTX-14%-15 a | 415.46 | 50.46 | 41.97 | 1.11 | 1.8 |

TABLE 2

Characteristics of the synthesized polymers.
UCST measured by temperature ramp.

| Polymer | Molar mass (g/mol) | UCST (° C) |
|---|---|---|
| CDP-33%-5 | 5 000 | 15 |
| Gem-33%-5 | 25 700 | 14 |
| PTX-5%-34.4 | 34.400 | 26.5 |
| PTX-10%-24.5 | 24.500 | 29.5 |
| PTX-14%-18.2 | 18.200 | 30.0 |
| PTX-19%-18.7 | 18.700 | 37.5 |
| PTX-22%-22 | 22.000 | 49.5 |
| PTX-24%-17.8 | 17.800 | 58.0 |
| PTX-25%-14.6 | 14.600 | >60.0 |
| PTX-30%-14 | 14.000 | >60.0 |

Example 16: Transmittance Measurements as a Function of Temperature

This example demonstrates for the first time, to the knowledge of the inventors, copolymers grafted with active molecules by the method of the initiator active ingredient which are thermosensitive and which have a UCST, see FIG. 1.

The transmittance results as a function of the temperature are summarized in Table 2.

The UCST is determined as the temperature where the transmittance reaches approximately 100%, i.e. when the polymer is completely dissolved.

Example 17: Synthesis of the PTX-P Diblock Polymer (AAm-Co-AN)-b-PEGMA 1.7 mg (0.01 mmol) of AIBN, 100 mg of PTX-33%-10 synthesized as indicated in Example 16, 37.5 mg (0.125 mmol) of PEGMA and 2.475 g (2.25 ml) of DMSO are introduced into a straight bottle provided with a magnetic bar. The flask is sealed with a septum and the reaction mixture is bubbled with argon for 15 min. The reaction mixture is introduced into an oil bath previously heated to 70° C., and the reaction runs for 5 h with stirring.

At the end of the reaction, the polymer is dialyzed against 1 l of water for 24 h. The water is changed every 4 hours during the day. After dialysis, the polymer is lyophilized. White pasty flakes are obtained.

The $^1$H-NMR spectrum of the product obtained confirms the presence of the polymerization of PEGMA on the product PTX-33%-10.

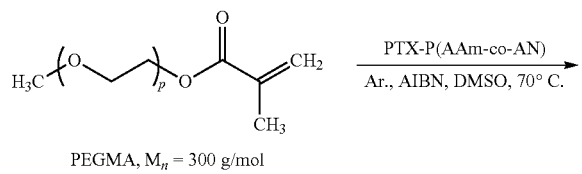

PEGMA, $M_n$ = 300 g/mol

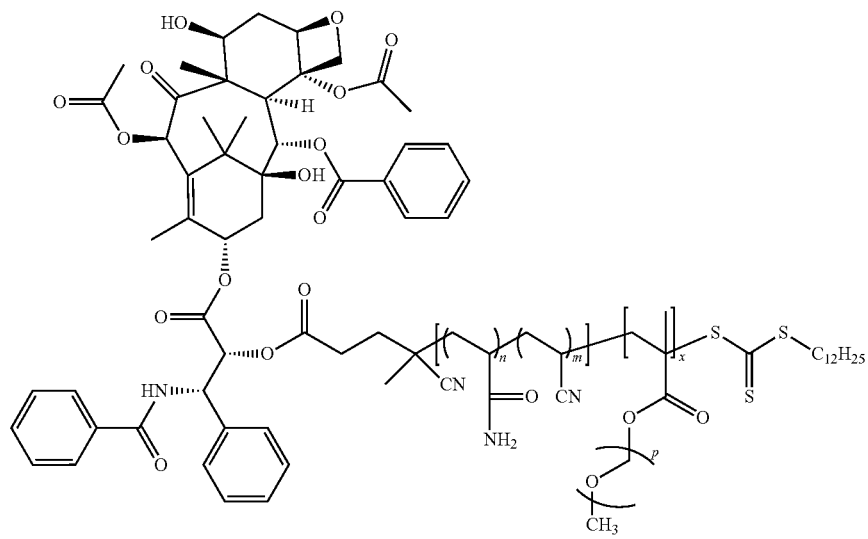

PTX-P(AAm-co-AN)-b-PEGMA

According to the same protocol, other PTX-P (AAm-co-AN)-b-PEGMA diblock copolymers were synthesized and presented in Table 4.

TABLE 4

Characteristics of the synthesized block copolymers.
The UCST is measured by temperature ramp.

| Sample | Polymer | Experimental AN (% mol) | Mn (g/mol) |
|---|---|---|---|
| CP2-PEGMA | PTX-10%-24,5-PEGMA-1,8 | 8 | 26 300 |
| CP3-PEGMA | PTX-14%-18,2-PEGMA-1,3 | 11 | 19 500 |
| CP4-PEGMA | PTX-19%-18,7-PEGMA-1,3 | 15 | 20 000 |
| CP5-PEGMA | PTX-22%-22-PEGMA-1,8 | 20.3 | 23 800 |
| CP6-PEGMA | PTX-24%-17,8-PEGMA-1,6 | 18.8 | 19 400 |
| CP7-PEGMA | PTX-25%-14,6-PEGMA-1,1 | 20.5 | 15 700 |
| CP8-PEGMA | PTX-30%-14-PEGMA-1,1 | 19.4 | 15 100 |

For each PTX-P (AAm-co-AN) random copolymer, a PEGMA chain of 1400 to 2000 g/mol in length was added.

CP5-PEGMA and CP7-PEGMA were analyzed by UV-visible spectrometer to determine their UCST as being 41° C. and 52° C. respectively with low hysteresis (of the order of 1 to 2° C.).

The comparison of the curves obtained for CP5 and those for the suspension of CP5-PEGMA, leads to the deduction that the value of UCST decreases by a few degrees due to the hydrophilic nature of the PEGMA block. The results of this comparative test are presented in FIG. 2.

Example 18: Solubility of the Polymeric Prodrug PTX-PAAm-Co-AN as a Function of the % of AN The viscosity of PTX-(PAAm-co-AN) solutions with AN levels between 0% and 15% up to a concentration of 50 mg/ml, was measured.
Viscosity Protocol (Depending on the Shear Rate):

A rheometer (ARG2, TA Instrument) was used with a plane-plane geometry of dimension d=20 mm with solvent cup, thermostatically controlled at 20° C. and fitted with a plastic solvent bell. The sample is dropped on the bottom using a plastic pipette, and the solvent cup is filled with water. The device places the two planes at a distance of 200 nm and the surplus is eliminated in order to avoid parasitic friction.
The Procedure Applied is then as Follows:
  equilibration of the sample at 20° C. for 2 minutes.
  measurement of the applied torque for a shear rate varying from 10 to 1000 s$^{-1}$ (5 measurements per decade, 3 minutes of maximum equilibration for each measurement).

Figure 13:
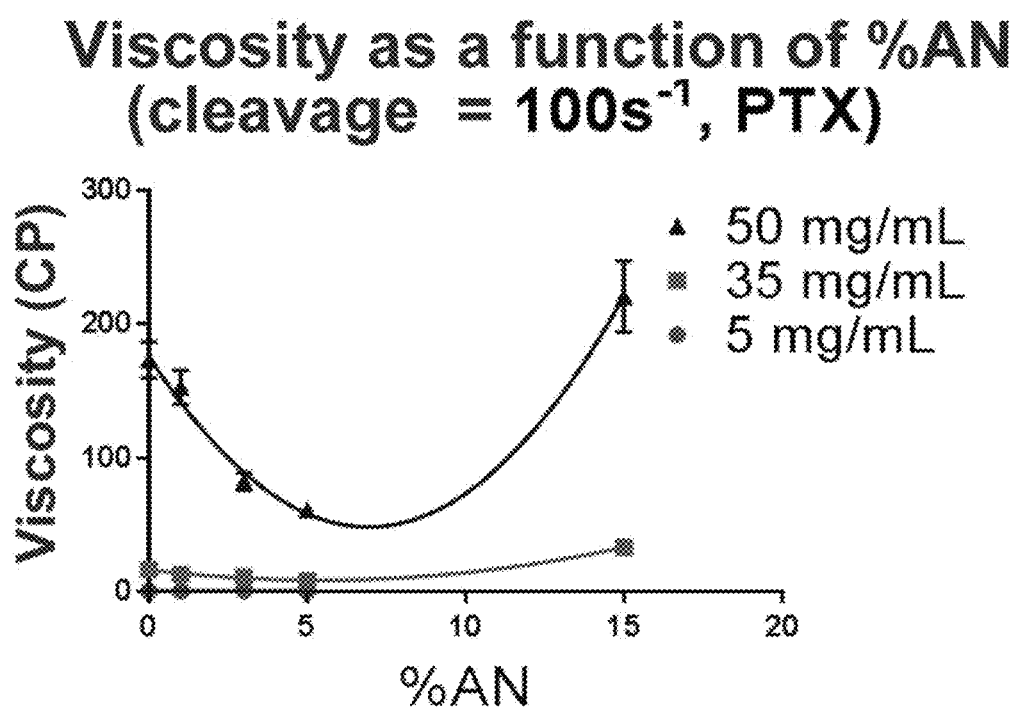
FIG. 13: Viscosity of polymeric paclitaxel prodrug solutions as a function of the concentration and content of acrylonitrile (AN) in the polymer. These measurements were obtained using a rheometer with plane-plane geometry.

According to FIG. 13, the viscosity decreases with an increase in the acrylonitrile level, up to 5 mol % and the effect is demonstrated up to 50 mg/ml in PTX-P (AAm-co-AN).

Example 19: Toxicity Test with PTX-21%-5

A local toxicity test is carried out in mice with PTX-21%-5. On a group of 3 "nude" mice, 0.6 mg of PTX in 200 µl of PBS solution are administered subcutaneously. This injection is repeated 4 times over 4 consecutive days. At the end of the third day, local toxicity (acute irritation, slight necrosis) appeared in the vicinity of the injection site for all the mice, as shown in FIG. 3.

The same dose of paclitaxel formulated with polymeric prodrug PTX-21%-5 (corresponding to a polymer concentration of 17.6 mg/ml). As shown in FIG. 3, after the four injections, the group of 3 mice showed no evidence of local toxicity.

What is claimed is:

1. A polymeric prodrug comprising a linear chain, said linear chain comprising:
   a polymer chain (PAAm) consisting of poly (acrylamide) located between a terminal part and a proximal part;
   said proximal part comprising:
     i) a proximal part of a reversible Addition-Fragmentation Chain Transfer (RAFT) radical polymerization control agent comprising a proximal function or a linker;
     ii) a pharmaceutically active molecule selected from the group consisting of paclitaxel, docetaxel, cabazitaxel, and wherein the pharmaceutically active molecule is covalently coupled to said proximal part of the RAFT radical polymerization control agent through the proximal function or the linker; and
   said terminal part comprising a terminal part of the RAFT radical polymerization control agent; and
wherein:
   said RAFT radical polymerization control agent is 4-cyano-4-[(dodecylsulfanylthiocarbonyl) sulfanyl] pentanoic acid (CDP); and
   said polymeric prodrug is of formula:

where:
  PAAm represents said polymer chain;
  TAX represents said pharmaceutically active molecule;
  FUNC represents said proximal function or said linker selected from the group consisting of:

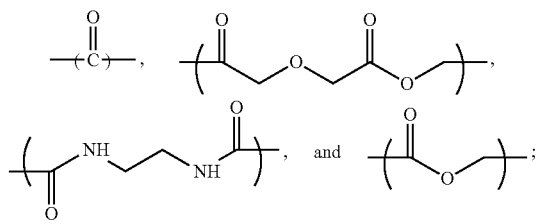

said pharmaceutically active molecule is capable of being released from the polymeric prodrug by cleavage of a covalent bond following administration to a patient in need.

2. The polymeric prodrug according to claim 1, wherein the poly (acrylamide) has a dispersity less than 1.5, said dispersity being determined by steric exclusion chromatography.

3. The polymeric prodrug according to claim 1, wherein the poly (acrylamide) has a molar mass of 1000 to 1,000,000 g/mol.

4. The polymeric prodrug according to claim 1 wherein the polymeric prodrug induces a spread over time of the pharmaceutically active molecule in the patient in need thereof.

5. A method of therapeutic treatment or of diagnosis wherein said method comprises the subcutaneous or intramuscular administration to a human or animal of a polymeric prodrug according to claim 1.

6. The method of claim 5, wherein said pharmaceutically active molecule is not administerable by the subcutaneous or intramuscular route due to its toxicity at the injection site when it is not covalently coupled by the covalent bond to said poly (acrylamide).

7. The method according to claim 5, wherein the method of treatment is a method of treating cancer.

8. A method for controlled radical polymerization of at least one polymeric prodrug according to claim 1, said method comprising the steps:
   covalently coupling at least one pharmaceutically active molecule with a radical polymerization control agent comprising a proximal part and a terminal part, to form a coupled molecule;
   polymerizing by controlled radical polymerization the coupled molecule in the presence of acrylamide monomers, to form the polymeric prodrug;
   optionally, covalently coupling a second pharmaceutically active molecule in the terminal part of the control agent after controlled radical polymerization of the polymer.

9. A method for controlled radical polymerization of at least one polymeric prodrug according to claim 1, said method comprising the steps:
   polymerizing by controlled radical polymerization a polymer in the presence of acrylamide monomers, to form a polymer comprising a proximal part and a terminal part;
   covalently coupling a pharmaceutically active molecule with the proximal part of the polymer, to form said polymeric prodrug.

10. A medicament comprising at least one polymeric prodrug according to claim 1.

11. A composition formulated for its injection by subcutaneous or intramuscular route into tissue of a mammal, said composition comprising a polymeric prodrug as defined in claim 1.

12. The polymeric prodrug according to claim 1, wherein the poly (acrylamide) has a molar mass of less than 100,000 g/mol.

13. The polymeric prodrug according to claim 1, wherein the poly (acrylamide) has a molar mass of less than 50,000 g/mol.

14. The polymeric prodrug according to claim 4, wherein the site of action is a tumor or intracellular.

15. The polymeric prodrug of claim 1, wherein said polymeric prodrug has a bioavailability of the pharmaceutically active molecule preventing local toxicities and releases the pharmaceutically active molecule in blood circulation.

16. The polymeric prodrug of claim 1 wherein the pharmaceutically active molecule is paclitaxel and the proximal function is

and said polymeric drug is of formula:

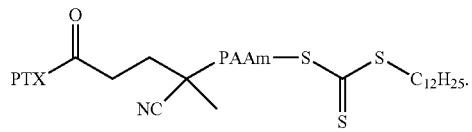

17. The polymeric prodrug of claim 1 wherein the pharmaceutically active molecule is covalently coupled at an oxygen atom of a hydroxyl group of a side chain of said paclitaxel, docetaxel or cabazitaxel to said proximal part of the RAFT radical polymerization control agent through the proximal function or linker.

* * * * *